United States Patent
Machinaga et al.

(10) Patent No.: US 8,653,126 B2
(45) Date of Patent: Feb. 18, 2014

(54) IMIDAZOLE DERIVATIVE

(75) Inventors: Nobuo Machinaga, Tokyo (JP); Jun Chiba, Tokyo (JP); Fumihito Muro, Tokyo (JP); Hiroshi Yuita, Tokyo (JP); Jun Watanabe, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/579,791

(22) PCT Filed: Feb. 17, 2011

(86) PCT No.: PCT/JP2011/053336
§ 371 (c)(1),
(2), (4) Date: Aug. 17, 2012

(87) PCT Pub. No.: WO2011/102404
PCT Pub. Date: Aug. 25, 2011

(65) Prior Publication Data
US 2012/0316170 A1    Dec. 13, 2012

(30) Foreign Application Priority Data
Feb. 18, 2010  (JP) .................. 2010-033413

(51) Int. Cl.
*A61K 31/4172* (2006.01)
*C07D 233/64* (2006.01)

(52) U.S. Cl.
USPC ................ 514/399; 548/333.5

(58) Field of Classification Search
USPC ............. 548/333.5; 514/399
See application file for complete search history.

(56) References Cited

U.S. PATENT DOCUMENTS

| | | | |
|---|---|---|---|
| 7,649,098 B2 * | 1/2010 | Augeri et al. | 548/336.1 |
| 2009/0318516 A1 | 12/2009 | Burgoon et al. | |

FOREIGN PATENT DOCUMENTS

| | | |
|---|---|---|
| WO | WO 84/03441 A1 | 9/1984 |
| WO | WO 97/46543 A1 | 12/1997 |
| WO | WO 2007/100617 A2 | 9/2007 |
| WO | WO 2008/109314 A1 | 9/2008 |
| WO | WO 2008/128045 A1 | 10/2008 |

OTHER PUBLICATIONS

Bagdanoff, J.T., et al., "Inhibition of Sphingosine-1-Phosphate Lyase for the Treatment of Autoimmune Disorders," *J. Med. Chem.*, 52, pp. 3941-3953 (2009).

Bagdanoff, J.T., et al., Inhibition of Sphingosine 1-Phosphate Lyase for the Treatment of Rheumatoid Arthritis: Discovery of (E)-1-(4-((1R,2S,3R)-1,2,3,4-Tetrahydroxybutyl)-1H-imidazol-2-yl)ethanone Oxime (LX2931) and (1R,2S,3R)-1-(2-(Isoxazol-3-yl)-1H-imidazol-4-yl)butane-1,2,3,4-tetraol (LX2932), *J. Med. Chem.*, 53, pp. 8650-8662 (2010).

Mandala, S., et al., "Alteration of Lymphocyte Trafficking by Sphingosine-1-Phosphate Receptor Agonists," *Science*, 296, pp. 346-349 (2002).

Schwab, S.R., et al., "Lymphocyte Sequestration Through S1P Lyase Inhibition and Disruption of S1P Gradients," *Science*, 309, pp. 1735-1739 (2005).

Yu, X.Q., et al., "Pharmacokinetic/pharmacodynamic modelling of 2-acetyl-4(5)-tetrahydroxybutyl imidazole-induced peripheral lymphocyte sequestration through increasing lymphoid sphingosine 1-phosphate," *Xenobiotica*, 40(5), pp. 350-356 (2010).

Gilenya® Product Data Sheet, Novartis Pharmaceuticals Corp., East Hanover, New Jersey, USA, 2012, 17 pages.

* cited by examiner

*Primary Examiner* — Kamal Saeed
*Assistant Examiner* — Janet L Coppins
(74) *Attorney, Agent, or Firm* — Dorsey and Whitney LLP

(57) ABSTRACT

To provide a novel compound or an isotope thereof or a pharmaceutically acceptable salt thereof having S1P lyase inhibitory capacity and inducing the decrease in number of lymphocytes, and a pharmaceutical composition containing these as active ingredients. A compound represented by the general formula (I):

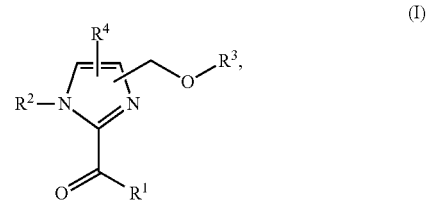

or the general formula (II):

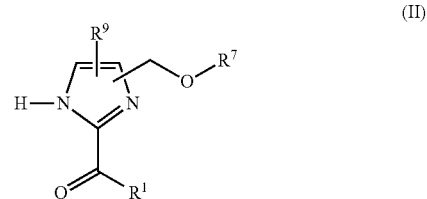

or an isotope thereof or a pharmaceutically acceptable salt thereof.

15 Claims, No Drawings

IMIDAZOLE DERIVATIVE

This application is a national stage application under 35 U.S.C. §371 of International Application No. PCT/JP2011/053336, filed Feb. 17, 2011, entitled "Imidazole Derivative," which claims priority to Japanese Patent Application No. 2010-033413, filed Feb. 18, 2010, the contents of all of which are hereby incorporated in their entirety by reference.

TECHNICAL FIELD

The present invention relates to novel imidazole derivatives or isotopes thereof or pharmaceutically acceptable salts thereof having sphingosine-1-phosphate (hereinafter, also referred to as S1P) lyase inhibitory activity, and to pharmaceutical compositions containing these as active ingredients.

BACKGROUND ART

Currently, as immunosuppressive agents, for example, cyclosporine, tacrolimus, and the like are utilized, which suppress the production of cytokines such as IL-2. In recent years, research has been conducted with regard to compounds which suppress the activity of the immune system by inducing a decrease in the number of lymphocytes in the blood. For example, fingolimod shows no action of suppressing the production of cytokines in vitro, but acts as a S1P receptor agonist after being phosphorylated in vivo, inducing a decrease in the number of lymphocytes in the blood. This allows the activity of the immune system to be suppressed (see, e.g., Non-Patent Document 1).

As compounds inducing a decrease in the number of lymphocytes in the blood by means of a mechanism other than as a S1P receptor agonist, 2-acetyl-4-tetrahydroxybutylimidazole (THI) (see, for example, Patent Document 1) is known. THI induces a decrease in the number of lymphocytes in the blood by inhibiting S1P lyase (see, e.g., Non-Patent Document 2, Non-Patent Document 3, etc.).

As such S1P lyase inhibitors, other than THI, an imidazole derivative having a polyol as a substituent (see, e.g., Patent Document 2, Patent Document 3, Non-Patent Document 4, Non-Patent Document 5, etc.), an imidazole derivative with a hetero ring being bonded directly thereto (see, e.g., Patent Document 4, Patent Document 5, Non-Patent Document 4, Non-Patent Document 5, etc.), and the like are known. Further, as compounds inducing a decrease in the number of lymphocytes, a thiazole derivative having a polyol as a substituent (see, e.g., Patent Document 6), and the like are known.

PRIOR ART DOCUMENTS

Patent Documents

[Patent Document 1] WO 84/03441
[Patent Document 2] WO 07/100,617
[Patent Document 3] WO 08/128,045
[Patent Document 4] WO 08/109,314
[Patent Document 5] US 2009/0318516 A
[Patent Document 6] WO 97/46543

Non-Patent Documents

[Non-Patent Document 1] Science, 296, 346-349 (2002)
[Non-Patent Document 2] Science, 309, 1735-1739 (2005)
[Non-Patent Document 3] Xenobiotica, 2010; 40(5): 350-356
[Non-Patent Document 4] J. Med. Chem. 2009, 52, 3941-3953
[Non-Patent Document 5] J. Med. Chem. 2010, 53, 8650-8662

SUMMARY OF THE INVENTION

Problems to be Solved by the Invention

However, the compound of the present invention is not specifically described in any of the above-mentioned Patent Documents 1 to 6 and Non-Patent Documents 1 to 4.

Thus, the present invention has an object of providing a novel compound or an isotope thereof or a pharmaceutically acceptable salt thereof having S1P lyase inhibitory capacity and inducing a decrease in the number of lymphocytes, and a pharmaceutical composition containing these as active ingredients.

Means for Solving the Problems

The present invention provides:
(1) a compound represented by the general formula (I):

[Chemical 1]

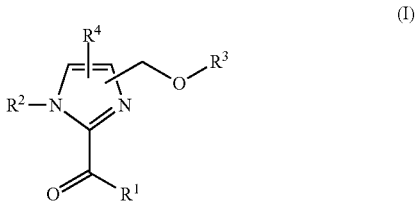

wherein,
$R^1$ is a methyl group which may be substituted with the same or different 1 to 3 halogen atoms,
$R^2$ is a C1-C6 alkyl group which may be substituted with the same or different 1 to 3 halogen atoms, a C3-C6 cycloalkyl group, a C1-C6 alkoxy C1-C6 alkyl group, a C3-C6 cycloalkoxy C1-C6 alkyl group, a C2-C6 alkenyl group, a di(C1-C6 alkyl)amino group, a furanylmethyl group, an oxetanyl group, an acetyloxymethyl group, a propylcarbonyloxymethyl group, a tert-butylcarbonyloxymethyl group, a phenylcarbonyloxymethyl group, a hydroxymethyl group, a dimethylaminosulfonyl group, a diethylaminosulfonyl group, a pyrrolidinesulfonyl group, a piperidinesulfonyl group or a morpholinesulfonyl group,
$R^3$ is a hydrogen atom, an acetyl group, a benzoyl group or a pivaloyl group, and
$R^4$ is a hydrogen atom or a halogen atom] or an isotope thereof or a pharmaceutically acceptable salt thereof;
(2) the compound or isotope thereof or pharmaceutically acceptable salt thereof described in (1) above, wherein $R^1$ is a methyl group which may be substituted with 1 to 3 fluorine atoms;
(3) the compound or isotope thereof or pharmaceutically acceptable salt thereof described in (1) above, wherein $R^1$ is a methyl group or a difluoromethyl group;
(4) the compound or isotope thereof or pharmaceutically acceptable salt thereof described in any one of (1) to (3) above, wherein $R^2$ is a C2-C6 alkyl group, a cyclopropyl group, a C1-C2 alkoxy C1-C3 alkyl group, a cyclohexyloxymethyl group, a vinyl group, a furanylmethyl group, an oxetanyl group or a dimethylaminosulfonyl group;

(5) the compound or isotope thereof or pharmaceutically acceptable salt thereof described in any one of (1) to (3) above, wherein $R^2$ is an ethyl group, a propyl group, a sec-butyl group, a tert-butyl group, a pentyl group, a hexyl group, a cyclopropyl group, a methoxymethyl group, a methoxyethyl group, a methoxyisopropyl group, an ethoxymethyl group, a cyclohexyloxymethyl group, a vinyl group, a furanylmethyl group, an oxetanyl group or a dimethylaminosulfonyl group;

(6) the compound or isotope thereof or pharmaceutically acceptable salt thereof described in any one of (1) to (3) above, wherein $R^2$ is an ethyl group or a vinyl group;

(7) the compound or isotope thereof or pharmaceutically acceptable salt thereof described in any one of (1) to (6) above, wherein $R^3$ is a hydrogen atom;

(8) the compound or isotope thereof or pharmaceutically acceptable salt thereof described in any one of (1) to (7) above, wherein $R^4$ is a hydrogen atom;

(9) a compound represented by the general formula (II):

[Chemical 2]

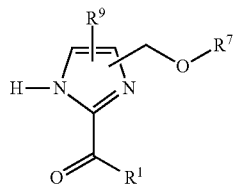

(II)

[wherein, $R^1$ is a methyl group which may be substituted with the same or different 1 to 3 halogen atoms, $R^7$ is a hydrogen atom or —C(O)—$R^8$, $R^8$ is a C1-C8 alkyl, a C3-C8 cycloalkyl, a phenyl, a pyridyl, a naphthyl, an amino, a pyrrolidinyl, a piperidinyl or a morpholinyl group which may have the same or different 1 to 3 substituents selected from substituent group α, the substituent group α is the group consisting of a halogen atom, a hydroxy group, a C1-C8 alkyl group, a C3-C8 cycloalkyl group, a C1-C8 alkoxy group, a C3-C8 cycloalkoxy group, an amino group, a mono or di(C1-C8 alkyl)amino group, a carboxyl group, a C1-C8 alkoxycarbonyl group, a phenyl group, a pyridyl group, a phenoxy group, a phenyl C1-C6 alkoxy group, a tert-butyloxycarbonylpiperidinyl group, a (2-acetyl-1H-imidazol-4-yl)methyloxycarbonyl group, a (2-acetyl-3H-imidazol-4-yl)methyloxycarbonyl group and an oxocyclopentylmethylphenyl group, and $R^9$ is a hydrogen atom, a halogen atom or a C1-C6 alkyl group] or an isotope thereof or a pharmaceutically acceptable salt thereof;

(10) the compound or isotope thereof or pharmaceutically acceptable salt thereof described in (9) above, wherein $R^1$ is a methyl group which may be substituted with 1 to 3 fluorine atoms;

(11) the compound or isotope thereof or pharmaceutically acceptable salt thereof described in (9) above, wherein $R^1$ is a methyl group or a difluoromethyl group;

(12) the compound or isotope thereof or pharmaceutically acceptable salt thereof described in any one of (9) to (11) above, wherein $R^7$ is a hydrogen atom;

(13) the compound or isotope thereof or pharmaceutically acceptable salt thereof described in any one of (9) to (12) above, wherein $R^9$ is a hydrogen atom;

(14) a compound selected from the group consisting of:
1-(4-hydroxymethyl-1-methoxymethyl-1H-imidazol-2-yl) ethanone,
1-(4-hydroxymethyl-1-isopropyl-1H-imidazol-2-yl)ethanone,
1-(4-hydroxymethyl-1-vinyl-1H-imidazol-2-yl)ethanone,
1-(4-hydroxymethyl-1H-imidazol-2-yl)ethanone,
1-(5-hydroxymethyl-1H-imidazol-2-yl)ethanone,
1-[4-[hydroxy[($^2$H)$_2$]methyl]-1H-imidazol-2-yl]ethanone,
1-[5-[hydroxy[($^2$H)$_2$]methyl]-1H-imidazol-2-yl]ethanone,
1-[4-[hydroxy[($^2$H)$_2$]methyl]-1-methoxymethyl-1H-imidazol-2-yl]ethanone,
benzoic acid (2-acetyl-1H-imidazol-4-yl)methylester,
benzoic acid (2-acetyl-3H-imidazol-4-yl)methylester,
cis-cyclohexane-1,3-dicarboxylic acid bis[(2-acetyl-1H-imidazol-4-yl)methyl]ester,
cis-cyclohexane-1,3-dicarboxylic acid bis[(2-acetyl-3H-imidazol-4-yl)methyl]ester,
cis-cyclohexane-1,3-dicarboxylic acid 1-(2-acetyl-1H-imidazol-4-yl)methyl 3-(2-acetyl-1H-imidazol-4-yl)methylester, and
cis-cyclohexane-1,3-dicarboxylic acid 1-(2-acetyl-3H-imidazol-4-yl)methyl 3-(2-acetyl-1H-imidazol-4-yl)methylester;

(15) a pharmaceutical composition containing as an active ingredient the compound or isotope thereof or pharmaceutically acceptable salt thereof described in any one of (1) to (13) above or the compound described in (14) above;

(16) the pharmaceutical composition described in (15) above for use in preventing or treating inflammatory bowel disease, acute lung injury, autoimmune disease, multiple sclerosis or allergic disease, or in suppressing rejection response against transplant;

(17) the pharmaceutical composition described in (16) above, wherein the inflammatory bowel disease is ulcerative colitis or Crohn's disease;

(18) the pharmaceutical composition described in (16) above, wherein the autoimmune disease is rheumatoid arthritis, systemic lupus erythematosus, antiphospholipid antibody syndrome, multiple myositis, dermatomyositis, systemic scleroderma, Sjogren's syndrome, polyarteritis nodosa, microscopic polyarteritis, allergic granulomatous angiitis, Wegener's granulomatosis or mixed connective tissue disease;

(19) the pharmaceutical composition described in (16) above, wherein the allergic disease is atopic dermatitis, allergic rhinitis, pollinosis, allergic conjunctivitis, allergic gastroenteritis, bronchial asthma, infantile asthma, food allergy, drug allergy or urticaria;

(20) use of the compound or isotope thereof or pharmaceutically acceptable salt thereof described in any one of (1) to (13) above or the compound described in (14) above for the production of a pharmaceutical composition for preventing or treating inflammatory bowel disease, acute lung injury, autoimmune disease, multiple sclerosis or allergic disease, or for suppressing rejection response against transplant;

(21) a method for preventing or treating inflammatory bowel disease, acute lung injury, autoimmune disease, multiple sclerosis or allergic disease, or for suppressing rejection response against transplant, comprising administering to a mammal a therapeutically effective amount of the compound or isotope thereof or pharmaceutically acceptable salt thereof described in any one of (1) to (13) above or the compound described in (14) above; and

(22) the method described in (21) above, wherein the mammal is a human.

Effect of the Invention

The compound or isotope thereof or pharmaceutically acceptable salt thereof of the present invention has excellent S1P lyase inhibitory capacity and membrane permeability, and achieves an effect of decreasing the number of lymphocytes in the blood in vivo. In addition, the pharmaceutical composition of the present invention achieves effects capable of treating or preventing inflammatory bowel disease, acute lung injury, autoimmune disease, multiple sclerosis, allergic disease, or the like in a mammal, in particular, in a human, and capable of suppressing rejection response against transplant.

MODE FOR CARRYING OUT THE INVENTION

One embodiment of the present invention is a compound represented by the general formula (I):

[Chemical 3]

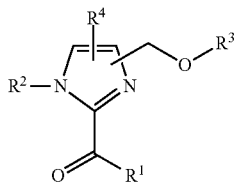
(I)

[wherein,
$R^1$ is a methyl group which may be substituted with the same or different 1 to 3 halogen atoms,
$R^2$ is a C1-C6 alkyl group which may be substituted with the same or different 1 to 3 halogen atoms, a C3-C6 cycloalkyl group, a C1-C6 alkoxy C1-C6 alkyl group, a C3-C6 cycloalkoxy C1-C6 alkyl group, a C2-C6 alkenyl group, a di(C1-C6 alkyl)amino group, a furanylmethyl group, an oxetanyl group, an acetyloxymethyl group, a propylcarbonyloxymethyl group, a tert-butylcarbonyloxymethyl group, a phenylcarbonyloxymethyl group, a hydroxymethyl group, a dimethylaminosulfonyl group, a diethylaminosulfonyl group, a pyrrolidinesulfonyl group, a piperidinesulfonyl group or a morpholinesulfonyl group,
$R^3$ is a hydrogen atom, an acetyl group, a benzoyl group or a pivaloyl group, and
$R^4$ is a hydrogen atom or a halogen atom] or an isotope thereof or a pharmaceutically acceptable salt thereof.

Another embodiment of the present invention is a compound represented by the general formula (II):

[Chemical 4]

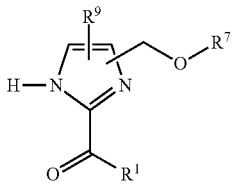
(II)

[wherein,
$R^1$ is a methyl group which may be substituted with the same or different 1 to 3 halogen atoms,
$R^7$ is a hydrogen atom or —C(O)—$R^8$,
$R^8$ is a C1-C8 alkyl group, a C3-C8 cycloalkyl group, a phenyl group, a pyridyl group, a naphthyl group, an amino group, a pyrrolidinyl group, a piperidinyl group or a morpholinyl group which may have the same or different 1 to 3 substituents selected from substituent group α,
the substituent group α is the group consisting of a halogen atom, a hydroxy group, a C1-C8 alkyl group, a C3-C8 cycloalkyl group, a C1-C8 alkoxy group, a C3-C8 cycloalkoxy group, an amino group, a mono or di(C1-C8 alkyl)amino group, a carboxyl group, a C1-C8 alkoxycarbonyl group, a phenyl group, a pyridyl group, a phenoxy group, a phenyl C1-C6 alkoxy group, a tert-butyloxycarbonylpiperidinyl group, a (2-acetyl-1H-imidazol-4-yl)methyloxycarbonyl group, a (2-acetyl-3H-imidazol-4-yl)methyloxycarbonyl group and an oxocyclopentylmethylphenyl group,
$R^9$ is a hydrogen atom, a halogen atom or a C1-C6 alkyl group] or an isotope thereof or a pharmaceutically acceptable salt thereof.

In the present description, "halogen atom" refers to a fluorine atom, a chlorine atom, a bromine atom or an iodine atom.

In the present description, "methyl group which may be substituted with the same or different 1 to 3 halogen atoms" refers to a group in which 1 to 3 hydrogen atoms in a methyl group may be substituted with the above same or different "halogen atoms".

In the present description, "C1-C6 alkyl group" refers to a linear or branched alkyl group with 1 to 6 carbon atoms. Specific examples include a methyl group, an ethyl group, a propyl group, an isopropyl group, a butyl group, an isobutyl group, a sec-butyl group, a tert-butyl group, a pentyl group, a 1,2-dimethyl-propyl group, an isopentyl group, a hexyl group, an isohexyl group, and the like.

In the present description, "C1-C8 alkyl group" refers to a linear or branched alkyl group with 1 to 8 carbon atoms. Specific examples include, in addition to the groups exemplified in the above "C1-C6 alkyl group", a heptyl group, an octyl group, and the like.

In the present description, "C1-C6 alkyl group which may be substituted with the same or different 1 to 3 halogen atoms" refers to a group in which 1 to 3 hydrogen atoms in the above "C1-C6 alkyl group" may be substituted with the above same or different "halogen atoms". Specific examples include a fluoromethyl group, a difluoromethyl group, a dichloromethyl group, a dibromomethyl group, a trifluoromethyl group, a trichloromethyl group, a 2-fluoroethyl group, a 2-chloroethyl group, a 2-bromoethyl group, a 2-iodoethyl group, a 2,2-dibromoethyl group, a 2,2,2-trifluoroethyl group, a 2,2,2-trichloroethyl group, a 3-chloropropyl group, a 4-fluorobutyl group, a 6-iodohexyl group, and the like.

In the present description, "C3-C6 cycloalkyl group" refers to a cyclopropyl group, a cyclobutyl group, a cyclopentyl group or a cyclohexyl group.

In the present description, "C3-C8 cycloalkyl group" refers to the above "C3-C6 cycloalkyl group", a cycloheptyl group or a cyclooctyl group.

In the present description, "C1-C6 alkoxy group" refers to a group in which the above "C1-C6 alkyl group" is bonded to an oxygen atom. Specific examples include a methoxy group, an ethoxy group, a propoxy group, a butoxy group, a pentyloxy group, a hexyloxy group, and the like.

In the present description, "C1-C8 alkoxy group" refers to a group in which the above "C1-C8 alkyl group" is bonded to an oxygen atom. Specific examples include, in addition to the groups exemplified in the above "C1-C6 alkoxy group", a heptyloxy group, an octyloxy group, and the like.

In the present description, "C1-C6 alkoxy C1-C6 alkyl group" refers to a group in which the above "C1-C6 alkoxy group" is bonded to the above "C1-C6 alkyl group". Specific examples include a methoxymethyl group, a methoxyethyl group, an ethoxymethyl group, a propoxymethyl group, a butoxymethyl group, a pentyloxymethyl group, a hexyloxymethyl group, and the like.

In the present description, "C1-C8 alkoxycarbonyl group" refers to a group in which the above "C1-C8 alkoxy group" is bonded to a carbonyl group. Specific examples include a methoxycarbonyl group, an ethoxycarbonyl group, a propoxycarbonyl group, a butoxycarbonyl group, a tert-butoxycarbonyl group, a heptyloxycarbonyl group, and the like.

In the present description, "C3-C6 cycloalkoxy group" refers to a cyclopropyloxy group, a cyclobutyloxy group, a cyclopentyloxy group or a cyclohexyloxy group.

In the present description, "C3-C8 cycloalkoxy group" refers to the above "C3-C6 cycloalkoxy group", a cycloheptyloxy group or a cyclooctyloxy group.

In the present description, "C3-C6 cycloalkoxy C1-C6 alkyl group" refers to a group in which the above "C3-C6 cycloalkoxy group" is bonded to the above "C1-C6 alkyl group". Specific examples include a cyclopropyloxymethyl group, a cyclobutyloxymethyl group, a cyclopentyloxymethyl group, a cyclohexyloxymethyl group, a cyclopropyloxyethyl group, a cyclohexyloxybutyl group, and the like.

In the present description, "C2-C6 alkenyl group" refers to a linear or branched alkenyl group with 2 to 6 carbon atoms, for example, a vinyl group, a 1-propenyl group, a 2-propenyl group, an isopropenyl group, a 1-butenyl group, a 2-butenyl group, a 1-pentenyl group, a 1-hexenyl group, and the like.

In the present description, "mono or di(C1-C6 alkyl)amino group" refers to a group in which one or two "C1-C6 alkyl group" mentioned above is bonded to an amino group, and examples include a dimethylamino group, a diethylamino group, an N-ethyl-N-methylamino group, a dipropylamino group, a dibutylamino group, a dipentylamino group, a dihexylamino group, and the like.

In the present description, "pharmaceutically acceptable salt" refers to a salt formed by reacting the compound of the present invention with an acid or a base.

The examples of the salt include hydrogen halide acid salts such as hydrofluorides, hydrochlorides, hydrobromides or hydroiodides; inorganic acid salts such as hydrochlorides, nitrates, perchlorates, sulfates or phosphates; lower alkanesulfonates such as methanesulfonates, trifluoromethanesulfonates or ethanesulfonates; aryl sulfonates such as benzenesulfonates or p-toluenesulfonates; organic acid salts such as acetates, malates, fumarates, succinates, citrates, ascorbates, tartrates, oxalates or maleates; alkali metal salts such as sodium salts, potassium salts or lithium salts; alkaline earth metal salts such as calcium salts or magnesium salts; metal salts such as aluminum salts or iron salts; inorganic salts such as ammonium salts; amine salts such as organic salts, e.g., t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts or tris(hydroxymethyl)aminomethane salts; and amino acid salts such as glycine salts, lysine salts, arginine salts, ornithine salts, glutamates or aspartates.

For example, by being left in the air, the compound of the present invention may absorb moisture or have adsorbed water adhered thereto so as to be a hydrate, which hydrate is also included in the salt of the present invention.

In cases where the compound of the present invention has asymmetric carbon atoms in its molecule, optical isomers are present. All of these isomers, and mixtures of these isomers are represented by a single formula, i.e., the general formula (I) or (II). Accordingly, the compound of the present invention includes all optical isomers as well as mixtures of optical isomers in an arbitrary ratio.

When, in the compound of the present invention, a tautomer of an imidazole ring is present, all of the respective tautomers and their mixtures in an arbitrary ratio are included therein.

The present invention may also include a compound in which one or more atoms constituting the compound of the present invention are substituted with isotopes of the atoms. There are two types of isotopes: radioactive isotopes and stable isotopes, and examples of isotopes include, for example, hydrogen isotope ($^2$H and $^3$H), carbon isotope ($^{11}$C, $^{13}$C and $^{14}$C), nitrogen isotope ($^{13}$N and $^{15}$N), oxygen isotope ($^{15}$O, $^{17}$O and $^{18}$O), fluorine isotope ($^{18}$F), and the like. A composition containing a compound labeled with isotope is useful as, for example, a therapeutic agent, a preventive agent, a research reagent, an assay reagent, a diagnostic agent, an in vivo diagnostic imaging agent, and the like. The compound labeled with isotope is also included in the compound of the present invention, and all the mixtures of the compounds labeled with isotope in an arbitrary ratio are also included in the compound of the present invention. Further, the compound of the present invention labeled with isotope can be produced with a method known in this field, for example, using a raw material labeled with isotope instead of a raw material in the production process of the present invention described later.

The present invention may also include a prodrug of the compound of the present invention. A prodrug, a derivative of the compound of the present invention, refers to a compound which is converted to the compound of the present invention enzymatically or chemically in vivo.

Examples of prodrugs of the compound of the present invention include a compound in which a hydroxy group in the molecule is acylated, alkylated, phosphorylated, etc. (see, e.g., Povl Krogsgaard-Larsen et al., "A Text Book of Drug Design and Development", 2nd ed., harwood academic publishers, 1996, pp. 351-385). Such prodrugs may be produced from the compound of the present invention by methods known in this field.

$R^1$ is preferably a methyl group which may be substituted with one to three fluorine atoms, and more preferably a methyl group or a difluoromethyl group.

$R^2$ is preferably a C2-C6 alkyl group, a cyclopropyl group, a C1-C2 alkoxy C1-C3 alkyl group, a cyclohexyloxymethyl group, a vinyl group, a furanylmethyl group, an oxetanyl group or a dimethylaminosulfonyl group, more preferably an ethyl group, a propyl group, a sec-butyl group, a tert-butyl group, a pentyl group, a hexyl group, a cyclopropyl group, a methoxymethyl group, a methoxyethyl group, a methoxyisopropyl group, an ethoxymethyl group, a cyclohexyloxymethyl group, a vinyl group, a furanylmethyl group, an oxetanyl group or a dimethylaminosulfonyl group, and even more preferably an ethyl group or vinyl group.

$R^3$ is preferably a hydrogen atom.

$R^4$ is preferably a hydrogen atom or a fluorine atom, and more preferably a hydrogen atom.

$R^7$ is preferably a hydrogen atom.

$R^9$ is preferably a hydrogen atom.

A preferred combination of $R^1$, $R^2$, $R^3$ and $R^4$ in the general formula (I) is a combination in which $R^1$ is a methyl group which may be substituted with one to three fluorine atoms, $R^2$ is a C2-C6 alkyl group, a cyclopropyl group, a C1-C2 alkoxy C1-C3 alkyl group, a cyclohexyloxymethyl group, a vinyl group, a furanylmethyl group, an oxetanyl group or a dimethylaminosulfonyl group, $R^3$ is a hydrogen atom, and $R^4$ is a hydrogen atom or a fluorine atom.

A more preferred combination is a combination in which $R^1$ is a methyl group or a difluoromethyl group, $R^2$ is an ethyl group, a propyl group, a sec-butyl group, a tert-butyl group, a pentyl group, a hexyl group, a cyclopropyl group, a methoxymethyl group, a methoxyethyl group, a methoxyisopropyl group, an ethoxymethyl group, a cyclohexyloxymethyl group, a vinyl group, a furanylmethyl group, an oxetanyl group or a dimethylaminosulfonyl group, $R^3$ is a hydrogen atom, and $R^4$ is a hydrogen atom.

A preferred combination of $R^1$, $R^7$ and $R^9$ in the general formula (II) is a combination in which $R^1$ is a methyl group which may be substituted with one to three fluorine atoms, $R^7$ is a hydrogen atom, and $R^9$ is a hydrogen atom. A more preferred combination is a combination in which $R^1$ is a methyl group or a difluoromethyl group, and $R^7$ and $R^9$ are both hydrogen atoms.

The compound of the present invention can be produced, for example, by the following process.

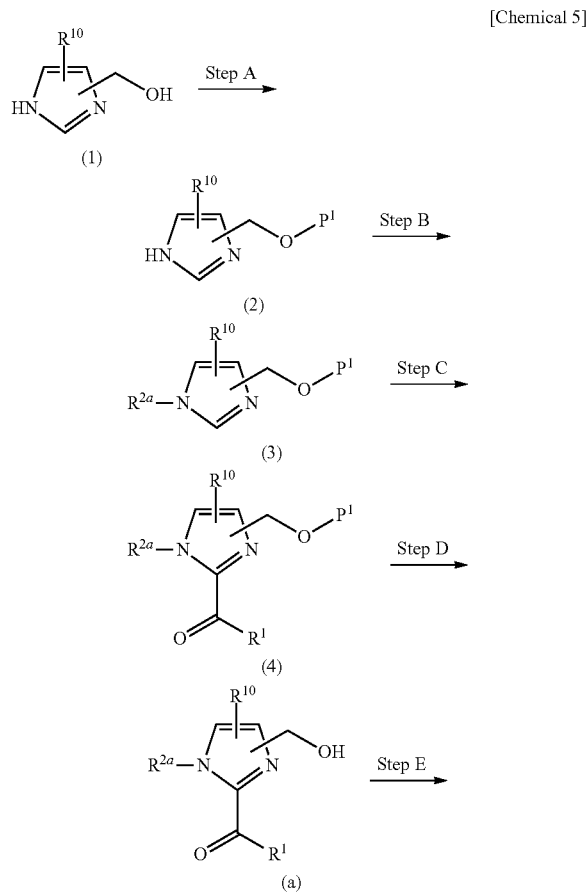

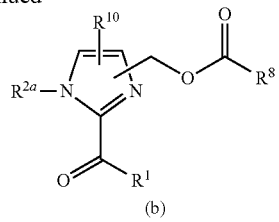

[wherein, $P^1$ is a protecting group, $R^{2a}$ is a hydrogen atom or $R^2$, $R^{10}$ is $R^4$ or $R^9$, and $R^1$, $R^2$, $R^4$, $R^8$ and $R^9$ are as defined above]

Examples of the protecting group $P^1$ include a tetrahydropyranyl group, a paramethoxybenzyl group, a benzyl group, silylether protecting groups such as a tert-butyldiphenylsilyl group, alkoxymethylether protecting groups such as a methoxymethyl group, and the like, with, inter alia, a silylether protecting group being preferred.

The following provides a description of each step.

Step A is a step for protecting the primary hydroxyl group of compound (1) or salts thereof (e.g., hydrochloride) which is commercially available or can be produced by a method known in this technical field (e.g., Journal of the Chemical Society, Perkin Transactions 1: Organic and Bio-organic Chemistry, 10, 2310-2315, 1980) with a protecting group $P^1$ to produce compound (2). Introduction reaction of a protecting group can be conducted in accordance with an ordinary method such as the one described in T. H. Greene, P. G. Wuts, Protective Groups in Organic Synthesis, Fourth Edition, 2007, John Wiley & Sons, Inc.

Step B is a step for allowing commercially available $R^{2a}$—X (wherein X is a leaving group such as a halogen atom, a methanesulfonyloxy group, a p-toluenesulfonyloxy group, or a trifluoromethanesulfonyloxy group) to act on compound (2) in a reaction solution in the presence of a base, and introducing the $R^{2a}$ group onto a nitrogen atom on the imidazol ring of the compound (2) to produce compound (3).

The reaction temperature is within the range of −78° C. to the boiling point of the solvent, with the range of 0 to 130° C. being preferred. The reaction time is usually about 1 to 24 hours. Further, the amount of $R^{2a}$—X to be used is usually within the range of 1 to 10 equivalents per 1 equivalent of the compound (1), with the range of 1 to 2 equivalents being preferred.

Examples of the reaction solvent can include hydrocarbon solvents such as hexane and toluene, halogenated hydrocarbon solvents such as dichloromethane and chloroform, ether solvents such as diethylether, tetrahydrofuran (hereinafter, also referred to as THF) and 1,4-dioxane, ester solvents such as ethyl acetate, and aprotic polar solvents such as acetonitrile, N,N-dimethylformamide (hereinafter, also referred to as DMF) and dimethyl sulfoxide (hereinafter, also referred to as DMSO).

Examples of the base can include organic amine bases such as triethylamine (hereinafter, also referred to as TEA), diisopropylethylamine (hereinafter, also referred to as DIEA), N-methylmorpholine, pyridine and 4-(N,N-dimethylamino) pyridine (hereinafter, also referred to as DMAP), inorganic bases such as sodium hydride, potassium carbonate and cesium carbonate, and organic lithium reagents such as n-butyl lithium, sec-butyl lithium and lithium diisopropylamide (hereinafter, also referred to as LDA). The amount of the above base to be used is usually within the range of 1 to 10 equivalents per 1 equivalent of the compound (1), with the range of 1 to 2 equivalents being preferred. Further, when using a salt of the compound (1), it is preferable to use the above base in a stoichiometrically equivalent amount or more in addition to the above-mentioned equivalents thereof in order to neutralize the salt.

A compound (3a) in which $R^{10}$ in the compound (3) is a hydrogen atom can also be produced by the following process.

[Chemical 6]

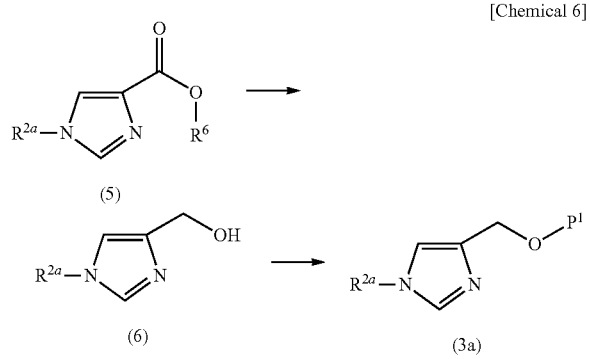

[wherein, $R^6$ is a C1-C6 alkyl group, and $P^1$ and $R^{ea}$ are as defined above]

Compound (5) which is commercially available or can be produced by a method known in this technical field (e.g., Organic Letters, 4, 4133-4134, 2002) is subjected to a reduction reaction to produce compound (6). Then, analogously to Step A, a protecting group $P^1$ can be introduced to produce compound (3a). The above reduction reaction can be conducted referring to Experimental Chemistry (see 4th ed., Vol. 26, Chemical Society of Japan, Maruzen Publishing, "Organic Synthesis III: asymmetric synthesis/reduction/sugar/labeled compound, pp. 185-245").

Step C is a step for reacting the compound (3) with $R^1CO$—Y (wherein Y is a halogen atom, a N-methoxy-N-methylamino group, a 1-pyrrolidinyl group or a lower alkoxy group, and $R^1$ is as defined above) or $(R^1CO)_2O$ which is commercially available or can be produced by a method known in this technical field (e.g., Tetrahedron Letters, 48, 377-380, 2006) in a reaction solvent in the presence of a base, and introducing an acyl group to produce compound (4).

The reaction temperature is within the range of −78° C. to room temperature, with the range of −78 to 0° C. being preferred. The reaction time is usually about 0.5 hours to 12 hours. Further, the amount of $R^1CO$—Y or $(R^1CO)_2O$ to be used is usually within the range of 1 to 10 equivalents per 1 equivalent of the compound (3), with the range of 1 to 2 equivalents being preferred.

Examples of the reaction solvent can include hydrocarbon solvents such as hexane and toluene, halogenated hydrocarbon solvents such as dichloromethane and chloroform, ether solvents such as diethylether, THF and 1,4-dioxane, and aprotic polar solvents such as acetonitrile, DMF and DMSO.

Examples of the base can include organic amine bases such as TEA, DIEA, N-methylmorpholine, pyridine and DMAP, and organic lithium reagents such as n-butyl lithium, sec-butyl lithium and LDA. The amount of the base to be used is usually within the range of 1 to 10 equivalents per 1 equivalent of the compound (3), with the range of 1 to 2 equivalents being preferred. Further, when using an organic lithium reagent as a base, it is preferable to use a hydrocarbon solvent or an ether solvent as the above reaction solvent.

Step D is a step for deprotecting protecting group $P^1$ of the compound (4) to produce a compound (a) in which $R^3$ in the general formula (I) or $R^7$ in the general formula (II) is a hydrogen atom. The deprotection reaction can be conducted in accordance with an ordinary method such as the one described in T. H. Greene, P. G. Wuts, Protective Groups in Organic Synthesis, Fourth Edition, 2007, John Wiley & Sons, Inc.

Step E is a step for reacting the compound (a) with commercially available $R^8COX$ or $(R^8CO)_2O$ (wherein $R^8$ and X are as defined above) in a reaction solvent in the presence of a base, and forming an ester bond to produce a compound (b) in which $R^3$ in the general formula (I) is an acetyl group, a benzoyl group or a pivaloyl group, or wherein $R^7$ in the general formula (II) is —C(O)—$R^8$.

The reaction temperature is within the range of −20° C. to the boiling point of the solvent, with the range of 0° C. to room temperature being preferred. The reaction time is usually about 0.5 to 24 hours. Further, the amount of $R^8COX$ or $(R^8CO)_2O$ to be used is usually within the range of 1 to 10 equivalents per 1 equivalent of the compound (a), with the range of 1 to 2 equivalents being preferred.

Examples of the reaction solvent can include hydrocarbon solvents such as hexane and toluene, halogenated hydrocarbon solvents such as dichloromethane and chloroform, ether solvents such as diethylether, THF and 1,4-dioxane, and aprotic polar solvents such as acetonitrile, DMF and DMSO.

Examples of the base can include organic amine bases such as TEA, DIEA, N-methylmorpholine, pyridine and DMAP. The amount of the base to be used is usually within the range of 1 to 10 equivalents per 1 equivalent of the compound (a), with the range of 1 to 2 equivalents being preferred.

The compound of the present invention produced by the above process can be isolated or purified by means of methods known in this technical field, for example, extraction, precipitation, fraction, chromatography, and the like.

The compound of the present invention can be easily produced from known compounds in accordance with the Reference Examples and Examples described later, other than using the above process for the production thereof.

The compound or isotope thereof or pharmaceutically acceptable salt thereof obtainable by the above process has excellent S1P lyase inhibitory capacity, and thus can suppress the activity of the immune system. Accordingly, the compound or isotope thereof or pharmaceutically acceptable salt thereof of the present invention can be used for preventing or treating inflammatory bowel disease (IBD) (e.g., ulcerative colitis, Crohn's disease, etc.), acute lung injury, autoimmune disease (e.g., rheumatoid arthritis, systemic lupus erythematosus, antiphospholipid antibody syndrome, multiple myositis, dermatomyositis, systemic scleroderma, Sjogren's syndrome, polyarteritis nodosa, microscopic polyarteritis, allergic granulomatous angiitis, Wegener's granulomatosis, mixed connective tissue disease, etc.), multiple sclerosis (MS), allergic disease (e.g., atopic dermatitis, allergic rhinitis (including pollinosis), allergic conjunctivitis, allergic gastroenteritis, bronchial asthma, infantile asthma, food allergy, drug allergy, urticaria, etc.), and the like, or can be used as an active ingredient of a pharmaceutical composition for suppressing rejection response against transplant.

The pharmaceutical composition containing as an active ingredient the compound or isotope thereof or pharmaceutically acceptable salt thereof of the present invention, when administered to a mammal (e.g., a human, horse, cow, pig, etc., preferably a human), may be administered systemically or locally, and orally or parenterally.

The pharmaceutical composition of the present invention can be prepared according to various preparation methods of formulations which are usually employed by selecting an appropriate form depending on the administration method.

Examples of forms of the pharmaceutical compositions for oral administration include tablets, pills, powders, granules, capsules, solutions, suspensions, emulsions, syrups, elixirs, and the like. For preparation of pharmaceutical compositions in such forms, excipients, binders, disintegrants, lubricants, swelling agents, swelling adjuvants, coating agents, plasticizers, stabilizers, antiseptics, antioxidants, colorants, dissolution aids, suspending agents, emulsifiers, sweeteners, preservatives, buffers, diluents, wetting agents, and the like which are usually employed as additives may be appropriately selected as needed, to allow the pharmaceutical compositions to be produced according to ordinary methods.

Examples of forms of the pharmaceutical compositions for parenteral administration include injection solutions, ointments, gels, creams, poultices, patches, nebulas, inhalants, sprays, eye drops, nose drops, suppositories, inhalants, and the like. For preparation of pharmaceutical compositions in such forms, stabilizing agents, antiseptics, dissolution aids, humectants, preservatives, antioxidants, flavoring agents, gelling agents, neutralizers, buffers, isotonic agents, surfactants, colorants, thickeners, wetting agents, fillers, absorption promoters, suspending agents, binders, and the like which are usually employed as additives may be appropriately selected as needed, to allow the pharmaceutical compositions to be produced according to ordinary methods.

While the dosage of the compound or isotope thereof or pharmaceutically acceptable salt thereof of the present invention varies depending on symptoms, age, body weight, or the like, in the case of oral administration, the dosage is 1 to 3000 mg, preferably 1 to 1000 mg, in terms of the amount of the compound, per dose once to several times a day for an adult, and in the case of parenteral administration, the dosage is 0.01 to 1500 mg, preferably 0.1 to 500 mg, in terms of the amount of the compound, per dose once to several times a day for an adult.

Although the following provides Reference Examples, Examples, Formulation Examples and Test Examples to explain the present invention in more detail, the scope of the present invention is not limited thereto.

EXAMPLES

Example 1

1-(1-Ethoxymethyl-4-hydroxymethyl-1H-imidazol-2-yl)ethanone (1) 1-Ethoxymethyl-1H-imidazole-4-carboxylic acid methylester

[Chemical 7]

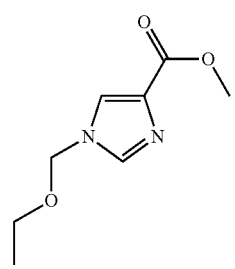

Imidazole-4(5)-carboxylic acid methyl ester (3.00 g) was dissolved in acetonitrile (100 mL), and at room temperature TEA (6.63 mL) and then chloromethylethylether (3.28 mL) were added, followed by heating to reflux for 10 hours. After being allowed to cool to room temperature, the mixture was diluted with water, and extracted with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=10%→100%) using silica gel column (product name: SNAP Cartridge KP-Sil 50 g, manufactured by Biotage, Ltd.) to afford the title compound (2.67 g).

$^1$H-NMR (CDCl$_3$) δ: 1.20 (3H, t, J=7.1 Hz), 3.48 (2H, q, J=7.1 Hz), 3.91 (3H, s), 5.31 (2H, s), 7.62 (1H, d, J=1.2 Hz), 7.74 (1H, d, J=1.2 Hz).

(2) 1-Ethoxymethyl-1H-imidazole-4-methanol

[Chemical 8]

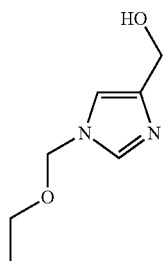

To THF (200 mL) was added lithium aluminum hydride (3.85 g), and, with stirring under ice cooling, a THF (150 mL) solution of the resulting compound (39.4 g) obtained in (1) was added dropwise over 30 minutes, followed by stirring at the same temperature for 30 minutes. To the reaction mixture, at the same temperature, were added dropwise water (3.85 mL), a 15% aqueous sodium hydroxide solution (3.85 mL) and water (11.6 mL) in this order, and stirring was continued for 10 hours while the temperature was gradually brought back to room temperature. The resulting solid material was removed by Celite filtration, and the solvent of the filtrate was distilled off under reduced pressure to afford the title compound (21.0 g).

$^1$H-NMR (CDCl$_3$) δ: 1.19 (3H, t, J=7.1 Hz), 3.46 (2H, q, J=7.1 Hz), 4.62 (2H, s), 5.25 (2H, s), 7.00 (1H, s), 7.56 (1H, d, J=1.2 Hz).

(3) 1-Ethoxymethyl-4-(triethylsilyloxymethyl)-1H-imidazole

[Chemical 9]

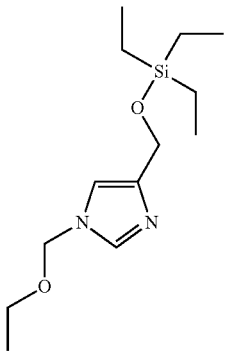

The compound (520 mg) obtained in (2) was dissolved in dichloromethane (30 mL), followed by addition of triethylsilyl chloride (1.12 mL), TEA (1.16 mL) and DMAP (catalytic amount) under stirring, and the stirring was continued for 17 hours. The reaction solution was diluted with water, and extracted with chloroform. The combined extract was washed with saturated brine, dried over anhydrous sodium sulfate, and subsequently the solvent was distilled off under reduced pressure. The resulting residue was purified by flash chromatography (ethyl acetate/hexane=10%→80%) using silica gel column (product name: SNAP Cartridge KP-Sil 50 g, manufactured by Biotage, Ltd.) to afford the title compound (665 mg).

¹H-NMR (CDCl₃) δ: 0.63-0.68 (6H, m), 0.95-0.99 (9H, m), 1.18 (3H, t, J=7.1 Hz), 3.44 (2H, q, J=7.1 Hz), 4.69 (2H, d, J=1.2 Hz), 5.23 (2H, s), 6.98 (1H, d, J=1.2 Hz), 7.51 (1H, d, J=1.2 Hz).

(4) 1-[1-Ethoxymethyl-4-(triethylsilyloxymethyl)-1H-imidazol-2-yl]ethanone

[Chemical 10]

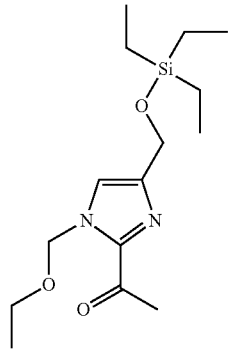

The compound (665 mg) obtained in (3) was dissolved in THF (20 mL), and cooled to −78° C. while stirring under an argon atmosphere. To the present solution was added dropwise n-butyl lithium (2.69 M hexane solution, 1.50 mL) slowly using a syringe, followed by stirring at the same temperature for 30 minutes. Then, N-methoxy-N-methylacetamide (0.50 mL) was added using a syringe, and stirring was continued for 17 hours while the temperature was raised to room temperature. A saturated aqueous ammonium chloride solution was added to the reaction solution to terminate the reaction, followed by extraction with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=5%→30%) using silica gel column (product name: SNAP Cartridge KP-Sil 50 g, manufactured by Biotage, Ltd.) to afford the title compound (520 mg).

¹H-NMR (CDCl₃) δ: 0.62-0.69 (6H, m), 0.96-1.01 (9H, m), 1.19 (3H, t, J=6.9 Hz), 2.64 (3H, s), 3.53 (2H, q, J=6.9 Hz), 4.73 (2H, s), 5.76 (2H, s), 7.24 (1H, s).

(5) 1-(1-Ethoxymethyl-4-hydroxymethyl-1H-imidazol-2-yl)ethanone

[Chemical 11]

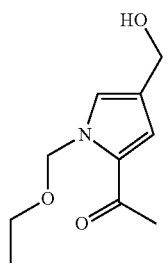

The compound (520 mg) obtained in (4) was dissolved in THF (10 mL), followed by addition of tetrabutylammonium fluoride (TBAF, 1.0 M THF solution, 3.32 mL) under stirring, and the stirring was continued for 1 hour. The reaction solution was concentrated under reduced pressure, and the resulting residue was purified by flash chromatography (ethyl acetate/hexane=25%→100%) using amino column (product name: SNAP Cartridge KP-NH 55 g, manufactured by Biotage, Ltd.) to afford the title compound (288 mg).

¹H-NMR (DMSO-D₆) δ: 1.07 (3H, t, J=6.9 Hz), 2.53 (3H, s), 3.46 (2H, q, J=7.0 Hz), 4.41 (2H, d, J=5.7 Hz), 5.11 (1H, t, J=5.7 Hz), 5.67 (2H, s), 7.49 (1H, s).

Anal. Calcd for C₉H₁₄N₂O₃: C, 54.53; H, 7.12; N, 14.13. Found: C, 54.46; H, 7.06; N, 14.12.

Example 2

1-(4-Hydroxymethyl-1H-imidazol-2-yl)ethanone and 1-(5-hydroxymethyl-1H-imidazol-2-yl)ethanone

[Chemical 12]

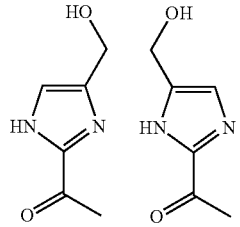

The compound (4.95 g) obtained in Example 1 was dissolved in 1 N hydrochloric acid (180 mL), and stirring was continued for 30 hours while the mixture was warmed to 70° C. A 1 N aqueous sodium hydroxide solution was added to the reaction solution for neutralization, and subsequently the solvent was distilled off under reduced pressure. The resulting residue was purified by flash chromatography (methanol/chloroform=0%→10%) using silica gel column (product name: SNAP Cartridge KP-Sil 100 g, manufactured by Biotage, Ltd.) to afford the mixture (3.30 g) of the title compound.

¹H-NMR (CD₃OD) δ: 2.54 (3H, s), 4.59 (2H, s), 7.11-7.27 (1H, m).

MS (FAB) m/z: 141 [(M+H)⁺].

Anal. Calcd for C₆H₈N₂O₂: C, 51.42; H, 5.75; N, 19.99. Found: C, 51.59; H, 5.81; N, 19.90.

Example 3

Benzoic acid (2-acetyl-1H-imidazol-4-yl)methylester and benzoic acid (2-acetyl-3H-imidazol-4-yl)methylester

[Chemical 13]

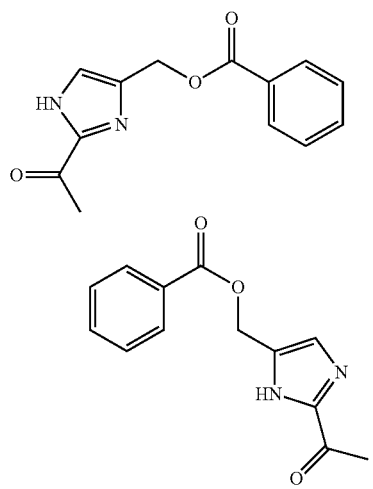

The mixture (200 mg) obtained in Example 2 was suspended in chloroform (10 mL), followed by addition of benzoyl chloride (0.197 mL) and TEA (0.398 mL) under ice cooling, and the stirring was continued at the same temperature for 3 hours. The reaction solution was diluted with dichloromethane, washed with saturated brine, and subsequently dried over anhydrous sodium sulfate to distill off the solvent under reduced pressure. The resulting residue was purified by flash chromatography (methanol/chloroform=0%→5%) using silica gel column (product name: Hi-Flash Column 2 L, manufactured by Yamazen Corporation) to afford the mixture (320 mg) of the title compound.

$^1$H-NMR (CD$_3$OD) δ: 2.57 (3H, s), 5.34 (2H, s), 7.43-7.49 (3H, m), 7.57-7.62 (1H, m), 8.04-7.99 (2H, m).

MS (ESI) m/z: 245 [(M+H)$^+$].

Example 4

Acetic acid (2-acetyl-1H-imidazol-4-yl)methylester and acetic acid (2-acetyl-3H-imidazol-4-yl)methylester

[Chemical 14]

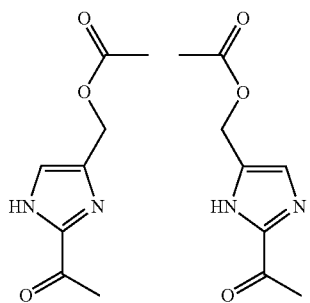

The mixture (200 mg) obtained in Example 2 was suspended in dichloromethane (10 mL), followed by addition of acetic anhydride (0.202 mL) and TEA (0.398 mL), and stirring was continued at room temperature for 7 hours. The reaction solution was concentrated under reduced pressure, and the resulting residue was purified by flash chromatography (methanol/chloroform=0%→5%) using silica gel column (product name: Hi-Flash Column 2 L, manufactured by Yamazen Corporation) to afford the mixture (260 mg) of the title compound.

$^1$H-NMR (CD$_3$OD) δ: 2.05 (3H, s), 2.55 (3H, s), 5.08 (2H, s), 7.32 (1H, br s).

MS (ESI) m/z: 183 [(M+H)$^+$].

Example 5

1-(4-Hydroxymethyl-1-methoxymethyl-1H-imidazol-2-yl)ethanone (1) 1-Methoxymethyl-1H-imidazole-4-carboxylic acid ethyl ester

[Chemical 15]

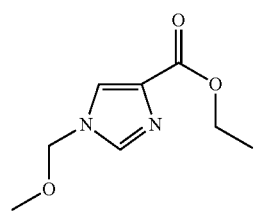

In analogy to Step (1) of Example 1, but using ethyl imidazole-4-carboxylate (26.3 g) and chloromethylmethylether (21.2 mL), the title compound (17.2 g) was afforded.

$^1$H-NMR (CDCl$_3$) δ: 1.39 (3H, t, J=7.2 Hz), 3.31 (3H, s), 4.38 (2H, q, J=7.4 Hz), 5.25 (2H, s), 7.62-7.63 (1H, m), 7.72-7.73 (1H, m).

MS (ESI) m/z: 185 [(M+H)$^+$].

(2) 1-Methoxymethyl-1H-imidazole-4-methanol

[Chemical 16]

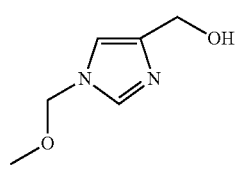

In analogy to Step (2) of Example 1, but using the compound (17.2 g) obtained in (1), the title compound (8.81 g) was afforded.

$^1$H-NMR (CDCl$_3$) δ: 3.28 (3H, s), 4.62 (2H, s), 5.20 (2H, s), 7.00 (1H, br s), 7.56-7.57 (1H, m).

(3) 4-(tert-Butyldiphenylsilyloxymethyl)-1-methoxymethyl-1H-imidazole

[Chemical 17]

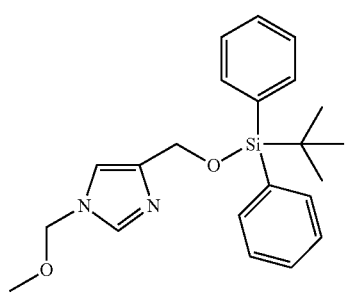

The compound (8.81 g) obtained in (2) was dissolved in dichloromethane (100 mL), followed by addition of tert-butyldiphenylsilyl chloride (hereinafter, also referred to as TBDPSCl) (24.3 mL), DIEA (21.6 mL) and DMAP (0.760 g) under stirring, and the stirring was continued for 1 day. The reaction solution was concentrated, and the resulting residue was purified by flash chromatography (ethyl acetate/hexane=50%→100%) using silica gel column (product name: Hi-Flash Column 4 L, manufactured by Yamazen Corporation) to afford the title compound (16.9 g).

$^1$H-NMR (CDCl$_3$) δ: 1.08 (9H, s), 3.26 (3H, s), 4.75 (2H, d, J=0.9 Hz), 5.19 (2H, s), 6.92-6.93 (1H, m), 7.34-7.44 (6H, m), 7.51-7.52 (1H, m), 7.73-7.68 (4H, m).

MS (ESI) m/z: 381 [(M+H)$^+$].

(4) 1-[4-(tert-Butyldiphenylsilyloxymethyl)-1-methoxymethyl-1H-imidazol-2-yl]ethanone

[Chemical 18]

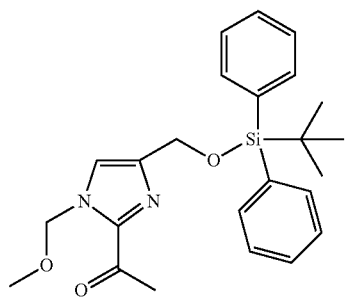

In analogy to Step (4) of Example 1, but using the compound (1.00 g) obtained in (3), the title compound (0.875 g) was afforded.

¹H-NMR (CDCl₃) δ: 1.09 (9H, s), 2.62 (3H, s), 3.33 (3H, s), 4.77 (2H, s), 5.69 (2H, s), 7.14 (1H, s), 7.45-7.34 (6H, m), 7.71-7.66 (4H, m).

MS (ESI) m/z: 423 [(M+H)⁺].

(5) 1-(4-Hydroxymethyl-1-methoxymethyl-1H-imidazol-2-yl)ethanone

[Chemical 19]

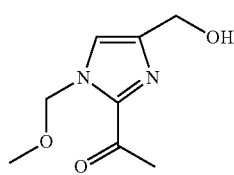

In analogy to Step (5) of Example 1, but using the compound (10.47 g) obtained in (4), the title compound (3.71 g) was afforded.

¹H-NMR (CDCl₃) δ: 2.23 (1H, br s), 2.67 (3H, s), 3.36 (3H, s), 4.68 (2H, s), 5.71 (2H, s), 7.24 (1H, s).

MS (ESI) m/z: 185 [(M+H)⁺].

Anal. Calcd for $C_8H_{12}N_2O_3$: C, 52.17; H, 6.57; N, 15.21. Found: C, 52.08; H, 6.57; N, 15.34.

Example 6

2-Acetyl-4-hydroxymethylimidazole-1-sulfonic acid dimethylamide (1) 4-(tert-Butyldiphenylsilyloxymethyl)imidazole-1-sulfonic acid dimethylamide and 5-(tert-butyldiphenylsilyloxymethyl)imidazole-1-sulfonic acid dimethylamide

[Chemical 20]

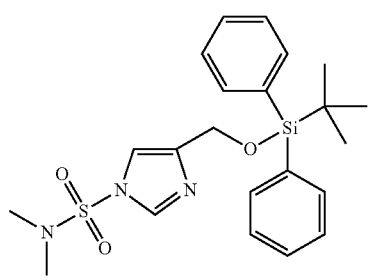

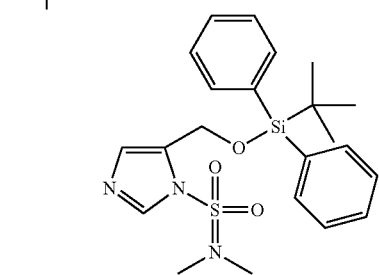

4(5)-(tert-Butyldiphenylsilyloxymethyl)-1H-imidazole (5.00 g) was dissolved in dichloromethane (50 mL), and under ice cooling and stirring TEA (4.14 mL) and dimethylsulfamoyl chloride (2.47 mL) were added, followed by stirring at room temperature for 20 hours. The reaction solution was diluted with ethyl acetate, washed with saturated brine, and subsequently dried over anhydrous magnesium sulfate to distill off the solvent under reduced pressure. The resulting residue was purified by flash chromatography (ethyl acetate/hexane=25%→50%) using silica gel column (product name: Hi-Flash Column 4 L, manufactured by Yamazen Corporation) to afford 4-(tert-butyldiphenylsilyloxymethyl)imidazole-1-sulfonic acid dimethylamide (4.59 g) as a low polar fraction and 5-(tert-butyldiphenylsilyloxymethyl)imidazole-1-sulfonic acid dimethylamide (1.55 g) as a high polar fraction.

4-(tert-Butyldiphenylsilyloxymethyl)imidazole-1-sulfonic acid dimethylamide

¹H-NMR (CDCl₃) δ: 1.08 (9H, s), 2.82 (6H, s), 4.74 (2H, d, J=0.9 Hz), 7.09 (1H, d, J=0.9 Hz), 7.45-7.35 (6H, m), 7.70-7.66 (4H, m), 7.82 (1H, d, J=1.8 Hz).

MS (ESI) m/z: 444 [(M+H)⁺].

5-(tert-Butyldiphenylsilyloxymethyl)imidazole-1-sulfonic acid dimethylamide:

¹H-NMR (CDCl₃) δ: 1.07 (9H, s), 2.75 (6H, s), 4.82 (2H, d, J=0.9 Hz), 7.01-7.02 (1H, m), 7.37-7.47 (6H, m), 7.66-7.70 (4H, m), 7.86-7.84 (1H, m).

MS (ESI) m/z: 444 [(M+H)⁺].

(2) 2-Acetyl-4-(tert-butyldiphenylsilyloxymethyl)imidazole-1-sulfonic acid dimethylamide

[Chemical 21]

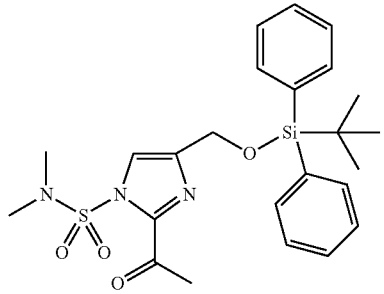

In analogy to Step (4) of Example 1, but using 4-(tert-butyldiphenylsilyloxymethyl)imidazole-1-sulfonic acid dimethylamide (2.00 g), the title compound (0.905 g) was afforded.

MS (ESI) m/z: 486 [(M+H)⁺].

(3) 2-Acetyl-4-hydroxymethylimidazole-1-sulfonic acid dimethylamide

[Chemical 22]

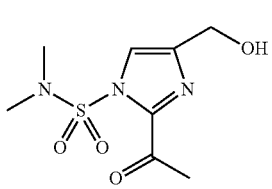

The compound (0.910 g) obtained in (2) was dissolved in THF (10 mL), followed by addition of TBAF (1.0 M THF solution, 4.08 mL) under stirring, and the stirring was continued for 21 hours. The reaction solution was diluted with ethyl acetate, washed with saturated brine, and subsequently dried over anhydrous magnesium sulfate to distill off the solvent under reduced pressure. The resulting residue was purified by flash chromatography (ethyl acetate/hexane=20%→100%) using amino column (product name: Hi-Flash Column 2 L, manufactured by Yamazen Corporation) to afford the title compound (0.170 g).

$^1$H-NMR (CD$_3$OD) δ: 2.59 (3H, s), 3.04 (6H, s), 4.54 (2H, s), 7.62 (1H, s).

MS (ESI) m/z: 248 [(M+H)$^+$].

Example 7

1-(4-Hydroxymethyl-1-isopropyl-1H-imidazol-2-yl)ethanone (1) 1-Isopropyl-1H-imidazole-4-carboxylic acid ethyl ester

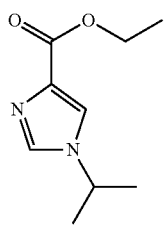

[Chemical 23]

Ethyl 3-(N,N-dimethylamino)-2-isocyanoacrylate (Org. Lett. 2002, 4, 4133, 5.00 g) and isopropylamine (12.3 mL) were heated at 70° C. for 22 hours while stirring. The temperature of the reaction solution was brought back to room temperature, and subsequently purified by flash chromatography (ethyl acetate/hexane=30%→100%) using amino column (product name: Hi-Flash Column 3 L, manufactured by Yamazen Corporation) to afford the title compound (4.75 g).

$^1$H-NMR (CDCl$_3$) δ: 1.39 (3H, t, J=7.4 Hz), 1.52 (6H, d, J=6.3 Hz), 4.33-4.41 (3H, m), 7.54 (1H, s), 7.66-7.68 (1H, m).

MS (ESI) m/z: 183 [(M+H)$^+$].

(2) 4-(tert-Butyldiphenylsilyloxymethyl)-1-isopropyl-1H-imidazole

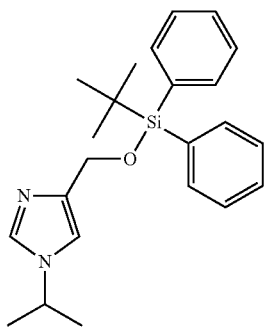

[Chemical 24]

Lithium aluminum hydride (2.97 g) was suspended in THF (100 mL), and a THF solution (50 mL) of the compound (4.75 g) obtained in (1) was added dropwise over 20 minutes under ice cooling. After completion of the dropwise addition, the reaction solution was stirred at the same temperature for 2 hours. To this reaction solution, under ice cooling, were added water (2.97 mL), a 1 N aqueous sodium hydroxide solution (2.97 mL) and water (11.9 mL), followed by stirring for a while. Further, to this reaction solution was added chloroform followed by stirring to obtain the suspension. The insolubles were filtered off, and the resulting mother liquor was concentrated to afford (1-isopropyl-1H-imidazol-4-yl)methanol, which was then subjected to the next reaction.

This (1-isopropyl-1H-imidazol-4-yl)methanol was dissolved in dichloroethane (200 mL), and at room temperature TEA (10.9 mL), TBDPSCl (10.2 mL) and DMAP (0.320 g) were added, followed by stirring for 17 hours. The reaction solution was poured into water, and extracted with dichloromethane. The extract was washed with saturated brine, dried over anhydrous sodium sulfate, and subsequently the solvent was distilled off under reduced pressure. The resulting residue was purified by flash chromatography (ethyl acetate/hexane=20%→100%) using silica gel column (product name: Hi-Flash Column 3 L, manufactured by Yamazen Corporation) to afford the title compound (9.11 g).

$^1$H-NMR (CDCl$_3$) δ: 1.07 (9H, s), 1.45 (6H, d, J=6.3 Hz), 4.22-4.31 (1H, m), 4.73 (2H, s), 6.78 (1H, d, J=1.1 Hz), 7.33-7.45 (7H, m), 7.73-7.69 (4H, m).

MS (ESI) m/z: 379 [(M+H)$^+$].

(3) 1-[4-(tert-Butyldiphenylsilyloxymethyl)-1-isopropyl-1H-imidazol-2-yl]ethanone

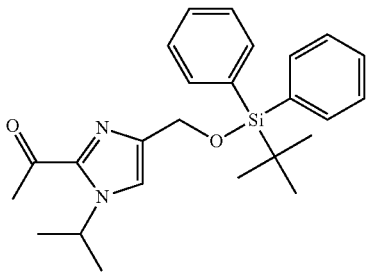

[Chemical 25]

In analogy to Step (4) of Example 1, but using the compound (5.40 g) obtained in (2), the title compound (3.98 g) was afforded.

$^1$H-NMR (CDCl$_3$) δ: 1.09 (9H, s), 1.38 (6H, d, J=7.4 Hz), 2.61 (3H, s), 4.76 (2H, s), 5.52-5.44 (1H, m), 7.05 (1H, s), 7.45-7.34 (6H, m), 7.71-7.67 (4H, m).

MS (ESI) m/z: 421 [(M+H)$^+$].

(4) 1-(4-Hydroxymethyl-1-isopropyl-1H-imidazol-2-yl)ethanone

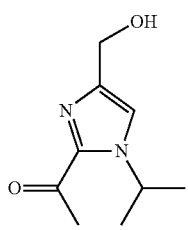

[Chemical 26]

In analogy to Step (5) of Example 1, but using the compound (3.98 g) obtained in (3), the title compound (1.31 g) was afforded.

¹H-NMR (CDCl₃) δ: 1.43 (6H, d, J=6.3 Hz), 2.12-2.07 (1H, m), 2.66 (3H, s), 4.66 (2H, d, J=5.7 Hz), 5.48-5.57 (1H, m), 7.23 (1H, s).

Anal. Calcd for $C_9H_{14}N_2O_2$: C, 59.32; H, 7.74; N, 15.37. Found: C, 59.23; H, 7.71; N, 15.43.

MS (ESI) m/z: 183 [(M+H)⁺].

Example 8

2,2-Difluoro-1-(1-ethoxymethyl-4-hydroxymethyl-1H-imidazol-2-yl)ethanone (1) 1-[4-(tert-Butyldiphenylsilyloxymethyl)-1-ethoxymethyl-1H-imidazol-2-yl]-2,2-difluoroethanone

[Chemical 27]

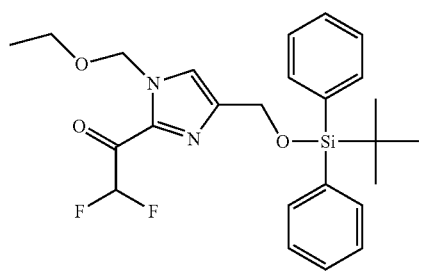

4-(tert-Butyldiphenylsilyloxymethyl)-1-ethoxymethyl-1H-imidazole (2.00 g) was dissolved in THF (10 mL), and was cooled to −78° C. while stirring under an argon atmosphere. To the present solution was added dropwise n-butyl lithium (2.69 M hexane solution, 3.18 mL) slowly using a syringe, followed by stirring at the same temperature for 30 minutes. Then, N-methoxy-N-methyl difluoroacetamide (1.41 g) was added using a syringe, and stirring was continued for 17 hours while the temperature was raised to room temperature. A saturated aqueous ammonium chloride solution was added to the reaction solution to terminate the reaction, followed by extraction with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=0%→20%) using silica gel column (product name: SNAP Cartridge KP-Sil 50 g, manufactured by Biotage, Ltd.) to afford the title compound (1.74 g).

¹H-NMR (CDCl₃) δ: 1.09 (9H, s), 1.21 (3H, t, J=7.1 Hz), 3.53 (2H, q, J=7.1 Hz), 4.78 (2H, s), 5.76 (2H, s), 6.85 (1H, t, J=53.8 Hz), 7.33 (1H, s), 7.36-7.47 (6H, m), 7.67-7.69 (4H, m).

(2) 2,2-Difluoro-1-(1-ethoxymethyl-4-hydroxymethyl-1H-imidazol-2-yl)ethanone

[Chemical 28]

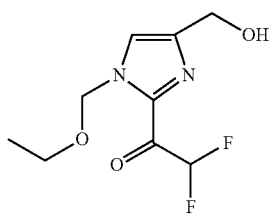

In analogy to Step (3) of Example 6, but using the compound (1.74 g) obtained in (1), the title compound (505 mg) was afforded.

¹H-NMR (CDCl₃) δ: 1.22 (3H, t, J=7.0 Hz), 2.06 (1H, t, J=5.4 Hz), 3.57 (2H, q, J=7.0 Hz), 4.71 (2H, d, J=5.7 Hz), 5.79 (2H, s), 6.92 (1H, t, J=53.8 Hz), 7.43 (1H, s).

MS (ESI) m/z: 235 (M+H)⁺.

Example 9

1-(4-Hydroxymethyl-1-vinyl-1H-imidazol-2-yl)ethanone (1) 1-(2-Fluoroethyl)-1H-imidazole-4-carbaldehyde

[Chemical 29]

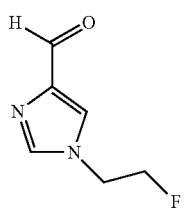

Imidazole-4(5)-carbaldehyde (20.0 g) was suspended in THF (400 mL), and at room temperature 60% sodium hydride (13.6 g) was added, followed by heating to reflux for 1.5 hours. The temperature of the reaction mixture was brought back to room temperature, and subsequently 2-fluoroethyl tosylate (J. Org. Chem., 2004, 69, 5934, 90.6 g) was added, followed by heating to reflux for a further 22 hours. The temperature of the reaction mixture was brought back to room temperature, which was subsequently poured into water, followed by extraction with ethyl acetate. The resulting aqueous layer was further extracted with a 10% methanol/chloroform solution. The combined extract was dried over anhydrous sodium sulfate, and subsequently the solvent was distilled off under reduced pressure. The resulting residue was purified by flash chromatography (methanol/chloroform=10%) using silica gel column (product name: Hi-Flash 5 L, manufactured by Yamazen Corporation) to afford the title compound (10.0 g).

¹H-NMR (CDCl₃) δ: 4.32 (2H, dt, J=27.1, 4.6 Hz), 4.71 (2H, dt, J=47.2, 4.6 Hz), 7.62 (1H, s), 7.71 (1H, s), 9.90 (1H, s).

MS (ESI) m/z: 143 [(M+H)⁺].

(2) 4-(tert-Butyldiphenylsilyloxymethyl)-1-(2-fluoroethyl)-1H-imidazole

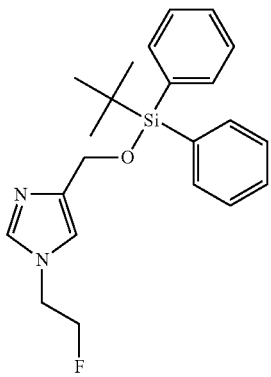

[Chemical 30]

In analogy to Steps (2) and (3) of Example 5, but using the compound (10.1 g) obtained in (1), the title compound (11.5 g) was afforded.

$^1$H-NMR (CDCl$_3$) δ: 1.08 (9H, s), 4.19 (2H, dt, J=26.9, 4.6 Hz), 4.64 (2H, dt, J=46.8, 4.9 Hz), 4.73-4.74 (2H, m), 6.85 (1H, s), 7.34-7.45 (7H, m), 7.69-7.72 (4H, m).
MS (ESI) m/z: 383 [(M+H)$^+$].

(3-1) 1-[4-(tert-Butyldiphenylsilyloxymethyl)-1-vinyl-1H-imidazol-2-yl]ethanone

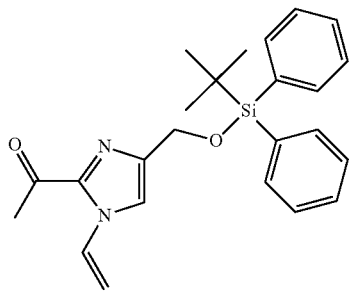

[Chemical 31]

The compound (5.35 g) obtained in (2) was dissolved in THF (200 mL), and cooled to −78° C. while stirring under nitrogen stream. To the present solution was added dropwise n-butyl lithium (2.76 M hexane solution, 7.60 mL), followed by stirring at the same temperature for 30 minutes. Then, N-methoxy-N-methylacetamide (2.91 mL) was added, and stirring was continued for 4 hours while the temperature was gradually brought back to room temperature. A saturated aqueous ammonium chloride solution was added to the reaction solution to terminate the reaction, followed by extraction with ethyl acetate. The extract was washed with saturated brine, dried over anhydrous sodium sulfate, and subsequently the solvent was distilled off under reduced pressure. The resulting residue was purified by flash chromatography (ethyl acetate/hexane=4%→40%) using silica gel column (product name: Hi-Flash Column 3 L, manufactured by Yamazen Corporation) to afford the title compound (1.48 g) and 1-[4-(tert-butyldiphenylsilyloxymethyl)-1-(2-fluoroethyl)-1H-imidazol-2-yl]ethanone (3.91 g).

1-[4-(tert-Butyldiphenylsilyloxymethyl)-1-vinyl-1H-imidazol-2-yl]ethanone $^1$H-NMR (CDCl$_3$) δ: 1.10 (9H, s), 2.61 (3H, s), 4.76 (2H, s), 4.97-5.01 (1H, m), 5.22-5.28 (1H, m), 7.34-7.45 (7H, m), 7.72-7.66 (4H, m), 7.92 (1H, dd, J=16.0, 8.6 Hz).
MS (ESI) m/z: 405 [(M+H)$^+$].

1-[4-(tert-Butyldiphenylsilyloxymethyl)-1-(2-fluoroethyl)-1H-imidazol-2-yl]ethanone $^1$H-NMR (CDCl$_3$) δ: 1.08 (9H, s), 2.61 (3H, s), 4.63 (2H, s), 4.66-4.74 (2H, m), 4.75 (2H, s), 7.04 (1H, s), 7.34-7.45 (6H, m), 7.67-7.71 (4H, m).
MS (ESI) m/z: 425 [(M+H)$^+$].

(3-2) 1-[4-(tert-Butyldiphenylsilyloxymethyl)-1-vinyl-1H-imidazol-2-yl]ethanone

(3-2a) 4-(tert-Butyldiphenylsilyloxymethyl)-1-vinyl-1H-imidazole

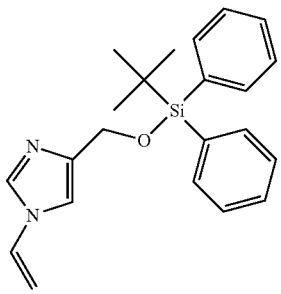

[Chemical 32]

Synthesis Example 1

The compound (6.70 g) obtained in (2) was dissolved in THF (200 mL), and cooled to −78° C. while stirring under nitrogen stream. To the present solution was added dropwise n-butyl lithium (2.76 M hexane solution, 19.0 mL), and stirring was continued at the same temperature for 1 hour. A saturated aqueous ammonium chloride solution was added to the reaction solution to terminate the reaction, followed by extraction with ethyl acetate. The extract was washed with saturated brine, dried over anhydrous sodium sulfate, and subsequently the solvent was distilled off under reduced pressure. The resulting residue was purified by flash chromatography (ethyl acetate/hexane=10%→60%) using silica gel column (product name: Hi-Flash Column 3 L, manufactured by Yamazen Corporation) to afford the title compound (3.88 g).

$^1$H-NMR (CDCl$_3$) δ: 1.09 (9H, s), 4.73-4.75 (2H, m), 4.86 (1H, dd, J=8.6, 1.7 Hz), 5.23 (1H, dd, J=15.5, 1.7 Hz), 6.85 (1H, dd, J=15.8, 8.9 Hz), 7.04-7.05 (1H, m), 7.36-7.44 (6H, m), 7.55-7.57 (1H, m), 7.72-7.69 (4H, m).

Synthesis Example 2

4(5)-(tert-Butyldiphenylsilyloxymethyl)-1H-imidazole (80.0 g) and 2-fluoroethyl tosylate (82.8 g) were dissolved in DMF (500 mL), and cooled with ice while stirring under nitrogen stream. To this reaction solution was added 60% sodium hydride (15.7 g), followed by stirring for 23 hours. The reaction solution was poured into ice water, followed by extraction with ethyl acetate. The extract was washed with ice water and saturated brine in this order, dried over anhydrous sodium sulfate, and subsequently the solvent was distilled off under reduced pressure. The resulting residue was purified by flash chromatography (ethyl acetate/hexane=10%→100%) using silica gel column (product name: KiloPack 40E, manufactured by Yamazen Corporation) to afford the title compound (6.30 g) and 5-(tert-butyldiphenylsilyloxymethyl)-1-vinyl-1H-imidazole (7.79 g), as well as the mixture (58.87 g) of 4-(tert-butyldiphenylsilyloxymethyl)-1-(2-fluoroethyl)-1H-imidazole and 5-(tert-butyldiphenylsilyloxymethyl)-1-(2-fluoroethyl)-1H-imidazole.

The above-mentioned mixture (58.87 g) of 4-(tert-butyldiphenylsilyloxymethyl)-1-(2-fluoroethyl)-1H-imidazole and 5-(tert-butyldiphenylsilyloxymethyl)-1-(2-fluoroethyl)-1H-imidazole was dissolved in THF (1000 mL), and cooled to −78° C. while stirring under nitrogen stream. To the present solution was added dropwise n-butyl lithium (2.76 M hexane solution, 167 mL), followed by stirring at the same temperature for 1 hour. A saturated aqueous ammonium chloride solution was added to the reaction solution to terminate the reaction, followed by extraction with ethyl acetate. The extract was washed with saturated brine, dried over anhydrous sodium sulfate, and subsequently the solvent was distilled off under reduced pressure. The resulting residue was purified by flash chromatography (ethyl acetate/hexane=10%→65%) using silica gel column (product name: KiloPack 40E, manufactured by Yamazen Corporation) to afford the title compound (18.8 g) and 5-(tert-butyldiphenylsilyloxymethyl)-1-vinyl-1H-imidazole (5.73 g).

(3-2b) 1-[4-(tert-Butyldiphenylsilyloxymethyl)-1-vinyl-1H-imidazol-2-yl]ethanone In analogy to Step (4) of Example 1, but using 4-(tert-butyldiphenylsilyloxymethyl)-1-vinyl-1H-imidazole (3.88 g), the title compound (2.85 g) was afforded.

(4) 1-(4-Hydroxymethyl-1-vinyl-1H-imidazol-2-yl)ethanone

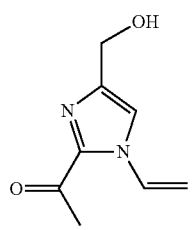

[Chemical 33]

In analogy to Step (3) of Example 6, but using the compound (2.85 g) obtained in (3-1) or (3-2), the title compound (0.649 g) was afforded.

$^1$H-NMR (CDCl$_3$) δ: 2.03 (1H, t, J=5.7 Hz), 2.67 (3H, s), 4.68 (2H, d, J=5.7 Hz), 5.03 (1H, dd, J=8.9, 1.4 Hz), 5.31 (1H, dd, J=16.0, 1.7 Hz), 7.40 (1H, s), 7.92 (1H, dd, J=15.8, 8.9 Hz).

Anal. Calcd for C$_8$H$_{10}$N$_2$O$_2$: C, 57.82; H, 6.07; N, 16.86. Found: C, 57.84; H, 6.29; N, 16.51.

Example 10

1-[4-[Hydroxy[($^2$H)$_2$]methyl]-1H-imidazol-2-yl]ethanone and 1-[5-[hydroxy[($^2$H)$_2$]methyl]-1H-imidazol-2-yl]ethanone (1) 1-Methoxymethyl-1H-imidazole-4-carboxylic acid methylester

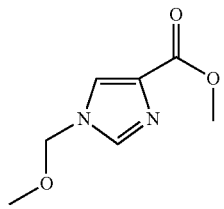

[Chemical 34]

Imidazole-4-carboxylic acid methylester (5.00 g) was dissolved in acetonitrile (100 mL), and under ice cooling and stirring, were added TEA (11.1 mL) and then chloromethylmethylether (4.47 mL), followed by heating to reflux for 3 days. After being allowed to cool to room temperature, the mixture was diluted with ethyl acetate, and washed with saturated brine. The organic layer was dried over anhydrous sodium sulfate, and the solvent was distilled off under reduced pressure. The resulting residue was purified by flash chromatography (methanol/chloroform=0%→7%) using silica gel column (product name: Hi-Flash Column 5 L, manufactured by Yamazen Corporation) to afford the title compound (3.64 g).

$^1$H-NMR (CDCl$_3$) δ: 3.31 (3H, s), 3.91 (3H, s), 5.27 (2H, s), 7.64-7.63 (1H, m), 7.74-7.73 (1H, m).

(2) (1-Methoxymethyl-1H-imidazol-4-yl) [1,1-($^2$H)$_2$]methanol

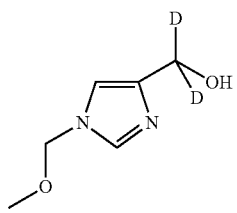

[Chemical 35]

Lithium aluminum deuteride (1.80 g) was added to THF (50 mL), and under ice cooling and stirring a THF (10 mL) solution of the compound (3.64 g) obtained in (1) was added dropwise, followed by stirring for 4 hours. To the reaction mixture, at the same temperature, were added dropwise water (1.8 mL), a 1 N aqueous sodium hydroxide solution (1.8 mL) and water (7.2 mL) in this order, and stirring was continued for 1 hour and 30 minutes while the temperature was gradually brought back to room temperature. The resulting solid material was removed by filtration, and the solvent of the filtrate was distilled off under reduced pressure to afford the title compound (1.65 g).

¹H-NMR (CDCl₃) δ: 3.27-3.28 (3H, m), 4.01-4.34 (1H, br m), 5.20-5.19 (2H, m), 6.99-7.01 (1H, m), 7.56-7.58 (1H, m).

(3) 4-[tert-Butyldiphenylsilyloxy[(²H)₂]methyl]-1-methoxymethyl-1H-imidazole

[Chemical 36]

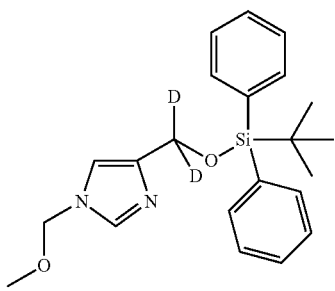

In analogy to Step (3) of Example 5, but using the compound (1.65 g) obtained in (2), the title compound (4.38 g) was afforded.
¹H-NMR (CDCl₃) δ: 1.08 (9H, s), 3.26 (3H, s), 5.18 (2H, s), 6.91-6.93 (1H, m), 7.34-7.44 (6H, m), 7.52-7.51 (1H, m), 7.72-7.69 (4H, m).
MS (ESI) m/z: 383 [(M+H)⁺].

(4) 1-[4-[tert-Butyldiphenylsilyloxy[(²H)₂]methyl]-1-methoxymethyl-1H-imidazol-2-yl]ethanone

[Chemical 37]

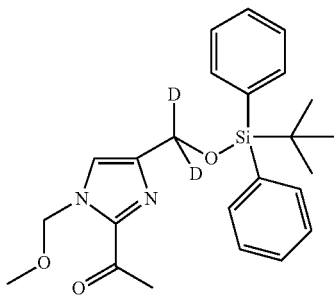

In analogy to Step (4) of Example 1, but using the compound (5.00 g) obtained in (3), the title compound (3.10 g) was afforded.
¹H-NMR (CDCl₃) δ: 1.09 (9H, s), 2.62 (3H, s), 3.32 (3H, s), 5.69 (2H, s), 7.14 (1H, s), 7.45-7.35 (6H, m), 7.71-7.68 (4H, m).
MS (ESI) m/z: 425 [(M+H)⁺].

(5) 1-[4-[Hydroxy[(²H)₂]methyl]-1-methoxymethyl-1H-imidazol-2-yl]ethanone

[Chemical 38]

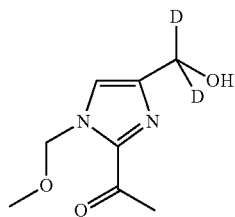

In analogy to Step (5) of Example 1, but using the compound (3.10 g) obtained in (4), the title compound (1.10 g) was afforded.
¹H-NMR (CDCl₃) δ: 2.67 (3H, s), 3.35 (3H, s), 5.71 (2H, s), 7.24 (1H, s).
MS (ESI) m/z: 187 [(M+H)⁺].

(6) 1-[4-[Hydroxy[(²H)₂]methyl]-1H-imidazol-2-yl]ethanone and 1-[5-[hydroxy[(²H)₂]methyl]-1H-imidazol-2-yl]ethanone

[Chemical 39]

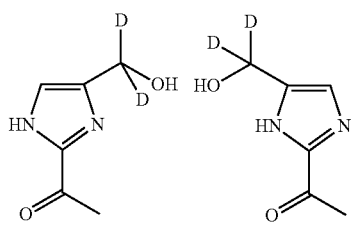

The compound (200 mg) obtained in (5) and a 1.25 N HCl methanol solution (5 mL) were mixed, followed by stirring at 50° C. for 4 hours, and a 1 N aqueous HCl solution (5 mL) was further added to the reaction solution, followed by stirring continued at 70° C. for 19 hours. The reaction solution was concentrated under reduced pressure, diluted with methanol, and subsequently rendered alkaline using saturated sodium bicarbonate water, followed by concentration again under reduced pressure. The resulting residue was purified by flash chromatography (methanol/chloroform=0%→20%) using silica gel column (product name: Hi-Flash Column 2 L, manufactured by Yamazen Corporation) to afford the mixture (136 mg) of the title compound.
¹H-NMR (CD₃OD) δ: 2.54 (3H, s), 7.32-7.07 (1H, br m).
MS (ESI) m/z: 143 [(M+H)⁺].

Example 11

1-[4-Hydroxymethyl-1-(2-propenyl)-1H-imidazol-2-yl]ethanone (1) 4-(tert-Butyldiphenylsilyloxymethyl)-1-(2-propenyl)-1H-imidazole

[Chemical 40]

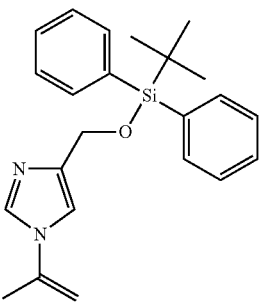

4-(tert-Butyldiphenylsilyloxymethyl)-1H-imidazole (1.000 g), 2-bromo-1-propene (1.04 mL), ethylenediamine (0.40 mL), copper iodide (0.28 g) and tripotassium phosphate (1.30 g) were suspended in dioxane (10 mL), and reacted in a microwave reactor (product name: Initiator, manufactured by Biotage, Ltd.) at 140° C. for 5 hours. The reaction solution was filtered using Celite to filter off the insolubles, followed by concentration of the mother liquor. The resulting residue was purified by flash chromatography (ethyl acetate/hexane=10%→100%) using silica gel column (product name: Hi-Flash column 3 L, manufactured by Yamazen Corporation) to afford the title compound (0.350 g).

$^1$H-NMR (CDCl$_3$) δ: 1.08 (9H, s), 2.20 (3H, d, J=1.1 Hz), 4.70-4.71 (1H, m), 4.74 (2H, d, J=1.1 Hz), 5.01 (1H, s), 7.00-7.02 (1H, m), 7.36-7.47 (6H, m), 7.65-7.63 (1H, m), 7.73-7.69 (4H, m).

MS (ESI) m/z: 377 [(M+H)$^+$].

(2) 1-[4-(tert-Butyldiphenylsilyloxymethyl)-1-(2-propenyl)-1H-imidazol-2-yl]ethanone

[Chemical 41]

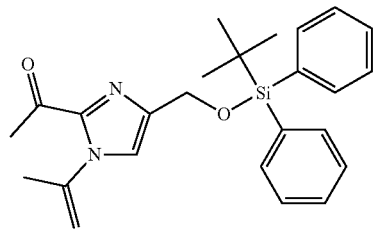

The compound (1.26 g) obtained in (1) was dissolved in THF (50 mL), and cooled to −78° C. while stirring under nitrogen stream. To the present solution was added dropwise n-butyl lithium (2.76 M hexane solution, 1.82 mL), followed by stirring at the same temperature for 30 minutes. Then, N-methoxy-N-methylacetamide (1.05 mL) was added, and stirring was continued for 30 minutes. A saturated aqueous ammonium chloride solution was added to the reaction solution to terminate the reaction, followed by extraction with ethyl acetate. The extract was washed with saturated brine, dried over anhydrous sodium sulfate, and subsequently the solvent was distilled off under reduced pressure. The resulting residue was purified by flash chromatography (ethyl acetate/hexane=5%→70%) using silica gel column (product name: Hi-Flash Column 3 L, manufactured by Yamazen Corporation) to afford the title compound (0.75 g).

$^1$H-NMR (CDCl$_3$) δ: 1.09 (9H, s), 2.12 (3H, s), 2.59 (3H, s), 4.77 (2H, s), 4.97 (1H, s), 5.11-5.14 (1H, m), 6.91 (1H, s), 7.45-7.35 (6H, m), 7.71-7.67 (4H, m).

MS (ESI) m/z: 419 [(M+H)$^+$].

(3) 1-[4-Hydroxymethyl-1-(2-propenyl)-1H-imidazol-2-yl]ethanone

[Chemical 42]

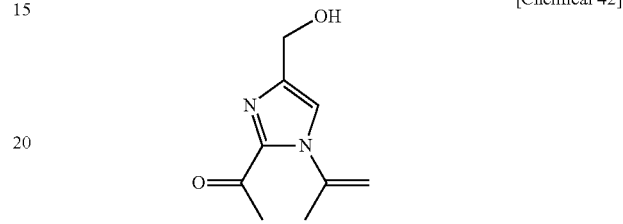

The compound (0.750 g) obtained in (2) was dissolved in THF (50 mL), followed by addition of TBAF (1.0 M THF solution, 1.79 mL) under stirring, and the stirring was continued for 1 hour. The reaction solution was concentrated, and the resulting residue was purified by flash chromatography (ethyl acetate/hexane=5%-÷100%) using amino column (product name: Hi-Flash Column 3 L, manufactured by Yamazen Corporation), washed with ethyl acetate/hexane, and subsequently dried to afford the title compound (0.280 g).

$^1$H-NMR (CDCl$_3$) δ: 2.03 (1H, t, J=5.7 Hz), 2.14 (3H, s), 2.65 (3H, s), 4.67 (2H, d, J=6.3 Hz), 5.00 (1H, s), 5.15 (1H, s), 7.02 (1H, s).

MS (ESI) m/z: 181 [(M+H)$^+$].

Examples 12 to 34

In analogy to the above-mentioned Examples, or using methods known in this field, the following compounds are afforded.

TABLE 1

| Example | Compound Name | Structural Formula | Physical Property Data |
|---|---|---|---|
| 12 | 1-(4-Hydroxymethyl-1-propyl-1H-imidazol-2-yl)ethanone | | $^1$H-NMR (CDCl$_3$) δ: 0.93 (3H, t, J = 7.4 Hz), 1.74-1.83 (2H, m), 2.65 (3H, s), 4.32 (2H, t, J = 7.4 Hz), 4.65 (2H, d, J = 5.7 Hz), 7.04 (1H, s). MS (ESI) m/z: 183 [(M + H)$^+$]. Anal. Calcd for C$_9$H$_{14}$N$_2$O$_2$: C, 59.32; H, 7.74; N, 15.37. Found: C, 59.85; H, 7.75; N, 15.10. |
| 13 | 1-[4-Hydroxymethyl-1-(2-methoxyethyl)-1H-imidazol-2-yl]ethanone | | $^1$H-NMR (CDCl$_3$) δ: 2.16 (1H, t, J = 5.7 Hz), 2.66 (3H, s), 3.31 (3H, s), 3.66 (2H, t, J = 4.9 Hz), 4.54 (2H, t, J = 4.6 Hz), 4.65 (2H, d, J = 5.7 Hz), 7.13 (1H, s). MS (ESI) m/z: 199 [(M + H)$^+$]. Anal. Calcd for C$_9$H$_{14}$N$_2$O$_3$: C, 54.53; H, 7.12; N, 14.13. Found: C, 54.85; H, 7.15; N, 13.75. |

TABLE 1-continued

| Example | Compound Name | Structural Formula | Physical Property Data |
|---|---|---|---|
| 14 | 1-[5-Hydroxymethyl-1-(2-methoxyethyl)-1H-imidazol-2-yl]ethanone | | $^1$H-NMR (CDCl$_3$) δ: 2.68 (3H, s), 3.32 (3H, s), 3.78 (2H, t, J = 4.6 Hz), 3.91 (1H, t, J = 6.0 Hz), 4.55-4.58 (2H, m), 4.59 (2H, d, J = 6.3 Hz), 7.18 (1H, s). MS (ESI) m/z: 199 [(M + H)$^+$]. |
| 15 | 1-(1-Ethyl-4-hydroxymethyl-1H-imidazol-2-yl)ethanone | | $^1$H-NMR (CDCl$_3$) δ: 1.41 (3H, t, J = 6.9 Hz), 2.65 (3H, s), 2.95 (1H, br s), 4.40 (2H, q, J = 7.4 Hz), 4.65 (2H, d, J = 4.0 Hz), 7.07 (1H, s). MS (ESI) m/z: 169 [(M + H)$^+$]. Anal. Calcd for C$_8$H$_{12}$N$_2$O$_2$: C, 57.13; H, 7.19; N, 16.66. Found: C, 57.14; H, 7.03; N, 16.77. |
| 16 | 2-Acetyl-5-hydroxymethylimidazole-1-sulfonic acid dimethylamide | | $^1$H-NMR (CDCl$_3$) δ: 2.66 (3H, s), 3.11 (6H, s), 4.75-4.79 (2H, m), 7.07 (1H, s). MS (ESI) m/z: 248 [(M + H)$^+$]. Anal. Calcd for C$_8$H$_{13}$N$_3$O$_4$S: C, 38.86; H, 5.30; N, 16.99; S, 12.97. Found: C, 38.97; H, 5.34; N, 16.77; S, 12.77. |
| 17 | 1-(1-Cyclohexyloxymethyl-5-hydroxymethyl-1H-imidazol-2-yl)ethanone | | $^1$H-NMR (CDCl$_3$) δ: 1.16-1.35 (4H, m), 1.46-1.59 (2H, m), 1.65-1.86 (4H, m), 2.69 (3H, s), 3.09 (1H, t, J = 6.3 Hz), 3.46-3.55 (1H, m), 4.69 (2H, d, J = 6.3 Hz), 6.03 (2H, s), 7.17 (1H, s). MS (ESI) m/z: 253 [(M + H)$^+$]. |
| 18 | 1-(1-Hexyl-4-hydroxymethyl-1H-imidazol-2-yl)ethanone | | $^1$H-NMR (CDCl$_3$) δ: 0.88 (3H, t, J = 6.9 Hz), 1.26-1.33 (6H, m), 1.72-1.78 (2H, m), 2.20 (1H, t, J = 5.7 Hz), 2.65 (3H, s), 4.34 (2H, t, J = 7.2 Hz), 4.65 (2H, d, J = 5.7 Hz), 7.03 (1H, s). MS (ESI) m/z: 225 (M + H)$^+$. Anal. Calcd for C$_{12}$H$_{20}$N$_2$O$_2$: C, 64.26; H, 8.99; N, 12.49. Found: C, 64.22; H, 8.90; N, 12.07. |

TABLE 2

| Example | Compound Name | Structural Formula | Physical Property Data |
|---|---|---|---|
| 19 | 1-(1-Cyclopropyl-4-hydroxymethyl-1H-imidazol-2-yl)ethanone | | $^1$H-NMR (CDCl$_3$) δ: 0.86-0.92 (2H, m), 1.09-1.14 (2H, m), 2.05-2.10 (1H, m), 2.65 (3H, s), 3.84-3.89 (1H, m), 4.62 (2H, d, J = 5.7 Hz), 7.03 (1H, s). MS (ESI) m/z: 181 [(M + H)$^+$]. Anal. Calcd for C$_9$H$_{12}$N$_2$O$_2$: C, 59.99; H, 6.71; N, 15.55. Found: C, 60.02; H, 6.63; N, 15.48. |

TABLE 2-continued

| Example | Compound Name | Structural Formula | Physical Property Data |
|---|---|---|---|
| 20 | 1-(4-Hydroxymethyl-1-pentyl-1H-imidazol-2-yl)ethanone | | $^1$H-NMR (CDCl$_3$) δ: 0.90 (3H, t, J = 7.2 Hz), 1.25-1.38 (4H, m), 1.73-1.79 (2H, m), 2.38 (1H, t, J = 5.7 Hz), 2.65 (3H, s), 4.34 (2H, t, J = 7.4 Hz), 4.65 (2H, d, J = 5.7 Hz), 7.04 (1H, s).<br>MS (ESI) m/z: 211 (M + H)$^+$.<br>Anal. Calcd for C$_{11}$H$_{18}$N$_2$O$_2$: C, 62.83; H, 8.63; N, 13.32.<br>Found: C, 62.92; H, 8.60; N, 13.05. |
| 21 | 2,2-Difluoro-1-(4-hydroxymethyl-1-methoxymethyl-1H-imidazol-2-yl)ethanone | | $^1$H-NMR (CDCl$_3$) δ: 3.39 (3H, s), 4.71 (2H, s), 5.74 (2H, s), 6.92 (1H, t, J = 53.8 Hz), 7.41 (1H, s).<br>MS (ESI) m/z: 221 [(M + H)$^+$]. |
| 22 | Acetic acid (2-acetyl-1-ethyl-1H-imidazol-4-yl)methylester | | $^1$H-NMR (CDCl$_3$) δ: 1.41 (3H, t, J = 7.4 Hz), 2.09 (3H, s), 2.66 (3H, s), 4.40 (2H, q, J = 7.4 Hz), 5.06 (2H, s), 7.14 (1H, s). |
| 23 | Benzoic acid (2-acetyl-1-ethyl-1H-imidazol-4-yl)methylester | | $^1$H-NMR (CDCl$_3$) δ: 1.42 (3H, t, J = 6.9Hz), 2.68 (3H, s), 4.40 (2H, q, J = 6.9 Hz), 5.33 (2H, s), 7.22 (1H, s), 7.41-7.45 (2H, m), 7.53-7.58 (1H, m), 8.08-8.05 (2H, m).<br>MS (ESI) m/z: 273 [(M + H)$^+$].<br>Anal. Calcd for C$_{15}$H$_{16}$N$_2$O$_3$: C, 66.16; H, 5.92; N, 10.29.<br>Found: C, 65.98; H, 5.91; N, 10.25. |
| 24 | Pivalic acid (2-acetyl-1-ethyl-1H-imidazol-4-yl)methylester | | $^1$H-NMR (CDCl$_3$) δ: 1.21 (9H, s), 1.41 (3H, t, J = 6.9 Hz), 2.65 (3H, s), 4.40 (2H, q, J = 6.3 Hz), 5.07 (2H, s), 7.10 (1H, s).<br>MS (ESI) m/z: 253 [(M + H)$^+$]. |
| 25 | 1-[4-Hydroxymethyl-1-(2-methoxy-1-methylethyl)-1H-imidazol-2-yl]ethanone | | $^1$H-NMR (CDCl$_3$) δ: 1.45 (3H, d, J = 6.9 Hz), 2.24 (1H, t, J = 5.7 Hz), 2.66 (3H, s), 3.32 (3H, s), 3.52-3.59 (2H, m), 4.66 (2H, d, J = 5.7 Hz), 5.64-5.67 (1H, m), 7.31 (1H, s).<br>MS (ESI) m/z: 213 [(M + H)$^+$]. |

TABLE 2-continued

| Example | Compound Name | Structural Formula | Physical Property Data |
|---|---|---|---|
| 26 | 1-(1-tert-Butyl-4-hydroxymethyl-1H-imidazol-2-yl)ethanone | | $^1$H-NMR (CDCl$_3$) δ: 1.67 (9H, s), 2.08-2.02 (1H, m), 2.70 (3H, s), 4.64 (2H, d, J = 5.7 Hz), 7.29 (1H, s). |

TABLE 3

| Example | Compound Name | Structural Formula | Physical Property Data |
|---|---|---|---|
| 27 | 2,2-Difluoro-1-(1-ethyl-4-hydroxymethyl-1H-imidazol-2-yl)ethanone | | $^1$H-NMR (CDCl$_3$) δ: 1.46 (3H, t, J = 7.2 Hz), 2.16 (1H, t, J = 5.7 Hz), 4.45 (2H, q, J = 7.2 Hz), 4.69 (2H, d, J = 5.2 Hz), 6.93 (1H, t, J = 53.8 Hz), 7.25 (1H, s).<br>MS (ESI) m/z: 205 (M + H)$^+$. |
| 28 | 1-[1-(Furan-2-ylmethyl)-4-hydroxymethyl-1H-imidazol-2-yl]ethanone | | $^1$H-NMR (CDCl$_3$) δ: 2.07 (1H, t, J = 6.0 Hz), 2.66 (3H, s), 4.63 (2H, d, J = 6.3 Hz), 5.58 (2H, s), 6.34 (1H, dd, J = 3.1, 2.0 Hz), 6.41 (1H, d, J = 2.9 Hz), 7.07 (1H, s), 7.38 (1H, d, J = 1.2 Hz).<br>MS (FAB) m/z: 221 [(M + H)$^+$].<br>Anal. Calcd for C$_{11}$H$_{12}$N$_2$O$_3$: C, 59.99; H, 5.49; N, 12.72.<br>Found: C, 60.34; H, 5.54; N, 12.73. |
| 29 | 1-[4-Hydroxymethyl-1-(oxetan-3-yl)-1H-imidazol-2-yl]ethanone | | $^1$H-NMR (CDCl$_3$) δ: 2.09 (1H, t, J = 6.3 Hz), 2.64 (3H, s), 4.70 (2H, d, J = 5.7 Hz), 4.74 (2H, t, J = 7.4 Hz), 5.13 (2H, t, J = 7.2 Hz), 6.05-6.11 (1H, m), 7.48 (1H, s).<br>MS (ESI) m/z: 197 [(M + H)$^+$].<br>Anal. Calcd for C$_9$H$_{12}$N$_2$O$_3$: C, 55.09; H, 6.16; N, 14.28.<br>Found: C, 55.25; H, 6.15; N, 14.29. |
| 30 | 1-[1-(sec-Butyl)-4-hydroxymethyl-1H-imidazol-2-yl]ethanone | | $^1$H-NMR (CDCl$_3$) δ: 0.84 (3H, t, J = 7.3 Hz), 1.41 (3H, d, J = 6.4 Hz), 1.69-1.79 (2H, m), 2.66 (3H, s), 4.66 (2H, s), 5.35-5.45 (1H, m), 7.19 (1H, s).<br>MS (ESI) m/z: 197 [(M + H)$^+$]. |
| 31 | 1-[1-(2-Fluoroethyl)-4-hydroxymethyl-1H-imidazol-2-yl]ethanone | | $^1$H-NMR (CDCl$_3$) δ: 2.04 (1H, t, J = 5.7 Hz), 2.67 (3H, s), 4.64-4.76 (6H, m), 7.13 (1H, s).<br>MS (ESI) m/z: 187 [(M + H)$^+$].<br>Anal. Calcd for C$_8$H$_{11}$FN$_2$O$_2$: C, 51.61; H, 5.96; F, 10.20; N, 15.05.<br>Found: C, 51.74; H, 5.96; F, 9.98; N, 15.05. |

TABLE 3-continued

| Example | Compound Name | Structural Formula | Physical Property Data |
|---|---|---|---|
| 32 | 1-[1-(3-Fluoropropyl)-5-hydroxymethyl-1H-imidazol-2-yl]ethanone | | $^1$H-NMR (CDCl$_3$) δ: 1.70 (1H, t, J = 5.5 Hz), 2.14-2.29 (2H, m), 2.67 (3H, s), 4.44 (1H, t, J = 5.5 Hz), 4.52-4.58 (3H, m), 4.72 (2H, d, J = 5.5 Hz), 7.15 (1H, s). MS (ESI) m/z: 201 [(M + H)$^+$]. Anal. Calcd for C$_9$H$_{13}$FN$_2$O$_2$: C, 53.99; H, 6.54; F, 9.49; N, 13.99. Found: C, 54.05; H, 6.55; F, 9.23; N, 13.92. |
| 33 | 1-(1-Dimethylamino-4-hydroxymethyl-1H-imidazol-2-yl)ethanone | | $^1$H-NMR (CDCl$_3$) δ: 2.04 (1H, t, J = 5.7 Hz), 2.66 (3H, s), 2.91 (6H, s), 4.63 (2H, d, J = 5.7 Hz), 7.33 (1H, s). MS (ESI) m/z: 184 [(M + H)$^+$]. |
| 34 | 1-[4-[Hydroxy[($^2$H)$_2$]methyl]-1-methoxymethyl-1H-imidazol-2-yl]ethanone | | $^1$H-NMR (CDCl$_3$) δ: 2.67 (3H, s), 3.35 (3H, s), 5.71 (2H, s), 7.24 (1H, s). MS (ESI) m/z: 187 [(M + H)$^+$]. |

Example 35

1-(5-Hydroxymethyl-4-methyl-1H-imidazol-2-yl)ethanone, and 1-(4-hydroxymethyl-5-methyl-1H-imidazol-2-yl)ethanone (1) 4-(tert-Butyldiphenylsilyloxymethyl)-5-methyl-1H-imidazole, and 5-(tert-butyldiphenylsilyloxymethyl)-4-methyl-1H-imidazole

[Chemical 43]

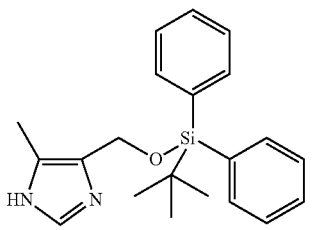

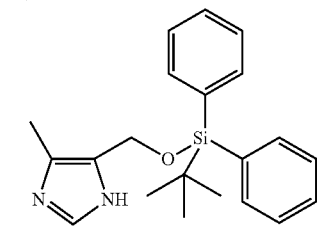

(5-Methyl-1H-imidazol-4-yl)methanol hydrochloride, and (4-methyl-1H-imidazol-5-yl)methanol hydrochloride (5.00 g) were suspended in dichloromethane (100 mL), followed by addition of triethylamine (14.1 mL) and TBDPSCl (13.1 mL) under stirring, and the stirring was continued for 3 days. The reaction solution was diluted with water, and extracted with chloroform. The combined extract was washed with saturated brine, dried over anhydrous sodium sulfate, and subsequently the solvent was distilled off under reduced pressure. The resulting residue was purified by flash chromatography (methanol/chloroform=0%→5%) using silica gel column (product name: cartridge 40M, manufactured by Biotage, Ltd.) to afford the mixture (7.77 g) of the title compound.

$^1$H-NMR (CDCl$_3$) δ: 1.05 (9H, s), 2.03 (3H, s), 4.68 (2H, s), 7.37-7.47 (7H, m), 7.66-7.68 (4H, m).

(2) 4-(tert-Butyldiphenylsilyloxymethyl)-5-methyl-1-(2-trimethylsilylethoxymethyl)-1H-imidazole, and 5-(tert-butyldiphenylsilyloxymethyl)-4-methyl-1-(2-trimethylsilylethoxymethyl)-1H-imidazole

[Chemical 44]

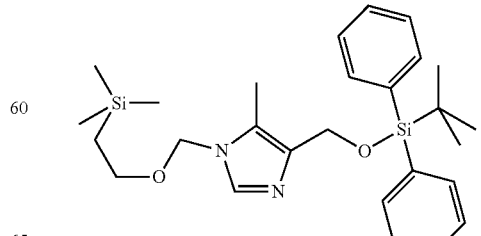

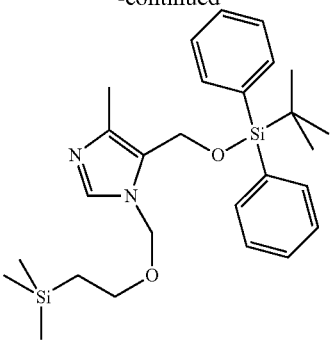

The mixture (35.4 g) obtained in (1) was dissolved in acetonitrile (500 mL), followed by addition of TEA (37.8 mL) and then 2-trimethylsilylethoxymethyl chloride (hereinafter, also referred to as SEMCl) (21.4 mL) while stirring under ice cooling, followed by stirring at 70° C. for 12 hours. The reaction mixture was allowed to cool to room temperature, and the solvent was distilled off under reduced pressure. The residue was diluted with ethyl acetate, subsequently washed with saturated brine, and dried over anhydrous sodium sulfate. The solvent was distilled off under reduced pressure, and the resulting residue was purified by flash chromatography (ethyl acetate/hexane=15%→50%) using silica gel column (product name: cartridge 65i, manufactured by Biotage, Ltd.) to afford 4-(tert-butyldiphenylsilyloxymethyl)-5-methyl-1-(2-trimethylsilylethoxymethyl)-1H-imidazole (17.9 g) as a low polar component, and 5-(tert-butyldiphenylsilyloxymethyl)-4-methyl-1-(2-trimethylsilylethoxymethyl)-1H-imidazole (9.42 g) as a high polar component.

Low polar component: 4-(tert-butyldiphenylsilyloxymethyl)-5-methyl-1-(2-trimethylsilylethoxymethyl)-1H-imidazole $^1$H-NMR (CDCl$_3$) δ: −0.02 (9H, s), 0.89 (2H, t, J=8.2 Hz), 1.04 (9H, s), 2.10 (3H, s), 3.45 (2H, t, J=8.2 Hz), 4.65 (2H, s), 5.14 (2H, s), 7.34-7.45 (3H, m), 7.75-7.70 (4H, m).

MS (ESI) m/z: 481 [M+H]$^+$.

High polar component: 5-(tert-butyldiphenylsilyloxymethyl)-4-methyl-1-(2-trimethylsilylethoxymethyl)-1H-imidazole $^1$H-NMR (CDCl$_3$) δ: −0.03 (9H, s), 0.89 (2H, t, J=8.0 Hz), 1.01 (9H, s), 1.92 (3H, s), 3.46 (2H, t, J=8.3 Hz), 4.68 (2H, s), 5.38 (2H, s), 7.37-7.47 (3H, m), 7.66-7.68 (4H, m).

MS (ESI) m/z: 481 [M+H]$^+$.

(3) 1-[5-(tert-Butyldiphenylsilyloxymethyl)-4-methyl-1-(2-trimethylsilylethoxymethyl)-1H-imidazol-2-yl]ethanone

[Chemical 45]

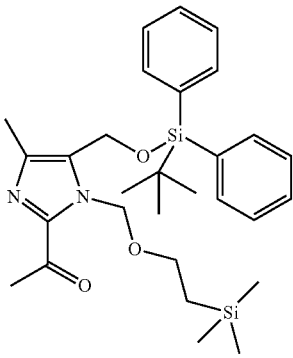

The mixture (2.24 g) obtained in (2) was dissolved in THF (30 mL), followed by cooling to −78° C. while stirring under an argon atmosphere. To the present solution was added dropwise n-butyl lithium (2.69 M hexane solution, 2.82 mL) slowly using a syringe, followed by stirring at the same temperature for 30 minutes. Then, N-methoxy-N-methylacetamide (0.95 mL) was added using a syringe, and stirring was continued for 17 hours while the temperature was raised to room temperature. A saturated aqueous ammonium chloride solution was added to the reaction solution to terminate the reaction, followed by extraction with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=0%→15%) using silica gel column (product name: SNAP Cartridge KP-Sil 100 g, manufactured by Biotage, Ltd.) to afford the title compound (1.85 g).

$^1$H-NMR (CDCl$_3$) δ: −0.05 (9H, s), 0.86 (2H, t, J=8.3 Hz), 1.02 (9H, s), 1.97 (3H, s), 2.65 (3H, s), 3.50 (2H, t, J=8.0 Hz), 4.73 (2H, s), 5.93 (2H, s), 7.38-7.47 (6H, m), 7.65-7.66 (4H, m).

(4) 1-[5-Hydroxymethyl-4-methyl-1-(2-trimethylsilylethoxymethyl)-1H-imidazol-2-yl]ethanone

[Chemical 46]

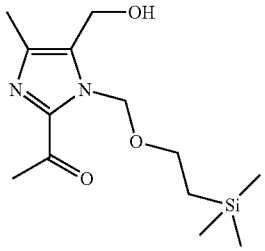

The compound (1.85 g) obtained in (3) was dissolved in THF (20 mL), followed by addition of TBAF (1.0 M THF solution, 3.54 mL) under stirring, and the stirring was continued for 1 hour. The reaction solution was diluted with water, followed by extraction with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=5%→70%) using amino column (product name: SNAP Cartridge NH 55 g, manufactured by Biotage, Ltd.) to afford the title compound (1.01 g).

$^1$H-NMR (CDCl$_3$) δ: −0.02 (9H, s), 0.87-0.92 (2H, m), 2.31 (3H, s), 2.67 (3H, s), 2.99 (1H, t, J=6.3 Hz), 3.57-3.61 (2H, m), 4.63 (2H, d, J=6.3 Hz), 5.96 (2H, s).

(5) 1-(5-Hydroxymethyl-4-methyl-1H-imidazol-2-yl)ethanone, and 1-(4-hydroxymethyl-5-methyl-1H-imidazol-2-yl)ethanone

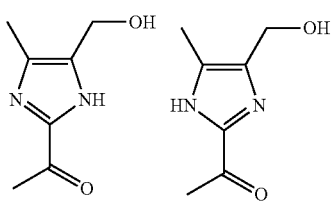

[Chemical 47]

The compound (1.01 g) obtained in (4) was dissolved in a 4 N hydrochloric acid/1,4-dioxane solution (10 mL), and stirring was continued for 1.5 hours while the mixture was warmed to 100° C. After being allowed to cool to room temperature, a 1 N aqueous sodium hydroxide solution was added for neutralization, and subsequently the solvent was distilled off under reduced pressure. The resulting residue was purified by flash chromatography (ethyl acetate/hexane=5%→90%, then methanol/ethyl acetate=5%) using amino column (product name: SNAP Cartridge KP-NH 55 g, manufactured by Biotage, Ltd.) to afford the mixture (0.24 g) of the title compound.

$^1$H-NMR (CD$_3$OD) δ: 2.26-2.32 (3H, m), 2.51 (3H, s), 4.54 (2H, br s).

MS (ESI) m/z: 155 [M+H]$^+$.

Anal. Calcd for C$_7$H$_{10}$N$_2$O$_2$: C, 54.54; H, 6.54; N, 18.17. Found: C, 54.35; H, 6.49; N, 17.96.

Example 41

(S)-2-Amino-3-phenyl propionic acid (2-acetyl-1H-imidazol-4-yl)methylester, and (S)-2-amino-3-phenyl propionic acid (2-acetyl-3H-imidazol-4-yl)methylester

(1) 4-(tert-Butyldiphenylsilyloxymethyl)-1-(2-trimethylsilylethoxymethyl)-1H-imidazole

[Chemical 48]

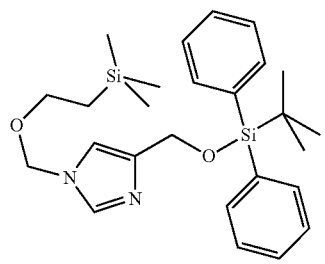

1-(2-Trimethylsilylethoxymethyl)-1H-imidazole-4-methanol (100 g) was dissolved in dichloromethane (1 L), and under stirring TEA (122 mL), DMAP (5.35 g), and then TBDPSCl (149 mL) were added. After stirring for 1 day, the reaction mixture solution was washed with water, dried over anhydrous sodium sulfate, and subsequently the solvent was distilled off under reduced pressure. The resulting residue was purified by flash chromatography (ethyl acetate/hexane=25%-50%) using silica gel column (product name: Ultra Pack E, manufactured by Yamazen Corporation) to afford the title compound (146 g).

$^1$H-NMR (CDCl$_3$) δ: −0.01 (9H, s), 0.91 (2H, t, J=8.7 Hz), 1.08 (9H, s), 3.48 (2H, t, J=8.2 Hz), 4.75 (2H, s), 5.22 (2H, s), 6.93-6.96 (1H, m), 7.34-7.44 (6H, m), 7.50-7.52 (1H, m), 7.68-7.73 (4H, m).

(2) 1-[4-(tert-Butyldiphenylsilyloxymethyl)-1-(2-trimethylsilylethoxymethyl)-1H-imidazol-2-yl]ethanone

[Chemical 49]

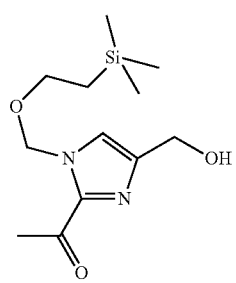

In analogy to Step (4) of Example 1, but using the compound (30.0 g) obtained in (1), the title compound (24.4 g) was afforded.

$^1$H-NMR (CDCl$_3$) δ: −0.01 (9H, s), 0.93 (2H, t, J=7.8 Hz), 1.09 (9H, s), 2.61 (3H, s), 3.57 (2H, t, J=8.2 Hz), 4.77 (2H, s), 5.73 (2H, s), 7.20 (1H, s), 7.34-7.45 (6H, m), 7.73-7.67 (4H, m).

MS (ESI) m/z: 509 [(M+H)$^+$].

(3) 1-[4-Hydroxymethyl-1-(2-trimethylsilylethoxymethyl)-1H-imidazol-2-yl]ethanone

[Chemical 50]

In analogy to Step (5) of Example 1, but using the compound (24.4 g) obtained in (2), the title compound (14.1 g) was afforded.

$^1$H-NMR (CD$_3$OD) δ: −0.03 (9H, s), 0.90 (2H, t, J=8.0 Hz), 2.58 (3H, s), 3.59 (2H, t, J=8.0 Hz), 4.57 (2H, s), 5.73 (2H, s), 7.43 (1H, s).

MS (ESI) m/z: 271 [(M+H)$^+$].

(4) (S)-2-tert-Butoxycarbonylamino-3-phenyl propionic acid [2-acetyl-1-(2-trimethylsilylethoxymethyl)-1H-imidazol-4-yl]methylester

[Chemical 51]

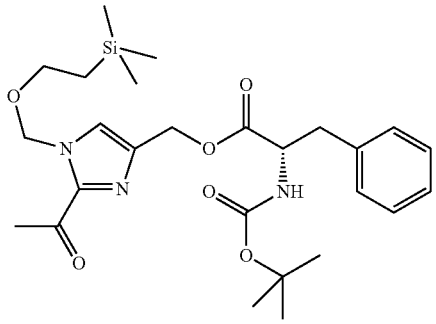

The compound (2.00 g) obtained in (3) was dissolved in dichloromethane (10 mL), and Boc-Leu-OH (2.21 g), EDC.HCl (2.13 g), and DMAP (0.99 g) were added while stirring. After the stirring was continued for 1 day, the solvent was distilled off under reduced pressure. The resulting residue was purified by flash chromatography (ethyl acetate/chloroform=0%→25%) using silica gel column (product name: Hi-Flash Column 3 L, manufactured by Yamazen Corporation) to afford the title compound (3.20 g).
$^1$H-NMR (CDCl$_3$) δ: −0.02 (9H, s), 0.93 (2H, t, J=8.7 Hz), 1.57 (9H, s), 2.67 (3H, s), 3.02-3.15 (2H, m), 3.54-3.59 (2H, m), 4.58-4.65 (1H, m), 4.95-5.00 (1H, m), 5.09-5.18 (2H, m), 5.69-5.75 (2H, m), 7.26-7.06 (6H, m).

(5) (S)-2-Amino-3-phenyl propionic acid (2-acetyl-1H-imidazol-4-yl)methylester, and (S)-2-amino-3-phenyl propionic acid (2-acetyl-3H-imidazol-4-yl)methylester

[Chemical 52]

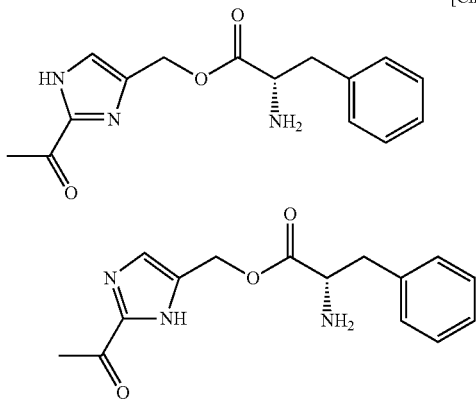

The compound (3.16 g) obtained in (4) and a 4 N hydrochloric acid/1,4-dioxane solution (10 mL) were mixed, followed by stirring at 50° C. for 4 hours. The reaction solution was allowed to cool, and subsequently the solvent was distilled off under reduced pressure. The resulting residue was purified by reversed phase preparative HPLC, and subsequently lyophilized to afford the mixture (1.75 g) of the title compound.
MS (ESI) m/z: 286 [(M−H)$^+$].

Example 42

Aminoacetic acid (2-acetyl-1H-imidazol-4-yl)methylester dihydrochloride, and aminoacetic acid (2-acetyl-3H-imidazol-4-yl)methylester dihydrochloride (1) tert-Butoxycarbonylaminoacetic acid [2-acetyl-1-(2-trimethylsilylethoxymethyl)-1H-imidazol-4-yl]methylester

[Chemical 53]

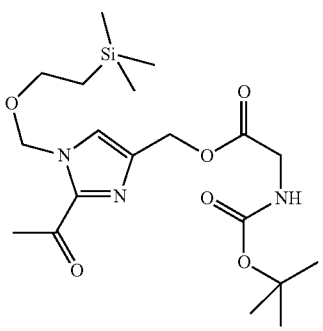

In analogy to Step (4) of Example 41, but from the compound (1.00 g) obtained in Step (3) of Example 41 and Boc-Gly-OH (0.78 g), the title compound (1.32 g) was afforded.
$^1$H-NMR (CDCl$_3$) δ: −0.01 (9H, s), 0.90-0.96 (2H, m), 1.45 (9H, s), 2.66 (3H, s), 3.55-3.60 (3H, m), 3.92-3.97 (2H, m), 4.96-5.03 (1H, m), 5.17 (2H, s), 5.73 (2H, s), 7.34 (1H, s).
MS (ESI) m/z: 428 [(M+H)$^+$].

(2) Aminoacetic acid (2-acetyl-1H-imidazol-4-yl)methylester dihydrochloride, and aminoacetic acid (2-acetyl-3H-imidazol-4-yl)methylester dihydrochloride

[Chemical 54]

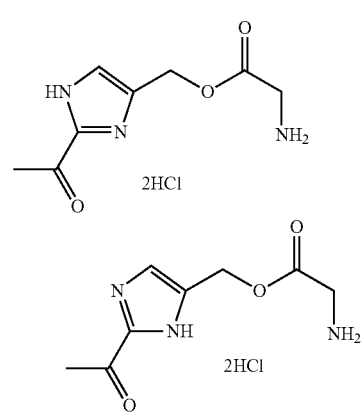

The compound (1.20 g) obtained in (1) and a 2 N HCl/1,4-dioxane solution (10 mL) were mixed, followed by stirring at 70° C. for 20 hours. The reaction solution was allowed to cool to room temperature, and subsequently concentrated under reduced pressure to obtain the residue, which was washed with hexane, subsequently obtained by filtration, and dried to afford the mixture (627 mg) of the title compound.
MS (ESI) m/z: 198 [(M+H)+].

Example 43

(S)-2-Amino-4-methylpentanoic acid (2-acetyl-1H-imidazol-4-yl)methylester, and (S)-2-amino-4-methylpentanoic acid (2-acetyl-3H-imidazol-4-yl)methylester (1) (S)-2-tert-Butoxycarbonylamino-4-methylpentanoic acid [2-acetyl-1-(2-trimethylsilylethoxymethyl)-1H-imidazol-4-yl]methylester

[Chemical 55]

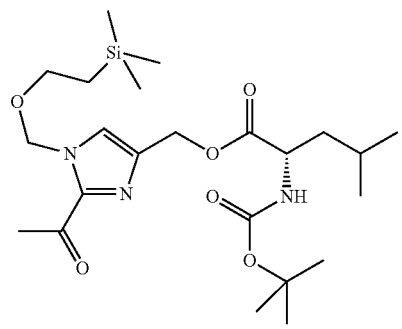

In analogy to Step (4) of Example 41, but from the compound (2.00 g) obtained in Step (3) of Example 41 and Boc-Leu-OH (2.21 g), the title compound (3.16 g) was afforded.
¹H-NMR (CDCl₃) δ: −0.01 (9H, s), 0.90-0.96 (8H, m), 1.43 (9H, s), 1.45-1.75 (3H, m), 2.66 (3H, s), 3.57 (2H, t, J=8.2 Hz), 4.29-4.39 (1H, m), 4.85-4.91 (1H, m), 5.15 (2H, s), 5.73 (2H, s), 7.33 (1H, s).

(2) (S)-2-Amino-4-methylpentanoic acid (2-acetyl-1H-imidazol-4-yl)methylester, and (S)-2-amino-4-methylpentanoic acid (2-acetyl-3H-imidazol-4-yl) methylester

[Chemical 56]

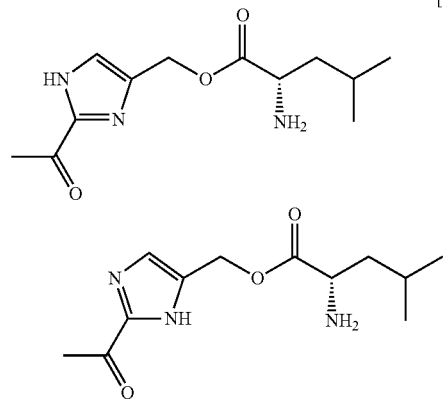

The compound (3.16 g) obtained in (1) and a 4 N hydrochloric acid/1,4-dioxane solution (10 mL) were mixed, followed by stirring at 50° C. for 4 hours. The reaction solution was allowed to cool, and subsequently the solvent was distilled off under reduced pressure. The resulting residue was purified by reversed phase preparative HPLC, and subsequently lyophilized to afford the mixture (1.27 g) of the title compound.
MS (ESI) m/z: 252 [(M−H)+].

Example 44

(S)-Pyrrolidine-2-carboxylic acid (2-acetyl-1H-imidazol-4-yl)methylester dihydrochloride, and (S)-pyrrolidine-2-carboxylic acid (2-acetyl-3H-imidazol-4-yl)methylester dihydrochloride (1) (S)-Pyrrolidine-1,2-dicarboxylic acid 2-[(2-acetyl-1H-imidazol-4-yl)methyl] 1-tert-butyl ester, and (S)-pyrrolidine-1,2-dicarboxylic acid 2-[(2-acetyl-3H-imidazol-4-yl)methyl] 1-tert-butyl ester

[Chemical 57]

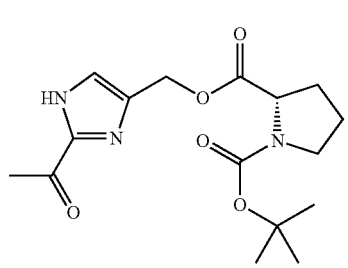

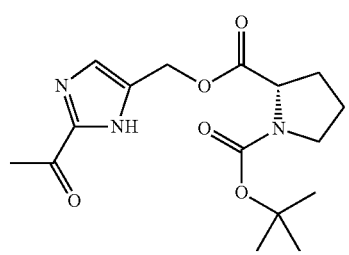

In analogy to Step (4) of Example 41, but from the compound (2.00 g) obtained in Example 2 and Boc-Pro-OH (1.10 g), the mixture (1.44 g) of the title compound was afforded.
MS (ESI) m/z: 336 [(M−H)+].

(2) (S)-Pyrrolidine-2-carboxylic acid (2-acetyl-1H-imidazol-4-yl)methylester dihydrochloride, and (S)-pyrrolidine-2-carboxylic acid (2-acetyl-3H-imidazol-4-yl)methylester dihydrochloride

[Chemical 58]

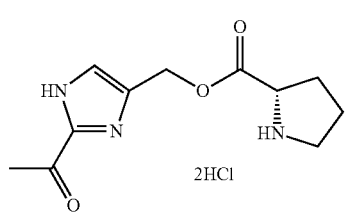

-continued

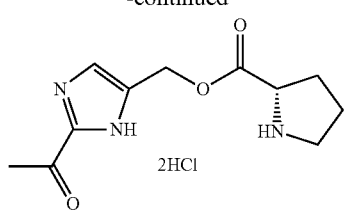

2HCl

The mixture (1.44 g) obtained in (1) and a 4 N hydrochloric acid/1,4-dioxane solution (10 mL) were mixed, followed by stirring at room temperature for 17 hours. The solvent of the reaction solution was distilled off under reduced pressure, and the residue was washed with hexane and, subsequently dried to afford the mixture (1.00 g) of the title compound.

MS (ESI) m/z: 238 [(M+H)$^+$].

Example 45

Benzoic acid (2-acetyl-5-methyl-1H-imidazol-4-yl)methylester, and benzoic acid (2-acetyl-5-methyl-3H-imidazol-4-yl)methylester (1) 1-[4-(tert-Butyldiphenylsilyloxymethyl)-5-methyl-1-(2-trimethylsilylethoxymethyl)-1H-imidazol-2-yl]ethanone

[Chemical 59]

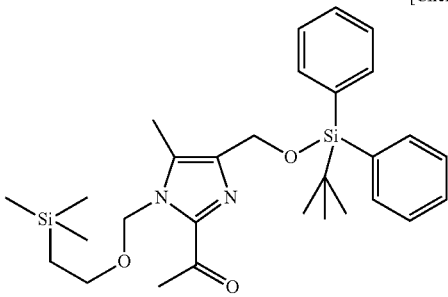

4-(tert-Butyldiphenylsilyloxymethyl)-5-methyl-1-(2-trimethylsilylethoxymethyl)-1H-imidazole (24.6 g) was dissolved in THF (300 mL), and cooled to −78° C. while stirring under an argon atmosphere. To the present solution was added dropwise n-butyl lithium (2.66 M hexane solution, 28.9 mL) slowly using a syringe, followed by stirring at the same temperature for 30 minutes. Then, N-methoxy-N-methylacetamide (10.5 mL) was added using a syringe, and stirring was continued for 2 hours while the temperature was raised to room temperature. A saturated aqueous ammonium chloride solution was added to the reaction solution to terminate the reaction, followed by extraction with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=0%→50%) using silica gel column (product name: Hi-Flash Column 5 L, manufactured by Yamazen Corporation) to afford the title compound (11.7 g).

$^1$H-NMR (CDCl$_3$) δ: −0.04 (9H, s), 0.85-0.94 (2H, m), 1.05 (9H, s), 2.18 (3H, s), 2.61 (3H, s), 3.50-3.56 (2H, m), 4.72 (2H, s), 5.75 (1H, s), 7.45-7.34 (6H, m), 7.72-7.68 (4H, m).

MS (ESI) m/z: 523 [M+H]$^+$.

(2) 1-[4-Hydroxymethyl-5-methyl-1-(2-trimethylsilylethoxymethyl)-1H-imidazol-2-yl]ethanone

[Chemical 60]

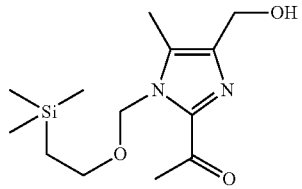

The compound (11.7 g) obtained in (1) was dissolved in THF (100 mL), followed by addition of TBAF (1.0 M THF solution, 24.7 mL) under stirring, and the stirring was continued for 1 hour. The reaction solution was diluted with water, followed by extraction with ethyl acetate. The combined extract was washed with saturated brine, dried over anhydrous sodium sulfate, and subsequently the solvent was distilled off under reduced pressure. The resulting residue was purified by flash chromatography (ethyl acetate/hexane=10%→100%) using amino column (product name: Hi-Flash Column 3 L, manufactured by Yamazen Corporation) to afford the title compound (5.41 g).

$^1$H-NMR (CDCl$_3$) δ: −0.03 (9H, s), 0.86-0.92 (2H, m), 2.24 (1H, t, J=5.5 Hz), 2.34 (3H, s), 2.64 (3H, s), 3.52-3.57 (2H, m), 4.63 (2H, d, J=6.0 Hz), 5.80 (2H, s).

MS (ESI) m/z: 285 [M+H]$^+$.

(3) Benzoic acid (2-acetyl-5-methyl-1-(2-trimethylsilylethoxymethyl)-1H-imidazol-4-yl)methylester

[Chemical 61]

In analogy to Example 3, but using the compound (0.500 g) obtained in (2) and benzoyl chloride (0.306 g), the title compound (0.602 g) was afforded.

$^1$H-NMR (CDCl$_3$) δ: −0.05 (9H, s), 0.85 (2H, dd, J=8.2, 9.6 Hz), 2.38 (3H, s), 2.67 (3H, s), 3.54 (2H, dd, J=8.2, 9.6 Hz), 5.44 (2H, s), 5.95 (2H, s), 7.43 (2H, t, J=7.8 Hz), 7.54-7.59 (1H, m), 8.01 (2H, dd, J=8.2, 1.4 Hz).

MS (ESI) m/z: 389 [(M+H)$^+$].

(4) Benzoic acid (2-acetyl-5-methyl-1H-imidazol-4-yl)methylester and benzoic acid (2-acetyl-5-methyl-3H-imidazol-4-yl)methylester

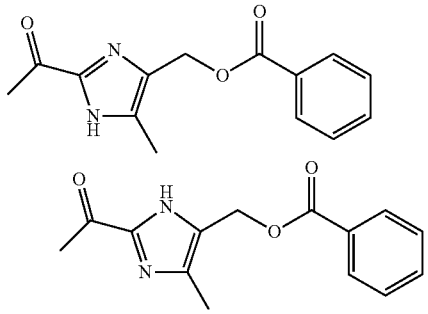

[Chemical 62]

The compound (0.602 g) obtained in (3) was dissolved in 4 N hydrochloric acid (5.00 mL), followed by stirring at room temperature for 22 hours. A 1 N aqueous sodium hydroxide solution was added to the reaction solution for neutralization, and subsequently water was further added, followed by extraction with a methanol/chloroform=20% mixed solution. The extract was dried over anhydrous sodium sulfate, and the solvent was distilled off under reduced pressure. The resulting residue was purified by flash chromatography (methanol/chloroform=0%→5%) using silica gel column chromatography (FLASH+ Cartridge 40S, manufactured by Biotage, Ltd.) to afford the mixture (0.188 g) of the title compound.

$^1$H-NMR (CDCl$_3$) δ: 2.37-2.47 (3H, m), 2.63 (3H, s), 5.34 (2H, s), 7.39-7.46 (2H, m), 7.51-7.59 (1H, m), 8.00-8.07 (2H, m).
MS (ESI) m/z: 259 [(M+H)$^+$].
Anal. Calcd for C$_{14}$H$_{14}$N$_2$O$_3$·0.15H$_2$O: C, 64.43; H, 5.52; N, 10.73.
Found: C, 64.43; H, 5.49; N, 10.66.

Example 48

Dimethyl carbamic acid (2-acetyl-1H-imidazol-4-yl)methylester, and dimethyl carbamic acid (2-acetyl-3H-imidazol-4-yl)methylester (1) 5-(tert-Butyldiphenylsilyloxymethyl)-1-(2-trimethylsilylethoxymethyl)-1H-imidazole

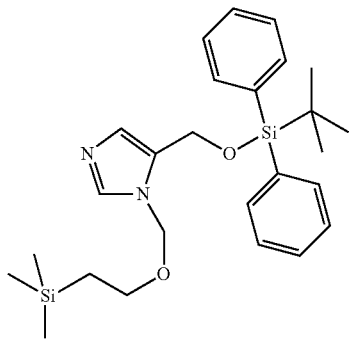

[Chemical 63]

In analogy to the method of Step (3) of Example 1, but from 5-hydroxymethyl-1-(2-trimethylsilylethoxymethyl)-1H-imidazole (73.5 g) and TBDPSCl (117 g), the title compound (150 g) was afforded.

$^1$H-NMR (CDCl$_3$) δ: −0.04 (9H, s), 0.88 (2H, t, J=8.2 Hz), 1.03 (9H, s), 3.46 (2H, t, J=8.2 Hz), 4.72 (2H, s), 5.40 (2H, s), 6.81 (1H, s), 7.36-7.47 (6H, m), 7.54 (1H, s), 7.70-7.65 (4H, m).

(2) 1-[5-(tert-Butyldiphenylsilyloxymethyl)-1-(2-trimethylsilylethoxymethyl)-1H-imidazol-2-yl]ethanone

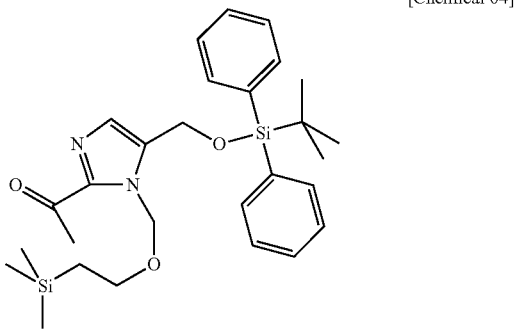

[Chemical 64]

In analogy to Step (4) of Example 1, but using the compound (38.0 g) obtained in (1), the title compound (29.4 g) was afforded.

$^1$H-NMR (CDCl$_3$) δ: −0.06 (9H, s), 0.82 (2H, t, J=8.7 Hz), 1.04 (9H, s), 2.67 (2H, s), 3.45-3.51 (2H, m), 4.78 (1H, s), 5.90 (1H, s), 6.96 (OH, s), 7.36-7.48 (6H, m), 7.67-7.64 (4H, m).
MS (ESI) m/z: 509 [(M+H)$^+$].

(3) 1-[5-Hydroxymethyl-1-(2-trimethylsilylethoxymethyl)-1H-imidazol-2-yl]ethanone

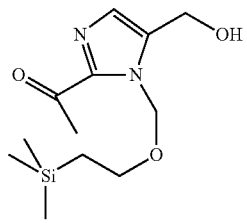

[Chemical 65]

In analogy to Step (5) of Example 1, but using the compound (29.4 g) obtained in (2), the title compound (15.6 g) was afforded.

$^1$H-NMR (CDCl$_3$) δ: −0.02 (9H, s), 0.88-0.93 (2H, m), 2.69 (3H, s), 3.58-3.62 (2H, m), 4.69 (2H, d, J=6.9 Hz), 5.98 (2H, s), 7.17 (1H, s).
MS (ESI) m/z: 271 [(M+H)$^+$].

(4) Dimethyl carbamic acid [2-acetyl-1-(2-trimethyl-silyl-ethoxymethyl)-3H-imidazol-4-yl]methylester

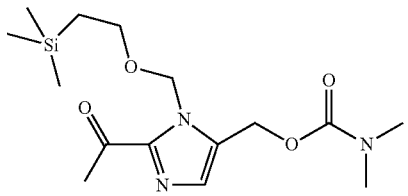

[Chemical 66]

After the compound (1.20 g) obtained in (3) was dissolved in DMF (20 mL), dimethylcarbamoyl chloride (0.433 mL) was added under stirring, and under ice cooling and stirring sodium hydride (0.235 g) was added in small portions to gradually raise the temperature, followed by stirring at room temperature for 2 hours. To this reaction solution, under ice cooling, was added a saturated aqueous ammonium chloride solution (5 mL), followed by stirring for a while. Water was further added to the reaction solution, followed by extraction with ethyl acetate. The extract was washed with saturated brine, dried over anhydrous sodium sulfate, and subsequently the solvent was distilled off under reduced pressure. The resulting residue was purified by flash chromatography (ethyl acetate/hexane=10%→70%) using silica gel column (product name: FLASH+ Cartridge KP-Sil 40M, manufactured by Biotage, Ltd.) to afford the title compound (0.896 g).

$^1$H-NMR (CDCl$_3$) δ: −0.03 (9H, s), 0.88 (2H, dd, J=8.2, 8.7 Hz), 2.68 (3H, s), 2.88 (3H, s), 2.92 (3H, s), 3.55 (2H, dd, J=8.2, 8.7 Hz), 5.22 (2H, s), 5.91 (2H, s), 7.22 (1H, s).
MS (ESI) m/z: 342 [(M+H)$^+$].

(5) Dimethyl carbamic acid (2-acetyl-1H-imidazol-4-yl)methylester and dimethyl carbamic acid (2-acetyl-3H-imidazol-4-yl)methylester

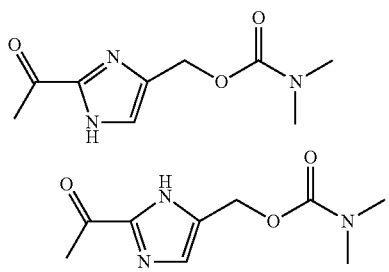

[Chemical 67]

The compound (0.896 g) obtained in (4) was dissolved in 4 N hydrochloric acid (5.00 mL), followed by stirring at room temperature for 27 hours. A 1 N aqueous sodium hydroxide solution was added to the reaction solution for neutralization, and subsequently water was further added, followed by extraction with a methanol/chloroform=20% mixed solution. The extract was dried over anhydrous sodium sulfate, and the solvent was distilled off under reduced pressure. The resulting residue was purified by flash chromatography (methanol/chloroform=0%→8%) using silica gel column (FLASH+ Cartridge 40S, manufactured by Biotage, Ltd.) to afford the mixture (0.412 g) of the title compound.

$^1$H-NMR (CD$_3$OD) δ: 2.55 (3H, s), 2.90 (6H, s), 5.07 (2H, s), 7.36 (1H, s).
MS (ESI) m/z: 212 [(M+H)$^+$].
Anal. Calcd for C$_9$H$_{13}$N$_3$O$_3$.0.1H$_2$O: C, 50.75; H, 6.25; N, 19.73.
Found: C, 50.65; H, 6.17; N, 19.69.

Example 49

Piperidine-1-carboxylic acid (2-acetyl-1H-imidazol-4-yl)methylester, and piperidine-1-carboxylic acid (2-acetyl-3H-imidazol-4-yl)methylester (1) Piperidine-1-carboxylic acid [2-acetyl-1-(2-trimethylsilylethoxymethyl)-1H-imidazol-4-yl]methylester

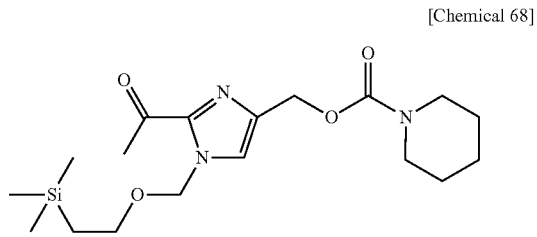 [SMILES: CC(=O)c1nc(COC(=O)N2CCCCC2)cn1COCC[Si](C)(C)C]

[Chemical 68]

In analogy to Step (4) of Example 48, but using 1-(4-hydroxymethyl-1-(2-trimethylsilylethoxymethyl)-1H-imidazol-2-yl)ethanone (1.50 g) and piperidine-1-ylcarbonyl chloride (0.763 mL), the title compound (1.93 g) was afforded.

$^1$H-NMR (CDCl$_3$) δ: −0.02 (9H, s), 0.93 (2H, dd, J=8.2, 8.7 Hz), 1.46-1.61 (6H, m), 2.67 (3H, s), 3.40-3.45 (4H, m), 3.57 (2H, dd, J=8.2, 8.7 Hz), 5.10 (2H, s), 5.73 (2H, s), 7.34 (1H, s).
MS (ESI) m/z: 382 [(M+H)$^+$].

(2) Piperidine-1-carboxylic acid (2-acetyl-1H-imidazol-4-yl)methylester, and piperidine-1-carboxylic acid (2-acetyl-3H-imidazol-4-yl)methylester

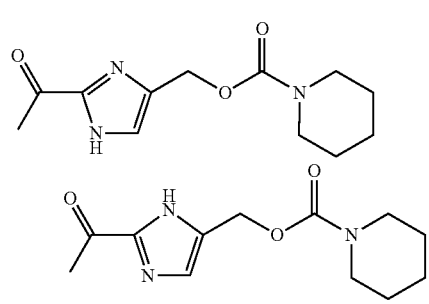

[Chemical 69]

In analogy to Step (5) of Example 48, but using the compound (1.93 g) obtained in (1), the mixture (0.748 g) of the title compound was afforded.

$^1$H-NMR (CD$_3$OD) δ: 1.46-1.65 (6H, m), 2.56 (3H, s), 3.40-3.45 (4H, m), 5.07 (2H, s), 7.35 (1H, s).
MS (ESI) m/z: 252 [(M+H)$^+$].
Anal. Calcd for C$_{12}$H$_{17}$N$_3$O$_3$.0.25H$_2$O: C, 56.35; H, 6.90; N, 16.43.
Found: C, 56.11; H, 6.69; N, 16.24.

Example 55

Succinic acid mono(2-acetyl-1H-imidazol-4-yl)methylester hydrochloride, and succinic acid mono(2-acetyl-3H-imidazol-4-yl)methylester hydrochloride (1) Succinic acid (2-acetyl-1H-imidazol-4-yl)methyl tert-butyl ester, and succinic acid (2-acetyl-3H-imidazol-4-yl)methyl tert-butyl ester

[Chemical 70]

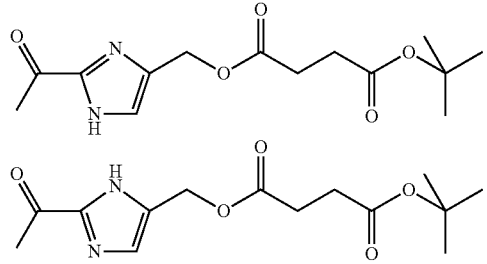

In analogy to Step (4) of Example 41, but using the mixture (1.79 g) obtained in Example 2 and succinic acid mono-tert-butyl ester (2.44 g), the mixture (3.58 g) of the title compound was afforded.

$^1$H-NMR (CD$_3$OD) δ: 1.40 (9H, s), 2.50-2.60 (7H, m), 5.11 (2H, s), 7.32 (1H, s).

(2) Succinic acid mono(2-acetyl-1H-imidazol-4-yl)methylester hydrochloride, and succinic acid mono(2-acetyl-3H-imidazol-4-yl)methylester hydrochloride

[Chemical 71]

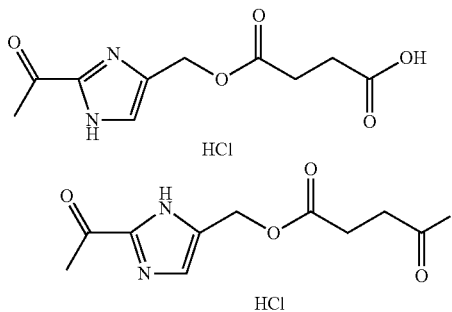

The compound (3.58 g) obtained in (1) was dissolved in a 4 N hydrochloric acid/1,4-dioxane solution, followed by stirring at room temperature for 16 hours. The solvent of the reaction solution was distilled off under reduced pressure, and the resulting residue was washed with ethyl acetate and hexane, and subsequently dried under reduced pressure at 40° C. to afford the mixture (2.73 g) of the title compound.

$^1$H-NMR (CD$_3$OD) δ: 1.74 (2H, s), 2.61-2.72 (5H, m), 5.17-5.29 (2H, m), 7.53-7.81 (1H, m).

MS (ESI) m/z: 241 [(M+H)$^+$].

Anal. Calcd for C$_{10}$H$_{12}$N$_2$O$_5$.HCl: C, 43.41; H, 4.74; N, 10.13; Cl, 12.81. Found: C, 43.01; H, 4.81; N, 10.10; Cl, 12.75.

Example 56

Salicylic acid (2-acetyl-1H-imidazol-4-yl)methylester, and salicylic acid (2-acetyl-3H-imidazol-4-yl)methylester (1) Salicylic acid (2-acetyl-1-dimethylsulfamoyl-1H-imidazol-4-yl)methylester, and salicylic acid (2-acetyl-3-dimethylsulfamoyl-3H-imidazol-4-yl)methylester

[Chemical 72]

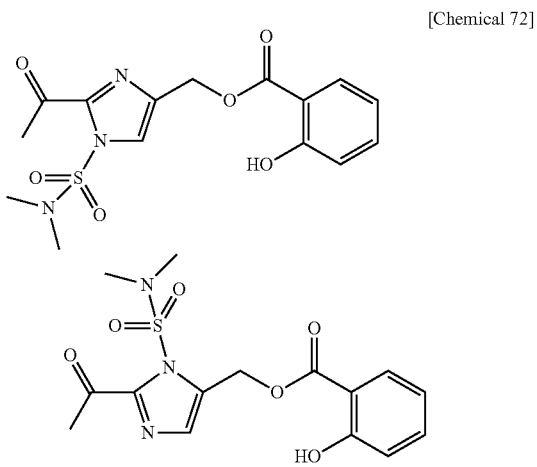

In analogy to Step (4) of Example 41, but using the mixture (1.50 g) of 2-acetyl-4-hydroxymethylimidazole-1-sulfonic acid dimethylamide and 2-acetyl-5-hydroxymethylimidazole-1-sulfonic acid dimethylamide and salicylic acid (0.922 g), the mixture (1.61 g) of the title compound was afforded.

MS (ESI) m/z: 368 [(M+H)$^+$].

(2) Salicylic acid (2-acetyl-1H-imidazol-4-yl)methylester, and salicylic acid (2-acetyl-3H-imidazol-4-yl)methylester

[Chemical 73]

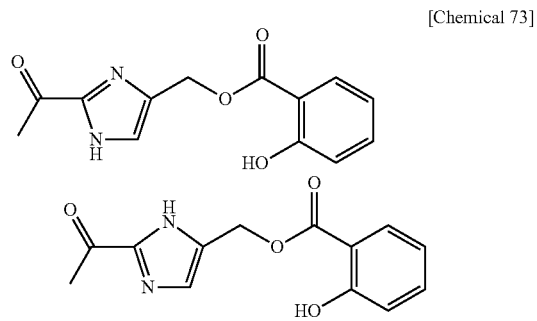

In analogy to Step (5) of Example 41, but using the compound (0.800 g) obtained in (1), the title compound (0.325 g) was afforded.

$^1$H-NMR (CD$_3$OD) δ: 2.58 (3H, s), 5.39 (2H, s), 6.88 (1H, dd, J=8.1, 7.8 Hz), 6.94 (1H, dd, J=8.1, 1.5 Hz), 7.45-7.51 (2H, m), 7.84 (1H, dd, J=7.8, 1.5 Hz).

MS (ESI) m/z: 261 [(M+H)+].

Anal. Calcd for $C_{13}H_{12}N_2O_4 \cdot 0.1H_2O$: C, 59.58; H, 4.69; N, 10.69. Found: C, 59.55; H, 4.81; N, 10.64.

Example 61

Succinic acid bis[(2-acetyl-1H-imidazol-4-yl)methyl]ester, succinic acid (2-acetyl-1H-imidazol-4-yl)methyl (2-acetyl-3H-imidazol-4-yl)methylester, and succinic acid bis[(2-acetyl-3H-imidazol-4-yl)methyl]ester (1) Succinic acid bis[(2-acetyl-1-dimethylsulfamoyl-1H-imidazol-4-yl)methyl]ester, succinic acid (2-acetyl-1-dimethylsulfamoyl-1H-imidazol-4-yl)methyl (2-acetyl-3-dimethylsulfamoyl-3H-imidazol-4-yl)methylester, and succinic acid bis[(2-acetyl-3-dimethylsulfamoyl-3H-imidazol-4-yl)methyl]ester

[Chemical 74]

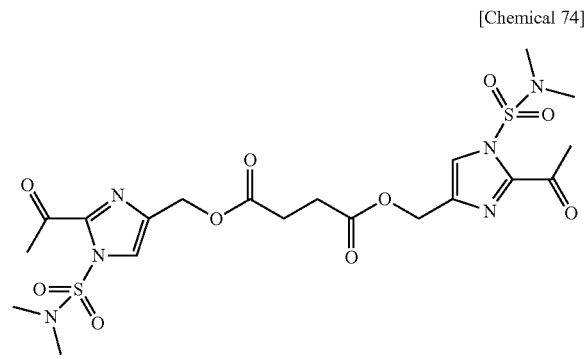

In analogy to Step (4) of Example 41, but using the mixture (2.00 g) of 2-acetyl-4-hydroxymethylimidazole-1-sulfonic acid dimethylamide and 2-acetyl-5-hydroxymethylimidazole-1-sulfonic acid dimethylamide and succinic acid (0.478 g), the mixture (1.40 g) of the title compound was afforded.

MS (ESI) m/z: 577 [(M+H)+].

(2) Succinic acid bis[(2-acetyl-1H-imidazol-4-yl)methyl]ester, succinic acid (2-acetyl-1H-imidazol-4-yl)methyl (2-acetyl-3H-imidazol-4-yl)methylester, and succinic acid bis[(2-acetyl-3H-imidazol-4-yl)methyl]ester

[Chemical 75]

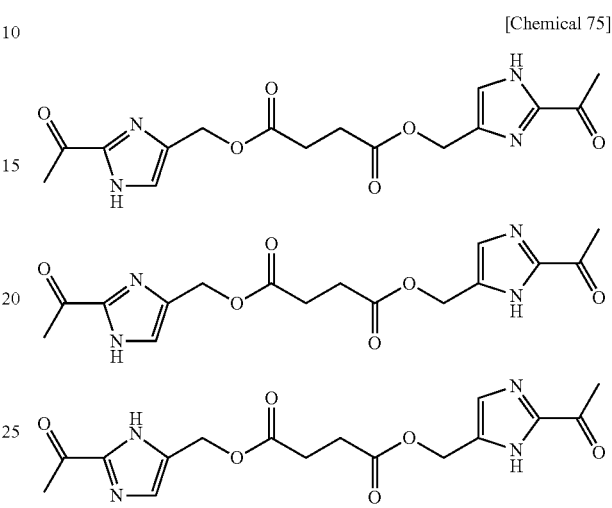

In analogy to Step (5) of Example 41, but using the mixture (1.40 g) obtained in (1), the mixture (0.531 g) of the title compound was afforded.

$^1$H-NMR (CD$_3$OD) δ: 2.55 (6H, s), 2.66 (4H, s), 5.08 (4H, s), 7.34 (2H, s).

MS (ESI) m/z: 363 [(M+H)+].

Anal. Calcd for $C_{16}H_{18}N_4O_6 \cdot 0.1H_2O$ C, 52.51; H, 5.01; N, 15.31. Found: C, 52.55; H, 4.92; N, 15.40.

Example 68 cis-Cyclohexane-1,3-dicarboxylic acid bis[(2-acetyl-1H-imidazol-4-yl)methyl]ester, cis-cyclohexane-1,3-dicarboxylic acid bis[(2-acetyl-3H-imidazol-4-yl)methyl]ester, and cis-cyclohexane-1,3-dicarboxylic acid 1-(2-acetyl-1H(3H)-imidazol-4-yl)methyl 3-(2-acetyl-3H(1H)-imidazol-4-yl)methylester

[Chemical 76]

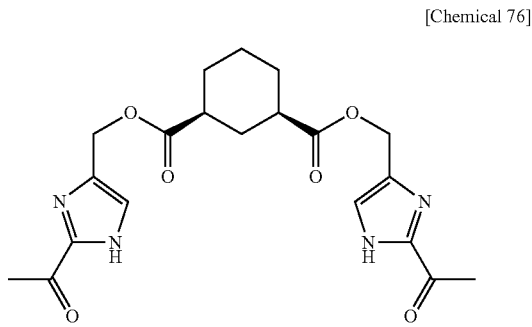

-continued

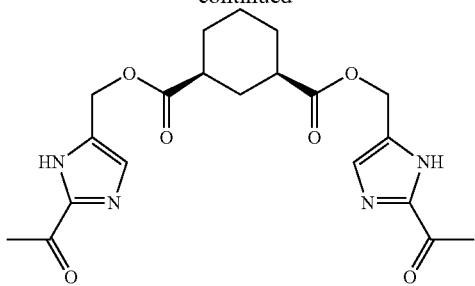

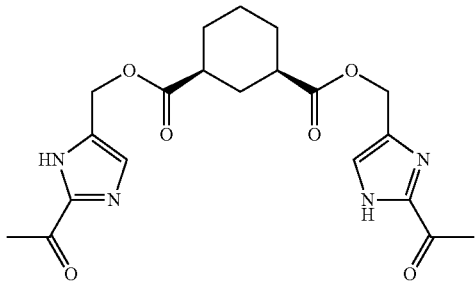

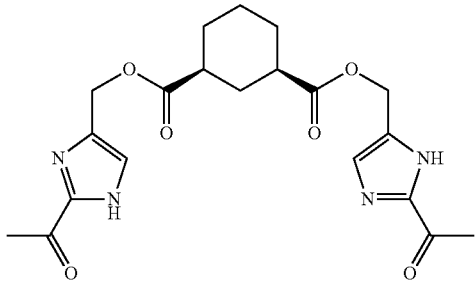 [SMILES: CC(=O)c1ncc(COC(=O)C2CCCC(C(=O)OCc3cnc(C(C)=O)[nH]3)C2)[nH]1]

In analogy to the method of Step (4) of Example 41, but from the mixture (2.00 g) obtained in Example 2 and cis-cyclohexane-1,3-dicarboxylic acid (680 mg), the mixture (1.13 g) of the title compound was afforded.

$^1$H-NMR (CD$_3$OD) δ: 1.23-1.53 (4H, m), 1.82-2.21 (4H, m), 2.33-2.45 (2H, m), 2.55 (6H, s), 5.08 (4H, s), 7.35 (2H, s).

MS (ESI) m/z: 417 [(M+H)$^+$].

Anal. Calcd for C$_{20}$H$_{24}$N$_4$O$_6$: C, 57.68; H, 5.81; N, 13.45. Found: C, 57.54; H, 5.85; N, 13.39.

Example 75

(2S,5S)-Pyrrolidine-2,5-dicarboxylic acid 2-(2-acetyl-1H-imidazol-4-yl)methyl 5-methylester hydrochloride, and (2S,5S)-pyrrolidine-2,5-dicarboxylic acid 2-(2-acetyl-3H-imidazol-4-yl)methyl 5-methylester hydrochloride

[Chemical 77]

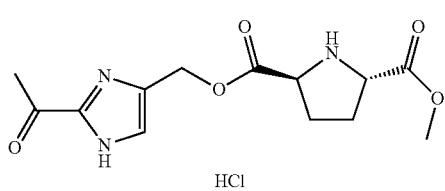

-continued

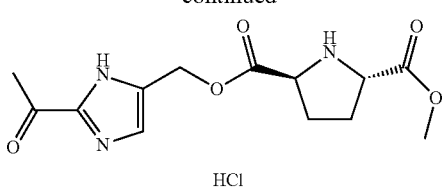

The mixture (1.43 g) obtained in Example 74 described later was dissolved in a 4 N hydrochloric acid/1,4-dioxane solution (60 mL), followed by stirring at room temperature for 17 hours. The reaction solution was concentrated to afford the mixture (1.46 g) of the title compound.

$^1$H-NMR (DMSO-D$_6$) δ: 2.05-2.17 (2H, m), 2.29-2.39 (3H, m), 2.54 (3H, s), 3.76 (3H, s), 4.49-4.57 (2H, m), 5.22 (2H, s), 7.58 (1H, s), 10.11 (1H, s).

MS (ESI) m/z: 296 [(M+H)$^+$].

Example 76

2,2-Dimethylpropionic acid (2-acetyl-4-hydroxymethylimidazol-1-yl)methylester (1) 1-[4-(tert-Butyldimethylsilyloxymethyl)-1H-imidazol-2-yl]ethanone, and 1-[5-(tert-butyldimethylsilyloxymethyl)-1H-imidazol-2-yl]ethanone

[Chemical 78]

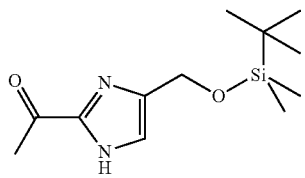

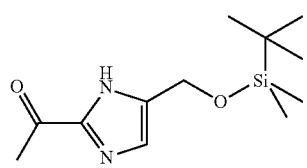

The mixture (8.81 g) obtained in Example 2 was dissolved in THF (200 mL), and at room temperature TEA (52.6 mL) and tert-butylchlorodimethylsilane (19.0 g) were added, followed by stirring for 20 hours. The reaction solution was poured into water, followed by extraction with ethyl acetate. The extract was washed with saturated brine, subsequently dried over anhydrous sodium sulfate, and the solvent was distilled off under reduced pressure. The resulting residue was purified by flash chromatography (ethyl acetate/hexane=10%→50%) using silica gel column (product name: Hi-Flash Column 3 L, manufactured by Yamazen Corporation) to afford the mixture (13.5 g) of the title compound.

(2) 2,2-Dimethylpropionic acid [2-acetyl-4-(tert-butyldimethylsilyloxymethyl)imidazol-1-yl]methylester, and 2,2-dimethylpropionic acid [2-acetyl-5-(tert-butyldimethylsilyloxymethyl)imidazol-1-yl]methylester  [Chemical 79]

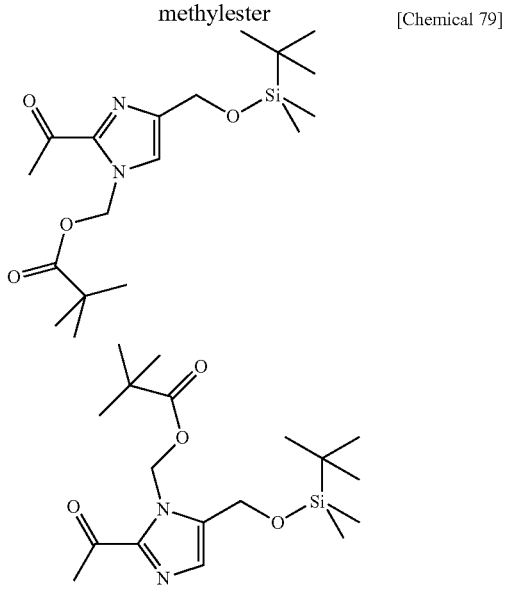

The mixture (1.50 g) obtained in (1) was dissolved in acetonitrile (200 mL), and at room temperature TEA (8.22 mL) and chloromethyl pivalate (3.43 mL) were added, which mixture was warmed to 50° C., followed by stirring for 3 days. The temperature of the reaction solution was brought back to room temperature, and subsequently poured into water, followed by extraction with ethyl acetate. The extract was washed with saturated brine, subsequently dried over anhydrous sodium sulfate, and the solvent was distilled off under reduced pressure. The resulting residue was purified by flash chromatography (ethyl acetate/hexane=5%→35%) using silica gel column (product name: Hi-Flash Column 3 L, manufactured by Yamazen Corporation) to afford 2,2-dimethylpropionic acid [2-acetyl-4-(tert-butyldimethylsilyloxymethyl)imidazol-1-yl]methylester (1.83 g) as a low polar fraction and 2,2-dimethylpropionic acid [2-acetyl-5-(tert-butyldimethylsilyloxymethyl)imidazol-1-yl]methylester (50.0 mg) as a high polar fraction.

2,2-Dimethylpropionic acid [2-acetyl-4-(tert-butyldimethylsilyloxymethyl)imidazol-1-yl]methylester $^1$H-NMR (CDCl$_3$) δ: 0.10 (6H, s), 0.93 (9H, s), 1.17 (9H, s), 2.65 (3H, s), 4.71 (2H, s), 6.26 (2H, s), 7.20 (1H, s).

2,2-Dimethylpropionic acid [2-acetyl-5-(tert-butyldimethylsilyloxymethyl)imidazol-1-yl]methylester $^1$H-NMR (CDCl$_3$) δ: 0.09 (6H, s), 0.89 (9H, s), 1.16 (9H, s), 2.66 (3H, s), 4.77 (2H, s), 6.34 (2H, s), 7.06 (1H, s).

(3) 2,2-Dimethylpropionic acid (2-acetyl-4-hydroxymethylimidazol-1-yl)methylester

[Chemical 80]

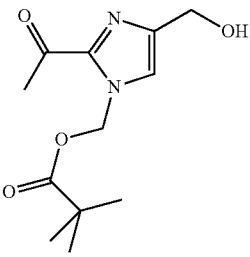

2,2-Dimethylpropionic acid [2-acetyl-4-(tert-butyldimethylsilyloxymethyl)imidazol-1-yl]methylester (1.50 g) was dissolved in THF (50 mL), and at room temperature acetic acid (1 mL) and TBAF (1.0 M THF solution, 4.97 mL) were added, followed by stirring for 4 hours. The reaction solution was concentrated, and the resulting residue was purified by flash chromatography (ethyl acetate/hexane=100%→100%) using silica gel column (product name: Hi-Flash Column 3 L, manufactured by Yamazen Corporation) to afford the title compound (1.10 g).

$^1$H-NMR (CDCl$_3$) δ: 1.17 (9H, s), 2.67 (3H, s), 4.65 (2H, s), 6.25 (2H, s), 7.25 (1H, s).
MS (ESI) m/z: 255 [(M+H)$^+$].
Anal. Calcd for C$_{12}$H$_{18}$N$_2$O$_4$: C, 56.68; H, 7.13; N, 11.02. Found: C, 56.61; H, 7.16; N, 11.03.

Example 79

Isobutyric acid (2-acetyl-4-hydroxymethylimidazol-1-yl)methylester (1) Isobutyric acid [2-acetyl-4-(tert-butyldimethylsilyloxymethyl)imidazol-1-yl]methylester

[Chemical 81]

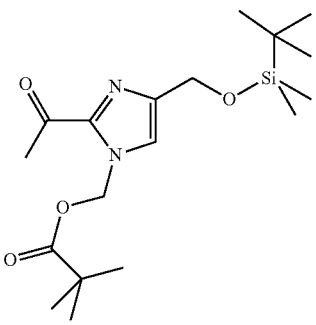

In analogy to the method of Step (2) of Example 76, but from [4-(tert-butyldimethylsilyloxymethyl)-1H-imidazol-2-yl]ethanone (2.00 g) and chloromethyl isobutyrate (Bioorganic & Medicinal Chemistry Letters, 2009, 1409-1412, 19, 11.0 g), the title compound (1.05 g) was afforded.

$^1$H-NMR (CDCl$_3$) δ: 0.10 (6H, s), 0.93 (9H, s), 1.14 (3H, d, J=7.3 Hz), 1.14 (3H, d, J=7.3 Hz), 2.46-2.61 (1H, m), 2.65 (3H, s), 4.71 (2H, s), 6.27 (2H, s), 7.21 (1H, s).
MS (ESI) m/z: 355 [(M+H)$^+$].

(2) Isobutyric acid (2-acetyl-4-hydroxymethylimidazol-1-yl)methylester

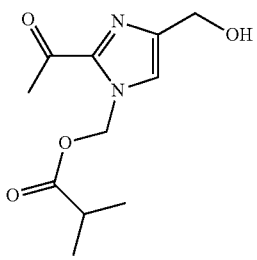

[Chemical 82]

In analogy to the method of Step (3) of Example 76, but from isobutyric acid [2-acetyl-4-(tert-butyldimethylsilyloxymethyl)imidazol-1-yl]methylester (1.05 g), the title compound (550 mg) was afforded.

$^1$H-NMR (CDCl$_3$) δ: 1.15 (6H, d, J=6.4 Hz), 2.06-2.13 (1H, m), 2.50-2.61 (1H, m), 2.67 (3H, s), 4.65 (2H, d, J=4.6 Hz), 6.27 (2H, s), 7.26 (1H, s).
MS (ESI) m/z: 241 [(M+H)$^+$].
Anal. Calcd for C$_{11}$H$_{16}$N$_2$O$_4$: C, 54.99; H, 6.71; N, 11.66. Found: C, 54.68; H, 6.80; N, 11.55.

Example 80

1-[4-(Tetrahydrofuran-2-yloxymethyl)-1H-imidazol-2-yl]ethanone and 1-[5-(tetrahydrofuran-2-yloxymethyl)-1H-imidazol-2-yl]ethanone

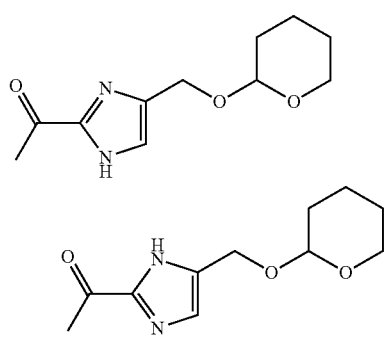

[Chemical 83]

The mixture (2.00 g) obtained in Example 2 was dissolved in dichloromethane (100 mL), and at room temperature 2,3-dihydropyrane (2.58 mL) and p-toluenesulfonic acid monohydrate (2.71 g) were added, followed by stirring for 5 days. The reaction solution was diluted with chloroform, and washed with saturated sodium bicarbonate water and saturated brine in this order. The extract was dried over anhydrous sodium sulfate, and the solvent was distilled off under reduced pressure. The resulting residue was purified by flash chromatography (ethyl acetate/hexane=10%→60%) using silica gel column (product name: SNAP Cartridge KP-Sil 100 g, manufactured by Biotage, Ltd.) to afford the mixture (1.55 g) of the title compound.

$^1$H-NMR (CDCl$_3$) δ: 1.49-1.65 (4H, m), 1.72-1.90 (2H, m), 2.63 and 2.65 (total 3H, each s), 3.53-3.60 (1H, m), 3.87-3.96 (1H, m), 4.51-4.83 (3H, m), 7.12 and 7.22 (total 1H, each s).

MS (ESI) m/z: 225 [(M+H)$^+$].
Anal. Calcd for C$_{11}$H$_{16}$N$_2$O$_3$: C, 58.91; H, 7.19; N, 12.49. Found: C, 59.03; H, 7.28; N, 12.42.

Example 81

1-(4-Methoxymethoxymethyl-1-methoxymethyl-1H-imidazol-2-yl)ethanone

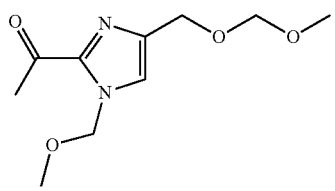

[Chemical 84]

The mixture (0.500 g) obtained in Example 2 was dissolved in dichloromethane (20 mL), and at room temperature TEA (2.43 mL) and chloromethylmethylether (0.540 mL) were added, followed by stirring for 4 days. The reaction solution was concentrated, and the resulting residue was purified by flash chromatography (ethyl acetate/hexane=20%→100%) using silica gel column (product name: Hi-Flash Column 3 L, manufactured by Yamazen Corporation) to afford the title compound (560 mg).

$^1$H-NMR (CDCl$_3$) δ: 2.68 (3H, s), 3.35 (3H, s), 3.43 (3H, s), 4.59 (2H, s), 4.75 (2H, s), 5.71 (2H, s), 7.27 (1H, s).

Example 82

1-(4-Hydroxymethyl-1H-imidazol-2-yl)ethanone oxime, and 1-(5-hydroxymethyl-1H-imidazol-2-yl)ethanone oxime

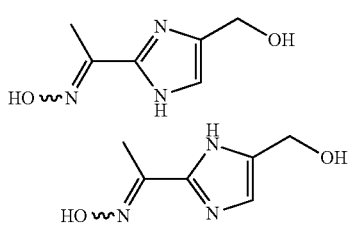

[Chemical 85]

The mixture (1.00 g) of 1-(4-hydroxymethyl-1H-imidazol-2-yl)ethanone and 1-(5-hydroxymethyl-1H-imidazol-2-yl)ethanone was dissolved in water (20 mL), and at room temperature hydroxylammonium chloride (600 mg) and sodium acetate (1.17 g) were added, which mixture was subsequently warmed at 50° C., followed by stirring for 14 hours. The reaction solution was concentrated to obtain the residue, to which methanol/ethyl acetate was added, and the precipitated insolubles were filtered off. The resulting mother liquor was concentrated, and recrystallized with ethyl acetate/hexane to afford the mixture (1.73 g) of the title compound.

$^1$H-NMR (CD$_3$OD) δ: 2.21 and 2.24 (total 3H, each s), 4.54-4.55 and 4.60 (total 2H, m and s), 6.99 and 7.13 (total 1H, each s).
MS (ESI) m/z: 156 [(M+H)$^+$].

Example 83

(2-Isoxazol-3-yl-1H-imidazol-4-yl)methanol and (2-isoxazol-3-yl-3H-imidazol-4-yl)methanol (1) 1-[5-(tert-Butyldiphenylsilyloxymethyl)-1-(2-trimethylsilylethoxymethyl)-1H-imidazol-2-yl]ethanone oxime

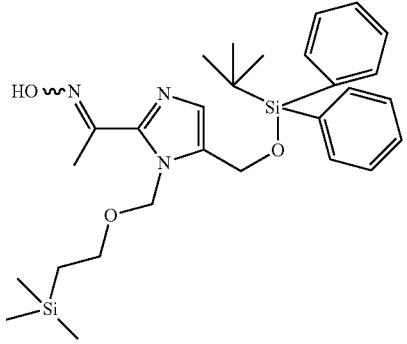

[Chemical 86]

1-[5-(tert-Butyldiphenylsilyloxymethyl)-1-(2-trimethylsilylethoxymethyl)-1H-imidazol-2-yl]ethanone (60.0 g) was dissolved in methanol (600 mL), and at room temperature hydroxylammonium chloride (16.4 g) and sodium acetate (24.2 g) were added, which mixture was subsequently warmed at 50° C., followed by stirring for 7 hours. After the reaction solution was cooled to room temperature, the insolubles were removed by filtration, and the mother liquor was concentrated to obtain the residue, which was purified by flash chromatography (ethyl acetate/hexane=10%→60%) using silica gel column (product name: Hi-Flash Column 5 L, manufactured by Yamazen Corporation) to afford the title compound (13.5 g).

$^1$H-NMR (CDCl$_3$) δ: −0.06 (9H, s), 0.83 (3H, t, J=8.3 Hz), 1.03 (9H, s), 2.39 (3H, s), 3.45 (2H, t, J=8.3 Hz), 4.75 (2H, s), 5.81 (2H, s), 7.33-7.47 (6H, m), 7.64-7.68 (4H, m).

MS (ESI) m/z: 524 [(M+H)$^+$].

(2) 3-[5-(tert-Butyldiphenylsilyloxymethyl)-1-(2-trimethylsilylethoxymethyl)-1H-imidazol-2-yl]isoxazole

[Chemical 87]

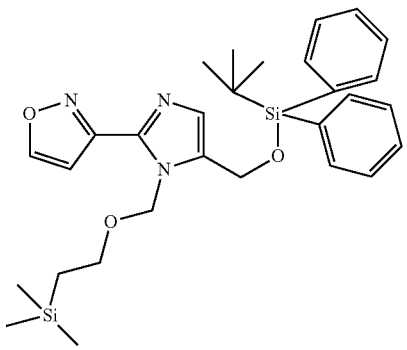

The compound (58.5 g) obtained in (1) was dissolved in THF (1000 mL), and cooled to −20° C. while stirring under nitrogen stream. To the present solution was added dropwise n-butyl lithium (2.66 M hexane solution, 210 mL), followed by stirring at the same temperature for 30 minutes. Then, DMF (51.9 mL) was added, followed by stirring at the same temperature for 4 hours. A saturated aqueous ammonium chloride solution was added to the reaction solution at the same temperature to terminate the reaction. The temperature of the reaction solution was brought back to room temperature, followed by extraction with ethyl acetate. The extract was washed with saturated brine, and subsequently dried over anhydrous sodium sulfate. The solvent was distilled off under reduced pressure to afford the crude product of 3-[5-(tert-butyldiphenylsilyloxymethyl)-1-(2-trimethylsilylethoxymethyl)-1H-imidazol-2-yl]-4,5-dihydro-5-isoxazole, which was then subjected to the next step.

The crude product of 3-[5-(tert-butyldiphenylsilyloxymethyl)-1-(2-trimethylsilylethoxymethyl)-1H-imidazol-2-yl]-4,5-dihydro-5-isoxazole obtained in the previous step was dissolved in THF (500 mL), and cooled to 0° C. while stirring under nitrogen stream. To the present solution were added pyridine (45.2 mL) and trifluoroacetic acid anhydride (62.1 mL), followed by stirring for 30 minutes. The present reaction solution was stirred for 1.5 hours while bringing back to room temperature, and further warmed to 55° C., followed by stirring for 2 hours. The temperature of the reaction solution was brought back to room temperature, and subsequently poured into water, followed by extraction with ethyl acetate. The extract was washed with saturated brine, subsequently dried over anhydrous sodium sulfate, and the solvent was distilled off under reduced pressure. The resulting residue was purified by flash chromatography (ethyl acetate/hexane=10%→60%) using silica gel column (product name: Hi-Flash Column 5 L, manufactured by Yamazen Corporation) to afford the title compound (14.5 g).

$^1$H-NMR (CDCl$_3$) δ: −0.10 (9H, s), 0.84 (3H, t, J=8.6 Hz), 1.05 (8H, s), 3.51 (2H, t, J=8.3 Hz), 4.82 (2H, s), 5.99 (2H, s), 6.96 (1H, s), 6.98 (1H, d, J=2.3 Hz), 7.37-7.47 (6H, m), 7.71-7.66 (4H, m), 8.45 (1H, d, J=1.1 Hz).

MS (ESI) m/z: 534 [(M+H)$^+$].

(3) 2-(Isoxazol-3-yl)-1-(2-trimethylsilylethoxymethyl)-1H-imidazole-5-methanol

[Chemical 88]

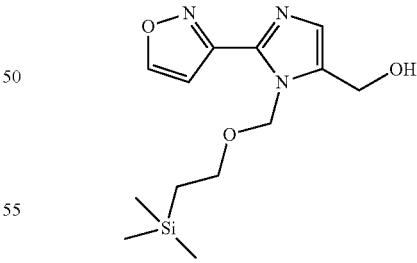

In analogy to the method of Step (3) of Example 76, but from 3-[5-(tert-butyldiphenylsilyloxymethyl)-1-(2-trimethylsilylethoxymethyl)-1H-imidazol-2-yl]isoxazole (15.6 g), the title compound (4.93 g) was afforded.

$^1$H-NMR (CDCl$_3$) δ: −0.06 (9H, s), 0.87-0.94 (2H, m), 2.90-2.97 (1H, m), 3.58-3.65 (2H, m), 4.72 (2H, d, J=5.0 Hz), 6.03 (2H, s), 6.98 (1H, d, J=1.8 Hz), 7.20 (1H, s), 8.46 (1H, d, J=1.8 Hz).

MS (ESI) m/z: 296 [(M+H)$^+$].

(4) (2-Isoxazol-3-yl-1H-imidazol-4-yl)methanol and (2-isoxazol-3-yl-3H-imidazol-4-yl)methanol

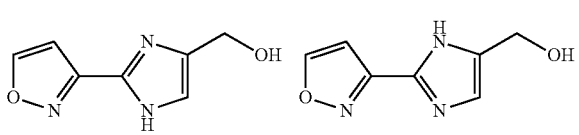
[Chemical 89]

The compound (4.93 g) obtained in (3) was dissolved in 4 N hydrochloric acid (80 mL), followed by stirring at 50° C. for 5 hours. The reaction solution was concentrated to obtain the residue, which was dissolved in methanol, and sodium hydrogen carbonate was added, followed by stirring for a while. The insolubles were removed by filtration, and the resulting mother liquor was concentrated. The resulting residue was purified by chromatography (methanol/chloroform=10%) using silica gel (product name: Silica Gel 60, manufactured by Merck, Ltd.) to afford the mixture (2.52 g) of the title compound.

$^1$H-NMR (CD$_3$OD) δ: 4.61 (2H, s), 6.91 (1H, s), 7.18 (1H, br s), 8.75-8.73 (1H, m).

MS (ESI) m/z: 166 [(M+H)$^+$].

Example 84

4-(2-Acetyl-1H-imidazol-4-ylmethoxymethyl)-5-methyl-[1,3]dioxol-2-one and 4-(2-acetyl-3H-imidazol-4-ylmethoxymethyl)-5-methyl-[1,3]dioxol-2-one (1) 2-Acetyl-4-[5-methyl-2-oxo-[1,3]dioxol-4-ylmethoxymethyl]imidazole-1-sulfonic acid dimethylamide, and 2-acetyl-5-[5-methyl-2-oxo-[1,3]dioxol-4-ylmethoxymethyl]imidazole-1-sulfonic acid dimethylamide

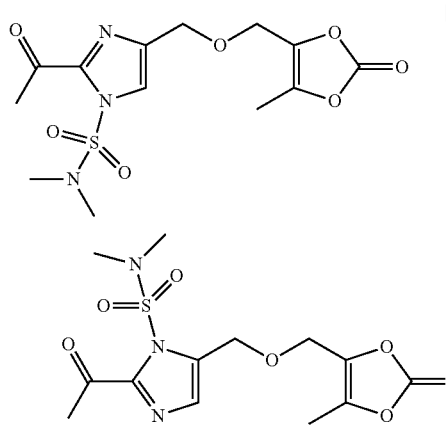
[Chemical 90]

The mixture (1.00 g) of 2-acetyl-4-hydroxymethylimidazole-1-sulfonic acid dimethylamide and 2-acetyl-5-hydroxymethylimidazole-1-sulfonic acid dimethylamide and 4-chloromethyl-5-methyl-1,3-dioxol-2-one (0.660 mL) were dissolved in DMF (30 mL), and potassium carbonate (1.12 g) was suspended, followed by stirring at room temperature for 3 hours. The present reaction solution was warmed to 45° C., followed by stirring for a further 3 hours. The temperature of the reaction solution was brought back to room temperature, and subsequently the insolubles were removed by filtration. The resulting filtrate was diluted with water, followed by extraction with ethyl acetate. The extract was washed with saturated brine, and subsequently dried over anhydrous sodium sulfate. The extract was washed with saturated brine, subsequently dried over anhydrous sodium sulfate, and the solvent was distilled off under reduced pressure. The resulting residue was purified by flash chromatography (ethyl acetate/hexane=10%→100%) using silica gel column (product name: SNAP Cartridge KP-Sil 100 g, manufactured by Biotage, Ltd.) to afford the mixture (0.550 g) of the title compound.

$^1$H-NMR (CDCl$_3$) δ: 2.37-2.38 (3H, m), 2.66-2.67 (3H, m), 3.09 and 3.15 (total 6H, each s), 5.18 and 5.44 (total 2H, s and d, J=0.9 Hz), 5.76 and 5.95 (total 2H, d and dd, J=2.8 and 5.0, 2.8 Hz, respectively), 7.19 and 7.68 (total 1H, each s).

MS (ESI) m/z: 360 [(M+H)$^+$].

(2) 4-(2-Acetyl-1H-imidazol-4-ylmethoxymethyl)-5-methyl-[1,3]dioxol-2-one and 4-(2-acetyl-3H-imidazol-4-ylmethoxymethyl)-5-methyl-[1,3]dioxol-2-one

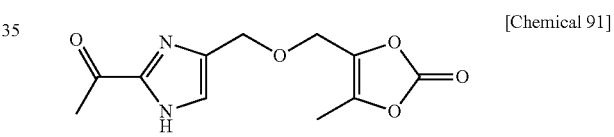
[Chemical 91]

The mixture (0.550 g) obtained in (1) was dissolved in 1 N hydrochloric acid (10 mL), followed by stirring at room temperature for 1 hour, and further warmed to 50° C., followed by stirring for 2 hours. The temperature of the reaction solution was brought back to room temperature, purified by reversed phase preparative HPLC, and subsequently lyophilized to afford the mixture (170 mg) of the title compound.

$^1$H-NMR (CD$_3$OD) δ: 2.35 (3H, s), 2.57 (3H, s), 5.19 (2H, s), 5.78 (1H, d, J=3.2 Hz), 6.09 (1H, d, J=2.8 Hz), 7.43 (1H, s).

MS (ESI) m/z: 253 [(M+H)$^+$].

In analogy to the above-mentioned Examples, or using methods known in this field, the following compounds are afforded.

TABLE 4

| Example | Compound Name | Structural Formula | Physical Property Data |
|---|---|---|---|
| 36 | Cyclohexane carboxylic acid (2-acetyl-1H-imidazol-4-yl)methylester | | $^1$H-NMR (CD$_3$OD) δ: 1.18-1.35 (3H, m), 1.37-1.47 (2H, m), 1.60-1.66 (1H, m), 1.69-1.76 (2H, m), 1.84-1.91 (2H, m), 2.30-2.37 (1H, m), 2.55 (3H, s), 5.08 (2H, s), 7.31 (1H, br s). MS (ESI) m/z: 251 [(M + H)$^+$]. Anal. Calcd for C$_{13}$H$_{18}$N$_2$O$_3$: C, 62.83; H, 7.25; N, 11.19. Found: C, 62.04; H, 7.27; N, 11.09. |
| | Cyclohexane carboxylic acid (2-acetyl-3H-imidazol-4-yl)methylester | | |
| 37 | Cyclopentane carboxylic acid (2-acetyl-1H-imidazol-4-yl)methylester | | $^1$H-NMR (CD$_3$OD) δ: 1.53-1.92 (8H, m), 2.55 (3H, s), 3.30-3.32 (1H, m), 5.09 (2H, s), 7.32 (1H, br s). MS (ESI) m/z: 237 [(M + H)$^+$]. Anal. Calcd for C$_{12}$H$_{16}$N$_2$O$_3$: C, 61.00; H, 6.83; N, 11.86. Found: C, 60.88; H, 6.78; N, 11.78. |
| | Cyclopentane carboxylic acid (2-acetyl-3H-imidazol-4-yl)methylester | | |
| 38 | 2,2-Dimethylpropionic acid (2-acetyl-1H-imidazol-4-yl)methylester | | $^1$H-NMR (CD$_3$OD) δ: 1.19 (9H, s), 2.56 (3H, s), 5.08 (2H, s), 7.35 (1H, s). MS (ESI) m/z: 225 [(M + H)$^+$]. Anal. Calcd for C$_{11}$H$_{16}$N$_2$O$_3$: C, 58.91; H, 7.19; N, 12.49. Found: C, 58.50; H, 7.16; N, 12.44. |

TABLE 4-continued

| Example | Compound Name | Structural Formula | Physical Property Data |
|---|---|---|---|
| | 2,2-Dimethylpropionic acid (2-acetyl-3H-imidazol-4-yl)methylester | | |
| 39 | Naphthalene-2-carboxylic acid (2-acetyl-1H-imidazol-4-yl)methylester | | MS (ESI) m/z: 295 [(M + H)$^+$].<br>Anal. Calcd for $C_{17}H_{14}N_2O_3$: C, 69.38; H, 4.79; N, 9.52.<br>Found: C, 69.40; H, 4.85; N, 9.53. |
| | Naphthalene-2-carboxylic acid (2-acetyl-3H-imidazol-4-yl)methylester | | |

TABLE 5

| Example | Compound Name | Structural Formula | Physical Property Data |
|---|---|---|---|
| 40 | 2,4,6-Trimethyl benzoic acid (2-acetyl-1H-imidazol-4-yl)methylester | | MS (ESI) m/z: 287 [(M + H)$^+$].<br>Anal. Calcd for $C_{16}H_{18}N_2O_3$: C, 67.12; H, 6.34; N, 9.78.<br>Found: C, 66.99; H, 6.33; N, 9.79. |
| | 2,4,6-Trimethyl benzoic acid (2-acetyl-3H-imidazol-4-yl)methylester | | |

TABLE 5-continued

| Example | Compound Name | Structural Formula | Physical Property Data |
|---|---|---|---|
| 46 | Acetic acid (2-acetyl-5-methyl-1H-imidazol-4-yl)methylester | | $^1$H-NMR (CD$_3$OD) δ: 2.03 (3H, s), 2.31 (3H, s), 2.51 (3H, s), 5.05 (2H, s). MS (ESI) m/z: 197 [(M + H)$^+$]. Anal. Calcd for C$_9$H$_{12}$N$_2$O$_3$: C, 55.09; H, 6.16; N, 14.28. Found: C, 54.74; H, 6.13; N, 14.18. |
| | Acetic acid (2-acetyl-5-methyl-3H-imidazol-4-yl)methylester | | |
| 47 | Cyclopentane carboxylic acid (2-acetyl-5-methyl-1H-imidazol-4-yl)methylester | | $^1$H-NMR (CDC13) δ: 1.51-1.96 (8H, m), 2.31-2.39 (3H, m), 2.62 (3H, s), 2.71-2.82 (1H, m), 5.08 (2H, s), 10.52 (1H, br s). MS (ESI) m/z: 251 [(M + H)$^+$]. Anal. Calcd for C$_{13}$H$_{18}$N$_2$O$_3$•0.25H$_2$O: C, 61.28; H, 7.32; N, 10.99. Found: C, 61.70; H, 7.32; N, 10.59. |
| | Cyclopentane carboxylic acid (2-acetyl-5-methyl-3H-imidazol-4-yl)methylester | | |
| 50 | Morpholine-4-carboxylic acid (2-acetyl-1H-imidazol-4-yl)methylester | | $^1$H-NMR (CD$_3$OD) δ: 2.55 (3H, s), 3.45 (4H, t, J = 4.6 Hz), 3.61 (4H, br s), 5.10 (2H, s), 7.37 (1H, s). MS (ESI) m/z: 254 [(M + H)$^+$]. Anal. Calcd for C$_{11}$H$_{15}$N$_3$O$_4$•0.15H$_2$O: C, 51.62 H, 6.02; N, 16.42. Found: C, 51.53; H, 5.93; N, 16.39. |
| | Morpholine-4-carboxylic acid (2-acetyl-3H-imidazol-4-yl)methylester | | |
| 51 | Succinic acid (2-acetyl-1H-imidazol-4-yl)methylethyl ester | | $^1$H-NMR (CD$_3$OD) δ: 1.21 (3H, t, J = 7.1 Hz), 2.55 (3H, s), 2.58-2.66 (4H, m), 4.09 (2H, q, J = 7.1 Hz), 5.11 (2H, s), 7.35 (1H, s). MS (ESI) m/z: 269 [(M + H)$^+$]. Anal. Calcd for C$_{12}$H$_{16}$N$_2$O$_5$•0.25H$_2$O: C, 52.84; H, 6.10; N, 10.27. Found: C, 52.95; H, 6.02; N, 10.10. |
| | Succinic acid (2-acetyl-3H-imidazol-4-yl)methylethyl ester | | |

TABLE 6

| Example | Compound Name | Structural Formula | Physical Property Data |
|---|---|---|---|
| 52 | Terephthalic acid (2-acetyl-1H-imidazol-4-yl)methyl methylester | | $^1$H-NMR (CD3OD) δ: 2.57 (3H, s), 3.92 (3H, s), 5.37 (2H, s), 7.48 (1H, s), 8.08-8.13 (4H, m). Anal. Calcd for $C_{15}H_{14}N_2O_5 \cdot 0.5H_2O$: C, 57.88; H, 4.86; N, 9.00. Found: C, 57.91; H, 4.65; N, 8.90. |
| | Terephthalic acid (2-acetyl-3H-imidazol-4-yl)methyl methylester | | |
| 53 | Octanoic acid (2-acetyl-1H-imidazol-4-yl)methylester | | $^1$H-NMR (CD$_3$OD) δ: 0.87 (3H, t, J = 7.0 Hz), 1.20-1.32 (8H, m), 1.54-1.64 (2H, m), 2.33 (2H, t, J = 7.3 Hz), 2.55 (3H, s), 5.09 (2H, s), 7.31 (1H, br s). MS (ESI) m/z: 267 [(M + H)$_+$]. Anal. Calcd for $C_{14}H_{22}N_2O_3 \cdot 0.125H_2O$: C, 62.61; H, 8.35; N, 10.43. Found: C, 62.66; H, 8.34; N, 10.37. |
| | Octanoic acid (2-acetyl-3H-imidazol-4-yl)methylester | | |
| 54 | Pyrrolidine-1-carboxylic acid (2-acetyl-1H-imidazol-4-yl)methylester | | $^1$H-NMR (CD$_3$OD) δ: 1.84-1.90 (4H, m), 2.55 (3H, s), 3.33-3.37 (4H, m), 5.09 (2H, s), 7.36 (1H, s). MS (ESI) m/z: 238 [(M + H)$^+$]. Anal. Calcd for $C_{11}H_{15}N_3O_3$: C, 55.69; H, 6.37; N, 17.71. Found: C, 55.31; H, 6.36; N, 17.50. |
| | Pyrrolidine-1-carboxylic acid (2-acetyl-3H-imidazol-4-yl)methylester | | |
| 57 | Phthalic acid (2-acetyl-1H-imidazol-4-yl)methyl methylester | | 1H-NMR (CD$_3$OD) δ: 2.57 (3H, s), 3.78 (3H, s), 5.31 (2H, s), 7.45 (1H, s), 7.58-7.64 (2H, m), 7.67-7.78 (2H, m). MS (ESI) m/z: 303 [(M + H)$^+$]. Anal. Calcd for $C_{15}H_{14}N_2O_4 \cdot 0.25H_2O$: C, 58.73; H, 4.76; N, 9.13. Found: C, 58.60; H, 4.72; N, 9.07. |

TABLE 6-continued

| Example | Compound Name | Structural Formula | Physical Property Data |
|---|---|---|---|
| | Phthalic acid (2-acetyl-3H-imidazol-4-yl)methyl methylester | | |
| 58 | Isophthalic acid (2-acetyl-1H-imidazol-4-yl)methyl methylester | | $^1$H-NMR (CD$_3$OD) δ: 2.58 (3H, s), 3.93 (3H, S), 5.37 (2H, s), 7.49 (1H, s), 7.60 (1H, t, J = 7.8 Hz), 8.24 (2H, t, J = 7.3 Hz), 8.62 (1H, br s). Anal. Calcd for C$_{15}$H$_{14}$N$_2$O$_4$•0.25H$_2$O: C, 58.73; H, 4.76; N, 9.13. Found: C, 58.84; H, 4.78; N, 9.15. |
| | Isophthalic acid (2-acetyl-3H-imidazol-4-yl)methyl methylester | | |

TABLE 7

| Example | Compound Name | Structural Formula | Physical Property Data |
|---|---|---|---|
| 59 | 4-[2-[(2-Acetyl-1H-imidazol-4-yl)methoxy]-2-oxoethyl]piperidine-1-carboxylic acid tert-butyl ester | | $^1$H-NMR (CD$_3$OD) δ: 1.11 (2H, dtd, J = 12.4, 12.4, 4.1 Hz), 1.44 (9H, s), 1.68 (2H, d, J = 12.8 Hz), 1.88-2.00 (1H, m), 2.29 (2H, d, J = 7.3 Hz), 2.55 (3H, s), 2.74 (2H, br s), 4.02 (2H, d, J = 13.3 Hz), 5.10 (2H, s), 7.35 (1H, s). MS (ESI) m/z: 366 [(M + H)$^+$]. Anal. Calcd for C$_{18}$H$_{27}$N$_3$O$_5$•0.5H$_2$O: C, 57.74; H, 7.54; N, 11.22. Found: C, 57.71; H, 7.36; N, 11.19. |
| | 4-[2-[(2-Acetyl-3H-imidazol-4-yl)methoxy]-2-oxoethyl]piperidine-1-carboxylic acid tert-butyl ester | | |
| 60 | Terephthalic acid bis[(2-acetyl-1H-imidazol-4-yl)methyl]ester | | MS (ESI) m/z: 411 [(M + H)$^+$]. Anal. Calcd for C$_{20}$H$_{18}$N$_4$O$_6$: C, 58.53; H, 4.42; N, 13.65. Found: C, 58.29; H, 4.49; N, 13.59. |

TABLE 7-continued

| Example | Compound Name | Structural Formula | Physical Property Data |
|---------|---------------|--------------------|------------------------|
|  | Terephthalic acid (2-acetyl-1H-imidazol-4-yl)methyl (2-acetyl-3H-imidazol-4-yl)methylester | | |
|  | Terephthalic acid bis[(2-acetyl-3H-imidazol-4-yl)methyl]ester | | |

TABLE 8

| Example | Compound Name | Structural Formula | Physical Property Data |
|---------|---------------|--------------------|------------------------|
| 62 | 2-Methoxy benzoic acid (2-acetyl-1H-imidazol-4-yl)methylester | | The mixture of 2-methoxy benzoic acid (2-acetyl-1H-imidazol-4-yl)methylester and 2-methoxy benzoic acid (2-acetyl-3H-imidazol-4-yl)methylester |
|  | 2-Methoxy benzoic acid (2-acetyl-3H-imidazol-4-yl)methylester | | $^1$H-NMR (CDCl$_3$) δ: 2.63 and 2.66 (total 3H, each s), 3.91 (total 3H, each s), 5.36 (2H, s), 6.92-7.03 (2H, m), 7.32-7.56 (2H, m), 7.79-7.86 (1H, m). MS (ESI) m/z: 275 [(M + H)$^+$]. Anal. Calcd for C$_{14}$H$_{14}$N$_2$O$_4$: C, 61.31; H, 5.14; N, 10.21. Found: C, 61.16; H, 5.12; N, 10.12. |
|  | 2-Methoxy benzoic acid [2-acetyl-1-(2-methoxybenzoyl)-1H-imidazol-4-yl]methylester | | The mixture of 2-methoxy benzoic acid [2-acetyl-1-(2-methoxybanzoyl)-1H-imidazol-4-yl]methylester and 2-methoxy benzoic acid [2-acetyl-1-(2-methoxybenzoyl)-3H-imidazol-4-yl]methylester |
|  | 2-Methoxy benzoic acid [2-acetyl-3-(2-methoxybenzoyl)-3H-imidazol-4-yl]methylester | | $^1$H-NMR (CDCl$_3$) δ: 2.55 (3H, s), 3.73 (3H, s), 3.90 (3H, s), 5.35 (2H, s), 7.05-6.91 (4H, m), 7.59-7.46 (4H, m), 7.85 (1H, dd, J = 7.8, 1.8 Hz). MS (ESI) m/z: 409 [(M + H)$^+$]. Anal. Calcd for C$_{22}$H$_{20}$N$_2$O$_6$•0.5H$_2$O: C, 64.13; H, 4.99; N, 6.80. Found: C, 64.09; H, 4.99; N, 6.78. |

TABLE 9

| Example | Compound Name | Structural Formula | Physical Property Data |
|---|---|---|---|
| 63 | 3-Chlorobenzoic acid (2-acetyl-1H-imidazol-4-yl)methylester | | $^1$H-NMR (CDCl$_3$) δ: 2.64 and 2.67 (total 3H, each s), 5.36 and 5.38 (total 2H, each s), 7.30-7.42 (2H, m), 7.50-7.58 (1H, m), 7.90-7.97 (1H, m), 8.05-8.00 (1H, m). Anal. Calcd for C$_{13}$H$_{11}$ClN$_2$O$_3$: C, 56.03; H, 3.98; Cl, 12.72; N, 10.05. Found: C, 55.77; H, 4.01; Cl, 12.62; N, 9.90. |
| | 3-Chlorobenzoic acid (2-acetyl-3H-imidazol-4-yl)methylester | | |
| 64 | 3-Dimethylaminobenzoic acid (2-acetyl-1H-imidazol-4-yl)methylester | | $^1$H-NMR (CDCl$_3$) δ: 2.63 and 2.66 (total 3H, each s), 2.98 and 2.99 (total 6H, each s), 5.33 (total 2H, each s), 6.87-6.94 (1H, m), 7.42-7.26 (5H, m). MS (ESI) m/z: 288 [(M + H)$^+$]. Anal. Calcd for C$_{15}$H$_{17}$N$_3$O$_3$: C, 62.71; H, 5.98; N, 14.63. Found: C, 62.47; H, 5.89; N, 14.38. |
| | 3-Dimethylaminobenzoic acid (2-acetyl-3H-imidazol-4-yl)methylester | | |
| 65 | Malonic acid (2-acetyl-1H-imidazol-4-yl)methyl ethyl ester | | $^1$H-NMR (CDCl$_3$) δ: 1.22-1.31 (3H, m), 2.63 and 2.65 (total 3H, each s), 3.42 and 3.42 (total 2H, each s), 4.16-4.24 (2H, m), 5.21 (2H, s), 7.23 and 7.30 (total 1H, s and d, J = 2.3 Hz). |
| | Malonic acid (2-acetyl-3H-imidazol-4-yl)methyl ethyl ester | | |
| 66 | 2-Phenylmalonic acid bis[(2-acetyl-1H-imidazol-4-yl)methyl]ester | | $^1$H-NMR (CDCl$_3$) δ: 2.62 and 2.65 (total 6H, each s), 3.66 and 3.67 (total 2H, each s), 5.12 and 5.15 (total 4H, each s), 7.17-7.34 (8H, m). |

TABLE 9-continued

| Example | Compound Name | Structural Formula | Physical Property Data |
|---|---|---|---|
| | 2-Phenylmalonic acid bis[(2-acetyl-3H-imidazol-4-yl)methyl]ester | | |
| | 2-Phenylmalonic acid (2-acetyl-1H-imidazol-4-yl)methyl (2-acetyl-3H-imidazol-4-yl)methylester | | |

TABLE 10

| Example | Compound Name | Structural Formula | Physical Property Data |
|---|---|---|---|
| 67 | Cyclohexane-1,3-dicarboxylic acid bis[(2-acetyl-1H-imidazol-4-yl)methyl]ester | | $^1$H-NMR (CDCl$_3$) δ: 1.23-1.43 (2H, m), 1.48-1.62 (4H, m), 1.83-2.40 (6H, m), 2.62-2.66 (6H, m), 5.07-5.16 (4H, m), 7.20-7.26 (2H, m). MS (ESI) m/z: 417 [(M + H)$^+$]. |
| | Cyclohexane-1,3-dicarboxylic acid bis[(2-acetyl-3H-imidazol-4-yl)methyl]ester | | |

TABLE 10-continued

| Example | Compound Name | Structural Formula | Physical Property Data |
|---|---|---|---|
| | Cyclohexane-1,3-dicarboxylic acid 1-(2-acetyl-1H(3H)-imidazol-4-yl)methyl 3-(2-acetyl-3H(1H)-imidazol-4-yl)methylester | | |
| 69 | cis-Cyclohexane-1,4-dicarboxylic acid bis[(2-acetyl-1H-imidazol-4-yl)methyl]ester | | $^1$H-NMR (CD$_3$OD) δ: 1.61-1.71 (4H, m), 1.77-1.90 (4H, m), 2.47-2.54 (2H, m), 2.55 (6H, s), 5.09 (4H, s), 7.34 (2H, s). MS (ESI) m/z: 417 [(M + H)$^+$]. Anal. Calcd for C$_{20}$H$_{24}$N$_4$O$_6$•0.25H$_2$O: C, 57.07; H, 5.87; N, 13.31. Found: C, 57.22; H, 5.86; N, 13.34. |
| | cis-Cyclohexane-1,4-dicarboxylic acid bis[(2-acetyl-3H-imidazol-4-yl)methyl]ester | | |
| | cis-Cyclohexane 1,4-dicarboxylic acid 1-(2-acetyl-1H(3H)-imidazol-4 yl)methyl 4-(2-acetyl-3H(1H)-imidazol-4-yl)methylester | | |

TABLE 11

| Example | Compound Name | Structural Formula | Physical Property Data |
|---|---|---|---|
| 70 | trans-Cyclohexane-1,4-dicarboxylic acid bis[(2-acetyl-1H-imidazol-4-yl)methyl]ester | | $^1$H-NMR (DMSO-D$_6$) δ: 1.16-1.45 (4H, m), 1.85-1.97 (4H, m), 2.25-2.36 (2H, m), 2.50 (6H, s), 4.99 (4H, s), 7.42 (2H, s). MS (ESI) m/z: 417 [(M + H)$^+$]. Anal. Calcd for C$_{20}$H$_{24}$N$_4$O$_6$: C, 57.68; H, 5.81; N, 13.45. Found: C, 57.45; H, 5.83; N, 13.44. |
| | trans-Cyclohexane-1,4-dicarboxylic acid bis[(2-acetyl-3H-imidazol-4-yl)methyl]ester | | |
| | trans-Cyclohexane-1,4-dicarboxylic acid 1-(2-acetyl-1H(3H)-imidazol-4-yl)methyl 4-(2-acetyl-3H(1H)-imidazol-4-yl)methylester | | |
| 71 | trans-Cyclohexane-1,2-dicarboxylic acid bis[(2-acetyl-1H-imidazol-4-yl)methyl]ester | | $^1$H-NMR (DMSO-D$_6$) δ: 1.21-1.32 (4H, m), 1.61-1.72 (2H, m), 1.88-1.96 (2H, m), 2.44-2.56 (8H, m), 4.89-5.08 (4H, m), 7.36 and 7.38 (total 2H, each d, J = 2.8 and 2.3 Hz, respectively). MS (ESI) m/z: 417 [(M + H)$^+$]. Anal. Calcd for C$_{20}$H$_{24}$N$_4$O$_6$: C, 57.68; H, 5.81; N, 13.45. Found: C, 57.52; H, 5.91; N, 13.10. |

TABLE 11-continued

| Example | Compound Name | Structural Formula | Physical Property Data |
|---|---|---|---|
| | trans-Cyclohexane-1,2-dicarboxylic acid bis[(2-acetyl-3H-imidazol-4-yl)methyl]ester | | |
| | trans-Cyclonexane-1,2-dicarboxylic acid 1-(2-acetyl-1H(3H)-imidazol-4-yl)methyl 3-(2-acetyl-3H(1H)-imidazol-4-yl)methylester | | |
| | | | |

TABLE 12

| Example | Compound Name | Structural Formula | Physical Property Data |
|---|---|---|---|
| 72 | 2-[4-(2-Oxocyclopentylmethyl)phenyl]propionic acid (2-acetyl-1H-imidazol-4-yl)methylester | | $^1$H-NMR (CDCl$_3$) δ: 1.49 (3H, d, J = 6.9 Hz), 1.68-1.80 (2H, m), 1.92-2.01 (1H, m), 2.05-2.16 (2H, m), 2.29-2.40 (2H, m), 2.48-2.57 (1H, m), 2.62 (3H, s), 3.08 (1H, d, J = 12.0 Hz), 3.73 (1H, d, J = 7.4 Hz), 5.12 (2H, s), 6.95-7.05 (1H, m), 7.07-7.23 (5H, m). MS (ESI) m/z: 369 [(M + H)$^+$]. Anal. Calcd for C$_{21}$H$_{24}$N$_4$O$_4$: C, 68.46; H, 6.57; N, 7.60. Found: C, 68.15; H, 6.50; N, 7.56. |

| Example | Compound Name | Structural Formula | Physical Property Data |
|---|---|---|---|
| | 2-[4-(2-Oxocyclopentylmethyl)phenyl]propionic acid (2-acetyl-3H-imidazol-4-yl)methylester | | |
| 73 | (2R)-[4-[(2S)-Oxocyclopentylmethyl]phenyl]propionic acid (2-acetyl-1H-imidazol-4-yl)methylester | | $^1$H-NMR (CDCl$_3$) δ: 1.48 and 1.49 (total 3H, each d, J = 7.4 and 6.9 Hz, respectively), 1.70-2.01 (2H, m), 2.05-2.17 (2H, m), 2.27-2.39 (2H, m), 2.46-2.58 (1H, m), 2.62 and 2.63 (total 3H, each s), 3.02-3.14 (1H, m), 3.68-3.77 (1H, m), 5.03-5.14 (2H, m), 6.96-7.23 (6H, m). MS (ESI) m/z: 369 [(M + H)$^+$]. Anal. Calcd for C$_{21}$H$_{24}$N$_4$O$_4$: C, 68.46; H, 6.57; N, 7.60. Found: C, 68.47; H, 6.55; N, 7.66. |
| | (2R)-[4-[(2S)-Oxocyclopentylmethyl]phenyl]propionic acid (2-acetyl-3H-imidazol-4-yl)methylester | | |
| 74 | (2S,5S)-Pyrrolidine-1,2,5-tricarboxylic acid 2-(2-acetyl-1H-imidazol-4-yl)methyl 1-tert-butyl 5-methylester | | $^1$H-NMR (CDCl$_3$) δ: 1.25, 1.34, 1.40, and 1.44 (total 9H, each s), 1.93-2.03 (2H, m), 2.25-2.39 (2H, m), 2.61-2.66 (3H, m), 3.727, 3.733, and 3.74 (total 3H, each s), 4.41-4.59 (2H, m), 5.08-5.26 (2H, m), 7.20-7.32 (2H, m). MS (ESI) m/z: 396 [(M + H)$^+$]. |
| | (2S,5S)-Pyrrolidine-1,2,5-tricarboxylic acid 2-(2-acetyl-3H-imidazol-4-yl)methyl 1-tert-butyl 5-methylester | | |

TABLE 13

| Example | Compound Name | Structural Formula | Physical Property Data |
|---|---|---|---|
| 77 | Acetic acid (2-acetyl-4-hydroxymethylimidazol-1-yl)methylester | | $^1$H-NMR (CDCl$_3$) δ: 2.09 (3H, s), 2.68 (3H, s), 4.65 (2H, d, J = 5.5 Hz), 6.27 (2H, s), 7.27 (1H, s). MS (ESI) m/z: 213 [(M + H)$^+$]. Anal. Calcd for C$_9$H$_{12}$N$_2$O$_4$: C, 50.94; H, 5.70; N, 13.20. Found: C, 50.69; H, 5.60; N, 13.16. |
| 78 | Butyric acid (2-acetyl-4-hydroxymethylimidazol-1-yl)methylester | | $^1$H-NMR (CDCl$_3$) δ: 0.92 (3H, t, J = 7.5 Hz), 1.64 (3H, q, J = 7.8 Hz), 2.10 (1H, s), 2.32 (2H, t, J = 7.5 Hz), 2.68 (3H, s), 4.65 (2H, d, J = 5.0 Hz), 6.28 (2H, s). MS (ESI) m/z: 241 [(M + H)$^+$]. Anal. Calcd for C$_{11}$H$_{16}$N$_2$O$_4$•0.25H$_2$O: C, 53.98; H, 6.79; N, 11.45. Found: C, 53.85; H, 6.58; N, 11.35. |

Preparative Example

Referring to the above-mentioned Examples, the following compounds can be prepared.

TABLE 14

| Preparative Example | Compound Name | Structural Formula |
|---|---|---|
| 1 | 1-(4-Fluoro-5-hydroxymethyl-1H-imidazol-2-yl)-ethanone | |
| 2 | 1-(5-Fluoro-4-hydroxymethyl-1H-imidazol-2-yl)-ethanone | |
| 3 | 1-(4-Chloro-5-hydroxymethyl-1H-imidazol-2-yl)-ethanone | |
| 4 | 1-(5-Chloro-4-hydroxymethyl-1H-imidazol-2-yl)-ethanone | |
| 5 | Benzoic acid 2-acetyl-4-hydroxymethyl-imidazol-1-yl methylester | |
| 6 | Acetic acid 2-acetyl-5-hydroxymethyl-imidazol-1-yl methylester | |
| 7 | Butyric acid 2-acetyl-5-hydroxymethyl imidazol-1-yl methylester | |

TABLE 14-continued

| Preparative Example | Compound Name | Structural Formula |
|---|---|---|
| 8 | 2,2-Dimethyl-propionic acid 2-acetyl-5-hydroxy-methyl-imidazol-1-yl methylester | |
| 9 | Benzoic acid 2-acetyl-5-hydroxy-methyl-imidazol-1-yl methylester | |
| 10 | 1-(1,4-Bis-hydroxy-methyl-1H-imidazol-2-yl)-ethanone | |
| 11 | 1-(1,5-Bis-hydroxy-methyl-1H-imidazol-2-yl)-ethanone | |
| 12 | 2-Acetyl-4-hydroxy-methyl-imidazole-carboxylic acid tert-butyl ester | |
| 13 | 2-Acetyl-5-hydroxy-methyl-imidazole-1-carboxylic acid tert-butyl ester | |
| 14 | 2-Acetyl-4-hydroxy-methyl-imidazole-1-sulfonic acid diethylamide | |
| 15 | 2-Acetyl-5-hydroxy-methyl-imidazole-1-sulfonic acid diethylamide | |
| 16 | 1-[4-Hydroxy-methyl-1-(pyrrolidine-1-sulfonyl)-1H-imidazol-2-yl]-ethanone | |
| 17 | 1-[5-Hydroxy-methyl-1-(pyrrolidine-1-sulfonyl)-1H-imidazol-2-yl]-ethanone | |
| 18 | 1-[4-Hydroxy-methyl-1-(piperidine-1-sulfonyl)-1H-imidazol-2-yl]-ethanone | |
| 19 | 1-[5-Hydroxy-methyl-1-(pieridine-1-sulfonyl)-1H-imidazol-2-yl]-ethanone | |
| 20 | 1-[4-Hydroxy-methyl-1-(morpholine-4-sulfonyl)-1H-imidazol-2-yl]-ethanone | |

TABLE 15

| Preparative Example | Compound Name | Structural Formula |
|---|---|---|
| 21 | 1-[5-Hydroxymethyl-1-(morpholine-4-sulfonyl)-1H-imidazol-2-yl]-ethanone | |
| 22 | 3-Methyl butyric acid (2-acetyl-1H-imidazol-4-yl)methylester | |
| 23 | 3-Methyl butyric acid (2-acetyl-3H-imidazol-4-yl)methylester | |
| 24 | Cyclohexyl acetic acid (2-acetyl-1H-imidazol-4-yl)methylester | |
| 25 | Cyclohexyl acetic acid (2-acetyl-3H-imidazol-4-yl)methylester | |
| 26 | Nicotinic acid (2-acetyl-1H-imidazol-4-yl)methylester | |

TABLE 15-continued

| Preparative Example | Compound Name | Structural Formula |
|---|---|---|
| 27 | Nicotinic acid (2-acetyl-3H-imidazol-4-yl)methylester | |
| 28 | Acetic acid 1-(2-acetyl-4-hydroxymethyl-imidazol-1-yl)ethyl ester | |
| 29 | Acetic acid 1-(2-acetyl-5-hydroxymethyl-imidazol-1-yl)ethyl ester | |
| 30 | 2-Amino-3-benzyloxy-propionic acid (2-acetyl-3H-imidazol-4-yl)methylester | |
| 31 | 2-Amino-3-benzyloxy-propionic acid (2-acetyl-1H-imidazol-4-yl)methylester | |
| 32 | 1-[5-Hydroxymethyl-1H-[4-$^2$H]imidazol-2-yl]ethanone | |
| 33 | 1-[-4-Hydroxymethyl-1H-[5-$^2$H]imidazol-2-yl]ethanone | |

TABLE 15-continued

| Preparative Example | Compound Name | Structural Formula |
|---|---|---|
| 34 | Acetic acid 2-(2-acetyl-3H-imidazol-4-ylmethoxy)ethyl ester | |
| 35 | Acetic acid 2-(2-acetyl-1H-imidazol-4-ylmethoxy)ethyl ester | |

Formulation Example 5 g of a compound obtained in an Example, 90 g of lactose, 34 g of corn starch, 20 g of crystalline cellulose and 1 g of magnesium stearate are mixed with a blender, and subsequently the mixture is tabletted with a tablet-making machine to obtain tablets.

Test Example 1

Mouse Host-Versus-Graft Reaction (mHvGR)

Male BALB/c mice at age 6 weeks and Male C57BL/6j mice at age 6 weeks were purchased from Charles River Laboratories Japan Inc. Mice that had reached age 7 weeks after 1-week acclimation were used for the experiment. A group of 5 animals was used for the experiment. The spleens extirpated from BALB/c mice or C57BL/6j mice were crushed in RPMI1640 medium (Invitrogen corp.). Subsequent filtration using 70 μm Cell Strainer (Becton, Dickinson and Company, Japan) allowed spleen cells to be prepared. Collected cells were suspended in RPMI1640 medium so as to be $1 \times 10^8$ cells/mL, each 50 μl, of which was injected into soles of the right and left hind paws of BALB/c mice to induce mouse host-versus-graft reaction (mHvGR).

Methyl Cellulose #400 (MC, Nacalai Tesque, Inc.) was dissolved with sterilized distilled water so as to be 0.5% (0.5% MC solution), and was used as solvent. The necessary amount of the analyte was weighed, and subsequently suspended in the solvent using a mortar and a pestle. The solution to be administered was prepared so as to be 10 mL per 1 kg of body weight. The prepared compound solution was administered orally using a stomach tube once a day for 3 days from the day on which mHvGR was induced. At 4 days after the induction of mHvGR, the mice were euthanized by exsanguination from inferior vena cava and abdominal aorta under deep diethylether anesthesia, and popliteal lymph nodes were extirpated. The wet weight of the right and left lymph nodes was measured individually.

Compounds of Examples 1 to 34 reduced host-versus-graft reaction.

Test Example 2

S1P Lyase Inhibitory Capacity in Mice

Male BALB/c mice at age 6 weeks were purchased from Charles River Laboratories Japan Inc. Mice that had reached age 7 weeks after 1-week acclimation were used for the experiment. A group of 5 animals was used for the experiment. The necessary amount of the analyte was weighed, and subsequently suspended in a 0.5% MC solution using a mortar and a pestle. The solution to be administered was prepared so as to be 10 mL per 1 kg of body weight. The prepared compound solution was administered orally in a single dose using a stomach tube.

Dipotassium dihydrogen ethylenediaminetetraacetate (EDTA-2K, Nacalai Tesque, Inc.) was dissolved with water for injection so as to be 5% (5% EDTA-2K solution). At 1, 3, 8, 24, 48 hours before and after oral administration, mice were subjected to laparotomy under diethylether anesthesia, and 0.5 mL of blood was collected from inferior vena cava using a syringe with a 5% EDTA-2K solution having been passed therethrough in advance. At that time, the thymus was also extirpated. The obtained blood was handled under the condition of room temperature until measurement. For measurement of the number of lymphocytes, an automatic blood cell counter (ADVIA120, Siemens Healthcare Diagnostic, Inc.) was used.

The extirpated thymus was crushed by means of either a method using zirconia beads in the presence of 500 μl, of a homogenization buffer (50 mM HEPES-NaOH (pH=7.4), 0.15 M NaCl, 10% Glycerol, 1 mM EDTA, 1 mM DTT, complete protease inhibitor cocktail (Roche, #4693132)), or a method using Potter-Elvehjem type homogenizer after mincing. After further ultrasonication with a sonicator, centrifugation was conducted at 4° C. and 1000 G for 3 minutes to collect the supernatant. After the proteins of the supernatant were quantified with Bradford method, the supernatant was instantly frozen with liquid nitrogen, and subsequently stored at −80° C. (thymus extract).

In order to measure S1P lyase activity, the thymus extract was diluted to 1 mg/mL with a homogenization buffer, and reacted at 37° C. for 1 hour in an enzyme reaction solution (0.1 M K-Pi (pH=7.4), 25 mM NaF, 5 mM $Na_3VO_4$, 1 mM EDTA, 1 mM DTT, 0.1% Triton X-100, 2 μM cold dhS1P) containing [$^3$H]dh S1P (3.4 nM) which is a substrate. Those subjected to the reaction for 1 hour on ice were set as negative controls. After the reaction, sodium hydroxide was added so as to have the final concentration of 0.1 M, and an equivalent of $CHCl_3$/MeOH (2:1) mixed solution was further added followed by stirring. After centrifugation at room temperature and 8400 G for 3 minutes, the aqueous layer portion was collected, and the radioactivity was measured with a liquid scintillation counter.

Compounds of Examples 1 and 5 inhibited S1P lyase in mice.

Test Example 3

Fluctuation in Number of Lymphocytes in Peripheral Blood in Rats

Male LEW/Crj rats at age 3 or 6 weeks were purchased from Charles River Laboratories Japan Inc. The rats were acclimated for 1 week, and used for the experiment. A group of 3 or 5 animals was used for the experiment. The necessary amount of the analyte was weighed, and subsequently suspended in a 0.5% MC solution using a mortar and a pestle or a homogenizer. The solution to be administered was prepared so as to be 5 mL per 1 kg of body weight. The prepared solution was administered orally in a single dose using a stomach tube. At 1, 3, 7, 8, 24 or 48 hours before and after the oral administration, rats were subjected to laparotomy under diethylether anesthesia or under isoflurane anesthesia, and 2 mL of blood was collected from inferior vena cava immediately into an anticoagulant (EDTA-2K)-coated vacuum sealed blood collection tube (Nipro Corporation). After being inverted, the tube was handled under the condition of room temperature until measurement. For measurement of the number of lymphocytes, an automatic blood cell counter (ADVIA120, Siemens Healthcare Diagnostic, Inc.) was used.

Compounds of Examples 2, 5, 6, 15, 16, 35 to 73, and 75 to 84 reduced the number of lymphocytes in peripheral blood.

Test Example 4

Fluctuation in Number of Lymphocytes in Peripheral Blood in Monkeys

Female cynomolgus monkeys (from China/Philippines) were purchased from Hamri Co. Ltd. or LSG Corporation. The necessary amount of the analyte was weighed, and subsequently suspended in a 0.5% MC solution using a mortar and a pestle. The solution to be administered was prepared so as to be 5 mL per 1 kg of body weight. The cynomolgus monkeys were fasted from about 17 hours before administration up to 7 hours after administration. The prepared compound solution was administered orally in a single dose using a stomach tube. At 0.5, 1, 2, 4 and 7 hours before and after the oral administration, and on 1, 2, 3 days after administration, about 0.8 mL of blood was collected from cephalic vein or saphenous vein using an injector immediately into an anticoagulant-coated vacuum sealed blood collection tube. After being inverted, the tube was handled under the condition of room temperature until measurement. For measurement of the number of lymphocytes, an automatic blood cell counter was used.

Compounds of Examples 1 to 5, 9, 15, 35, 36 and 67 reduced the number of lymphocytes in peripheral blood.

Test Example 5

Measurement of S1P Lyase Inhibitory Capacity in Rats

S1P lyase inhibitory capacity was measured in accordance with FEBS Letters 350 (1994) 91-95, JBC Vol. 266, No. 19, pp. 12502-12507, 1991. Examples 2, 35, 36, 46 to 48, 67 and 73 inhibited S1P lyase in rats.

Test Example 6

Test in Pathological Model

Pathological models such as experimental autoimmune encephalomyelitis (Clin. Exp. Immunol., 120, 526-531 (2000), J. Neuroimmunol., 129, 1-9 (2002), Annu. Rev. Immunol., 10, 153-187 (1992), Eur. J. Immunol., 25, 1951-1959 (1995)), collagen-induced arthritis (Current Protocols in Immunology (1996) 15.5.1-15.5.24), aspirin asthma (Arthritis Rheum. 2010 January; 62(1): 82-92), GPI-induced arthritis (Arthritis Res Ther. 2008; 10(3): R66. Epub 2008 Jun. 5), antibody-induced arthritis (J. Immunol. 2003 Apr. 15; 170(8): 4318-24), psoriasis (J. Immunol. 2009 May 1; 182(9): 5836-45, J Clin Invest. 2008 February; 118(2): 597-607, Nature 2007 445: 648-651), inflammatory bowel disease (Current Protocols in Immunology (2001) 15.19.1-15.19.14, Proc Natl Acad Sci USA. 2009 Mar. 3; 106(9): 3300-5. Epub 2009 Feb. 6), systemic lupus erythematosus (Current Protocols in Immunology (2002) 15.20.1-15.20.22), and acute lung injury (Am. J. Respir. Cell Mol. Biol. 2010 Dec. 10 as doi: 10.1165/rcmb. 2010-0422OC) are used to evaluate the test substances.

Test Example 7

Membrane Permeability

Pursuant to Journal of pharmaceutical sciences, 97(2), 712-725 (2008), the membrane permeability of the test substances is evaluated as follows.

Madin-Darby canine kidney (obtained from American Type Culture Collection) cells (hereinafter, referred to as MDCK cells) are cultured in Minimum Essential Medium (manufactured by GIBCO, Inc.) containing 10% (v/v) fetal bovine serum (manufactured by GIBCO, Inc.), a penicillin-streptomycin mixture (manufactured by GIBCO, Inc.) and L-glutamine.

After cells are inoculated so as to form a monolayer, inoculation is conducted in HTS-24 well transwell (manufactured by Costar Corporation) so as to be $1.65 \times 10^5$ cells/mL, followed by culturing for 6 days. To 10× Hanks' Balanced Salt Solution (manufactured by GIBCO, Inc.) are added $NaHCO_3$ (final concentration: 0.35 g/L), D-glucose (final concentration: 3.5 g/L), HEPES (manufactured by Sigma Corporation, final concentration: 10 mM), $CaCl_2$ (final concentration 0.14 g/l) and $MgSO_4$ (final concentration: 0.098 g/L), followed by adjustment of the pH to 6.0 or 7.4 using 1 M HCl or 1 M NaOH to prepare Transport Buffer.

Then, Transport Buffer (pH=6.0) (100 μL) of 10 μM of each test substance is added to the apical side of the cell. Transport Buffer (pH 7.4) (600 μL) containing 4% (w/v) bovine serum albumin is added to the basolateral side thereof. Metoprolol is used as a positive control.

After incubation at 37° C. for 1 hour, LC/MS/MS system (10 mM $HCO_2NH_4$/acetonitrile, 100/0→20/80→100/0) equipped with Alliance 2790 HPLC (manufactured by Waters Corporation), Atlantis dC18 column (2.1 mm×20 mm, 3 μm, manufactured by Waters Corporation) and TSQ7000 mass spectrometer (manufactured by ThermoQuest Corporation) is used to analyze the basolateral side. The concentration of each test substance at the basolateral side is calculated from a peak area with respect to each calibration curve. Permeation coefficient ($P_{app}$) from the apical side to the basolateral side of each test substance is calculated from the test substance concentration ($C_b(\mu M)$) at the basolateral side measured by LC/MS/MS and the initial concentration of 10 μM at the apical side using the following mathematical expression. In the following mathematical expression, 3600 sec denotes the reflux time for the compound, and 0.33 cm² denotes the area of transwell filter.

$$P_{app}(\text{cm/sec}) = \frac{C_b(\mu M) \times 600(\mu l)}{10(\mu M) \times 3600(\text{sec}) \times 0.33(\text{cm}^2)} \quad [\text{Equation 1}]$$

INDUSTRIAL APPLICABILITY

According to the present invention, it is possible to provide a pharmaceutical composition for preventing or treating inflammatory bowel disease, acute lung injury, autoimmune disease, multiple sclerosis or allergic disease, or for suppressing rejection response against transplant.

The invention claimed is:
1. A compound represented by the general formula (I):

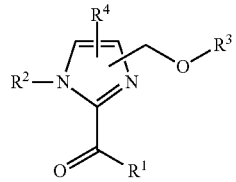

or an isotope thereof or a pharmaceutically acceptable salt thereof wherein,
$R^1$ is a methyl group which may be substituted with the same or different 1 to 3 halogen atoms,
$R^2$ is a C1-C6 alkyl group which may be substituted with the same or different 1 to 3 halogen atoms, a C3-C6 cycloalkyl group, a C1-C6 alkoxy C1-C6 alkyl group, a C3-C6 cycloalkoxy C1-C6 alkyl group, a C2-C6 alkenyl group, a di(C1-C6 alkyl group)amino group, a furanylmethyl group, an oxetanyl group, an acetyloxymethyl group, a propylcarbonyloxymethyl group, a tert-butylcarbonyloxymethyl group, a phenylcarbonyloxymethyl group, a hydroxymethyl group, a dimethylaminosulfonyl group, a diethylaminosulfonyl group, a pyrrolidinesulfonyl group, a piperidinesulfonyl group or a morpholinesulfonyl group,
$R^3$ is a hydrogen atom, an acetyl group, a benzoyl group or a pivaloyl group, and
$R^4$ is a hydrogen atom or a halogen atom.

2. The compound or isotope thereof or pharmaceutically acceptable salt thereof according to claim 1, wherein $R^1$ is a methyl group which may be substituted with 1 to 3 fluorine atoms.

3. The compound or isotope thereof or pharmaceutically acceptable salt thereof according to claim 1, wherein $R^1$ is a methyl group or a difluoromethyl group.

4. The compound or isotope thereof or pharmaceutically acceptable salt thereof according to claim 1, wherein $R^2$ is a C2-C6 alkyl group, a cyclopropyl group, a C1-C2 alkoxy C1-C3 alkyl group, a cyclohexyloxymethyl group, a vinyl group, a furanylmethyl group, an oxetanyl group or a dimethylaminosulfonyl group.

5. The compound or isotope thereof or pharmaceutically acceptable salt thereof according to claim 1, wherein $R^2$ is an ethyl group, a propyl group, a sec-butyl group, a tert-butyl group, a pentyl group, a hexyl group, a cyclopropyl group, a methoxymethyl group, a methoxyethyl group, a methoxyisopropyl group, an ethoxymethyl group, a cyclohexyloxymethyl group, a vinyl group, a furanylmethyl group, an oxetanyl group or a dimethylaminosulfonyl group.

6. The compound or isotope thereof or pharmaceutically acceptable salt thereof according to claim 1, wherein $R^2$ is an ethyl group or a vinyl group.

7. The compound or isotope thereof or pharmaceutically acceptable salt thereof according to claim 1, wherein $R^3$ is a hydrogen atom.

8. The compound or isotope thereof or pharmaceutically acceptable salt thereof according to claim 1, wherein $R^4$ is a hydrogen atom.

9. A compound represented by the general formula (II):

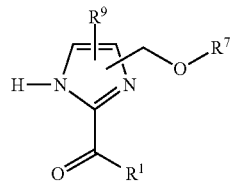

or an isotope thereof or a pharmaceutically acceptable salt thereof wherein,
$R^1$ is a methyl group which may be substituted with the same or different 1 to 3 halogen atoms,
$R^7$ is a hydrogen atom or —C(O)—$R^8$,
$R^8$ is a C1-C8 alkyl, a C3-C8 cycloalkyl, a phenyl, a pyridyl, a naphthyl, an amino, a pyrrolidinyl, a piperidinyl or a morpholinyl group which may have the same or different 1 to 3 substituents selected from substituent group α,
the substituent group α is the group consisting of a halogen atom, a hydroxy group, a C1-C8 alkyl group, a C3-C8 cycloalkyl group, a C1-C8 alkoxy group, a C3-C8 cycloalkoxy group, an amino group, a mono or di(C1-C8 alkyl)amino group, a carboxyl group, a C1-C8 alkoxycarbonyl group, a phenyl group, a pyridyl group, a phenoxy group, a phenyl C1-C6 alkoxy group, a tert-butyloxycarbonylpiperidinyl group, a (2-acetyl-1H-imidazol-4-yl)methyloxycarbonyl group, a (2-acetyl-3H-imidazol-4-yl)methyloxycarbonyl group and an oxocyclopentylmethylphenyl group, and
$R^9$ is a hydrogen atom, a halogen atom or a C1-C6 alkyl group.

10. A compound selected from the group consisting of:
1-(4-hydroxymethyl-1-methoxymethyl-1H-imidazol-2-yl)ethanone,
1-(4-hydroxymethyl-1-isopropyl-1H-imidazol-2-yl)ethanone,
1-(4-hydroxymethyl-1-vinyl-1H-imidazol-2-yl)ethanone,
1-(4-hydroxymethyl-1H-imidazol-2-yl)ethanone,
1-(5-hydroxymethyl-1H-imidazol-2-yl)ethanone,
1-[4-[hydroxy[(²H)₂]methyl]-1H-imidazol-2-yl]ethanone,
1-[5-[hydroxy[(²H)₂]methyl]-1H-imidazol-2-yl]ethanone,
1-[4-[hydroxy[(²H)₂]methyl]-1-methoxymethyl-1H-imidazol-2-yl]ethanone,
benzoic acid (2-acetyl-1H-imidazol-4-yl)methylester,
benzoic acid (2-acetyl-3H-imidazol-4-yl)methylester,
cis-cyclohexane-1,3-dicarboxylic acid bis[(2-acetyl-1H-imidazol-4-yl)methyl]ester, cis-cyclohexane-1,3-dicarboxylic acid bis[(2-acetyl-3H-imidazol-4-yl)methyl]ester, cis-cyclohexane-1,3-dicarboxylic acid 1-(2-acetyl-1H-imidazol-4-yl)methyl 3-(2-acetyl-1H-imidazol-4-yl)methylester, and cis-cyclohexane-1,3-dicarboxylic acid 1-(2-acetyl-3H-imidazol-4-yl)methyl 3-(2-acetyl-1H-imidazol-4-yl)methylester.

11. A pharmaceutical composition containing as an active ingredient the compound or isotope thereof or pharmaceutically acceptable salt thereof according to claim 1 or claim 9.

12. A method of treating inflammatory bowel disease, acute lung injury, rheumatoid arthritis, systemic lupus erythematosus, antiphospholipid antibody syndrome, multiple myositis, dermatomyositis, systemic scleroderma, Sjogren's syndrome, polyarteritis nodosa, microscopic polyarteritis, allergic granulomatous angiitis, Wegener's granulomatosis, mixed connective tissue disease, multiple sclerosis or allergic disease, or suppressing rejection response against transplant, comprising administering to a mammal a therapeutically effective amount of the pharmaceutical composition according to claim 11.

13. The method according to claim 12, wherein the inflammatory bowel disease is ulcerative colitis or Crohn's disease.

14. The method according to claim 12, wherein the allergic disease is atopic dermatitis, allergic rhinitis, pollinosis, allergic conjunctivitis, allergic gastroenteritis, bronchial asthma, infantile asthma, food allergy, drug allergy or urticaria.

15. The method according to claim 12, wherein the mammal is a human.

* * * * *